United States Patent
Healy et al.

(10) Patent No.: US 8,298,606 B2
(45) Date of Patent: Oct. 30, 2012

(54) METHODS AND COMPOSITIONS FOR STABILIZING THE MYOCARDIUM

(75) Inventors: Kevin E. Healy, Moraga, CA (US);
Samuel Thomas Wall, Oslo (NO);
Mark Ratcliffe, Piedmont, CA (US);
Julius Guccione, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 1005 days.

(21) Appl. No.: 11/986,525

(22) Filed: Nov. 20, 2007

(65) Prior Publication Data

US 2009/0123412 A1 May 14, 2009

Related U.S. Application Data

(63) Continuation-in-part of application No. 10/385,900, filed on Mar. 10, 2003, now Pat. No. 7,985,601, and a continuation-in-part of application No. 11/394,042, filed on Mar. 29, 2006.

(60) Provisional application No. 60/860,184, filed on Nov. 20, 2006, provisional application No. 60/362,621, filed on Mar. 8, 2002, provisional application No. 60/666,734, filed on Mar. 29, 2005.

(51) Int. Cl.
*A61L 33/00* (2006.01)
(52) U.S. Cl. ...... 427/2.1; 436/514; 436/526; 435/283.1; 427/2.22
(58) Field of Classification Search ............................ None
See application file for complete search history.

(56) References Cited

U.S. PATENT DOCUMENTS

| | | | |
|---|---|---|---|
| 5,219,564 A | 6/1993 | Zalipsky et al. | |
| 5,334,640 A | 8/1994 | Desai et al. | |
| 5,760,004 A | 6/1998 | Stedronsky | |
| 6,156,572 A | 12/2000 | Bellamkonda et al. | |
| 6,224,893 B1 | 5/2001 | Langer et al. | |
| 6,270,903 B1 | 8/2001 | Feng et al. | |
| 6,639,014 B2 | 10/2003 | Pathak et al. | |
| 7,985,601 B2 * | 7/2011 | Healy et al. | 436/535 |
| 2002/0007217 A1 | 1/2002 | Jacob et al. | |
| 2002/0122792 A1 | 9/2002 | Stegmann | |
| 2002/0169360 A1 | 11/2002 | Taylor et al. | |
| 2002/0188170 A1 | 12/2002 | Santamore et al. | |
| 2003/0175410 A1 | 9/2003 | Campbell et al. | |
| 2004/0001892 A1 | 1/2004 | Healy et al. | |
| 2004/0208845 A1 | 10/2004 | Michal et al. | |
| 2005/0271631 A1 | 12/2005 | Lee et al. | |
| 2006/0083717 A1 | 4/2006 | Lee et al. | |
| 2008/0065047 A1 | 3/2008 | Sabbah et al. | |

OTHER PUBLICATIONS

Barber, Thomas A. et al., "Peptide-modified p(AAm-*co*-EG/AAc) IPNs grafted to bulk titanium modulate osteoblast behavior *in vitro*", *Journal of Biomedical Materials Research*, 64A, pp. 38-47 (2003).
Bearinger et al., "Biomolecular modification of p(AAm-*co*EG/AA) IPNs supports osteoblast adhestion and phenotypic expression", *Journal of Biomaterials Science, Polymer Edition*, 9(7):629-52, 1998.

(Continued)

*Primary Examiner* — Nelson C. Yang
(74) *Attorney, Agent, or Firm* — Morgan, Lewis & Bockius LLP; Jeffry S. Mann; Ada O. Wong

(57) ABSTRACT

The present invention provides materials and methods that can serve as a prosthetic and/or, for tissue engineer applications, as a supporting matrix in the stabilization of the myocardium.

14 Claims, 51 Drawing Sheets

OTHER PUBLICATIONS

Bellamkonda et al., "Laminin Oligopeptide Derivatized Agarose Gets Allow Three-Dimensional Neurite Extension in Vitro", *J. Neurosci Research*, 41(4):501-9, 1995.

Conley, Brock J. et al., "Derivation, propagation and differentiation of human embryonic stem cells", *Int. J. Biochem. Cell Bio.*, vol. 36, pp. 555-567 (2004).

Drumheller, et al., "Multifuctional poly(ethylene glycol) semi-interpenetrating polymer networks as highly selective adhesive substrates for bioadhesive peptide grafting", *Biotech & Bioeng*, 1994, vol. 43, pp. 772-780.

Freitas, Roberto S. et al., "Temperature Sensitive Gels as Extraction Solvents", *Chemical Eng. Sci.*, 1987, vol. 42, No. 1, pp. 97-103.

Gilanyi et al., Characterisation of monodisperse poly(N-isopropylacrylamide) microgel particles, *Phys. Chem. Chem. Phys.* 2, 2000, pp. 1973-1977.

Harbers et al., "Development and Chracterization of a High-Throughput System for Assessing Cell-Surface Receptor-Ligand Engagement", *Langmuir*, 21(18):8374-8384, 2005.

Healy, Kevin E. "Control of Cell Function with Tunable Hydrogel Networks", Proceedings of the 26th Annual International Conference of the IEEE EMBS (2004).

Hoffman, Allan S. et al., "Thermally Reversible Hydrogels: II. Delivery and Selective Removal of Substances from Aqueous Solutions", *Journal of Controlled Release*, 1986, vol. 4, pp. 213-222.

Horowitz, A. et al., "The Role of Oxygen Dimer in Oxygen Photolysis in the Herzberg Continuum. A Temperature Dependence Study", *J. Phys. Chem.*, 93, p. 7859-7863 (1989).

Johansson et al., "Collagenase-3 (MMP-13) Is Espressed by Hypertrophic Chondrocytes, Periosteal Cells, and Osteoblasts During Human Fetal Bone Development", *Developmental Dynamics*, 208:387-397, 1997.

Lakhiari, H. et al., "Temerpature-responsive size exculsion chromatography using poly(N-isopropylacrylamide) grafted silica", *Biochimica et Biophysica Acta*, 1998, vol. 1379, pp. 303-313.

Massova et al., "Matrix metalloproteinases: structures, evolution, and diversification", *FASEB Journal*, 12:1075-1095, 1998.

Mitchell et al., "Cloning, Expression, and Type II Collagenolytic Activity of Matrix Metalloproteinase-13 from Human Osteoarthritic Cartilage", *Journal of Clinical Investigation*, 97:761-768, 1996.

Miyata et al., "Biomolecule-sensitive hydorgels", *Adv. Drug. Deliv. Rev.*, Jan. 2002, vol. 54(1): pp. 79-98.

Monji, Nobuo et al., "A Novel Immuoassay System and Bioseparation Process Based on Thermal Phase Separating Polymers", *Applied Biochemistry and Biotechnology*, 1987, vol. 14, pp. 107-120.

Netzel-Arnett et al., "Sequence Specificities of Human Firbroblast and Neutrophil Collagenases", *Journal of Biological Chemistry*, 266:6747-6755, 1991.

Okano, Teruo et al., "A novel recovery system for curltured cells using plasma-treated polystyrene dishes grafted with poly(N-isopropylacrylamide)", *Journal of Biomedical Materials Research*, 1993, vol. 27, pp. 1243-1251.

Park, Tae Gwan et al., "Immobilization of Arthrobacter simplex in Thermally Reversible Hydrogels: Effect of Gel Hydrophobicity on Steroid Conversion", *Biotechnol*, 1991, vol. 7, pp. 383-390.

Pauling, L., "The Nature of the Chemical Bond. Application of Results Obtained from the Quantum Mechanics and from a Theory of Paramagnetic Susceptibility to the Structure of Molecules", *Gates Chemical Laboratory, California Institute of Technology*, 53: p. 1387-1400 (1931).

Rudolph, W. et al., "Aluminium(III) hydration in aqueous solutions. A Raman spectroscopic investigation and an *ab initio* molecular orbital study of aluminium(III) water clusters", *Phys. Chem. Chem. Phys.*, 2, p. 5030-5040 (2000).

Shimizu, Shinichi et al., "In Vitro Studies on a New Method for Islet Microencapsulation Using a Thermoreversible Gelation Polymer, N-isopropylacrylamide-Based Copolymer", *Artif. Organs*, 1996, vol. 20, No. 11, pp. 1232-1237.

Sigma-Aldrich, Tutorial: Biocompatible/Biodegradable Materials, 2005, pp. 1-8.

Silva et al., "Selective Differentiation of Neural Progenitor Cells by High-Epitope Density Nanofibers", *Science*, 303(5662): 1352-5, 2004.

Steiner, T., "The Hydrogen Bond in the Solid State", *Agnew Chem. Int. Ed.*, 41, p. 48-76 (2002).

Stile, Ranee A. et al., Poly(N-isopropylacrylamide)-based semi-interpenetrating polymer networks for tissue engineering applications. 1. effects of linear poly(acrylic acid) chains on phase behavior, *Biomacromolecules*, 3(3), 2002, pp. 591-600.

Stile, Ranee A. et al., "Thermo-Responsive Peptide-Modified Hydrogels for Tissue Regeneration", *Biomacromolecules*, 2001, vol. 2, pp. 185-194.

Stile, Ranee A. et al., "Peptide-Modified Thermoreversible Hydrogels for Tissue Regeneration", *219th Book of Abstracts*, ACS National Meeting, Mar. 26-30, 2000.

Stile, Ranee A. et al., "Synthesis and Characterization of Injectable Poly(N-isopropylacrylamide)-Based Hydrogels that support Tissue Formation in Vitro", *Macromolecules*, 1999, vol. 32, pp. 7370-7379.

Tashiro et al., "A Synthetic Peptide Containing the IKVAV Sequence from the A Chain of Laminin Mediates Cell Attachment, Migration, and Neurite Outgrowth", *J. Bio. Chem.*, 264(27):16174-82, 1989.

Thomson et al., "Embryonic Stem Cell Lines Derived fro Human Blastocysts", *Science*, 282:1145, 1998.

Vakkalanka, Sarah K. et al., "Temperature-and pH sensitive terpolymers for modulated delivery of streptokinase", *J. Biomater, Sci. Edn.*, 1996, vol. 8, No. 2, pp. 119-129.

Vernon, Brent, "Thermally Reversible Polymer Gels for Biohybrid Artifical Pancreas", *Macromo. Symp.*, 1996, vol. 109, pp. 155-167.

West et al., "Polymeric Biomaterials with Degradation Sites for Proteases Involved in Cell Migration", *Macromolecules*, 32:241-244, 1999.

Definition: bond, IUPAC Compendium of Chemical Terminology, 2nd Ed. (1997).

Definition: chemical bond, IUPAC Compendium of Chemical Terminology (2006).

* cited by examiner

HSF-6

Immunofluorescence—SSEA-4 (Day 5)

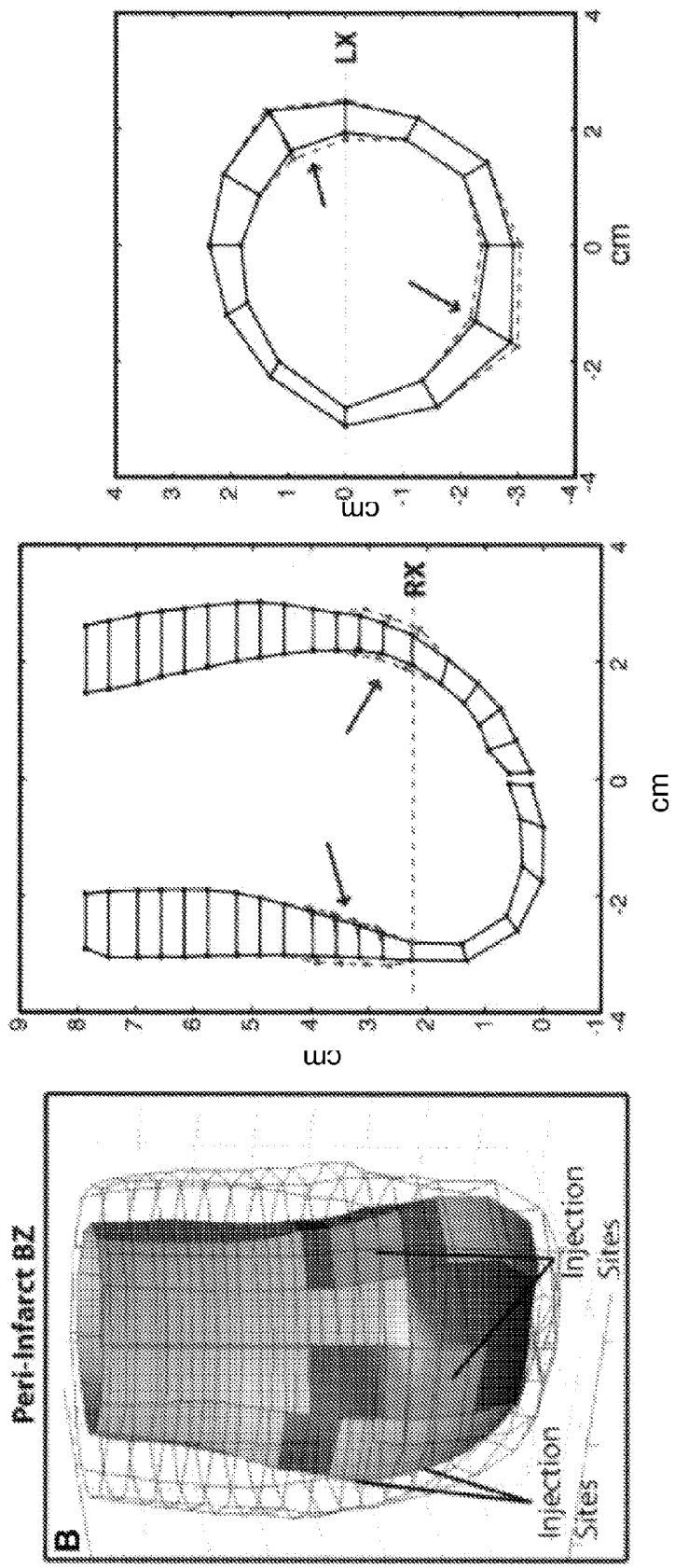

3% sIPN - 0 uM RGD, 14 days

3% sIPN - 100 uM RGD, 14 days

4% sIPN - 0 uM RGD, 14 days

4% sIPN - 100 uM RGD, 14 days

5% sIPN - 0 uM RGD, 14 days

5% sIPN - 100 uM RGD, 14 days

FIG. 29
FIG. 29A
FIG. 29B
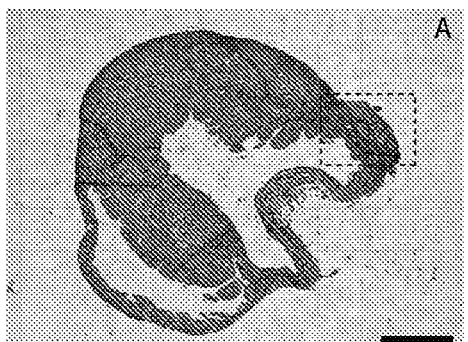
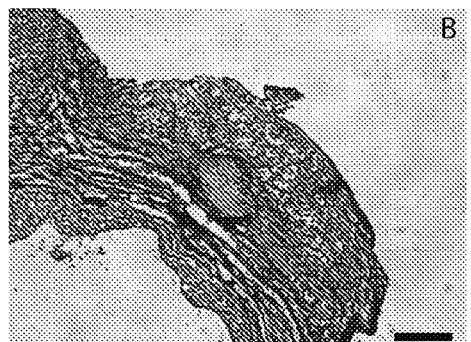
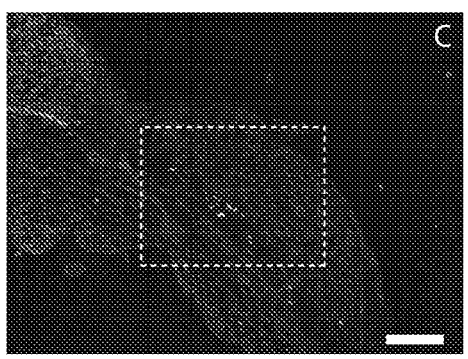
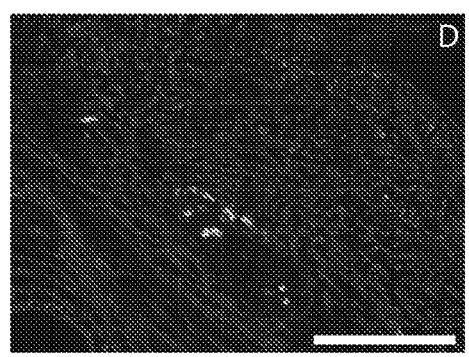
FIG. 29C
FIG. 29D

METHODS AND COMPOSITIONS FOR STABILIZING THE MYOCARDIUM

CROSS-REFERENCES TO RELATED APPLICATIONS

The present application claims the benefit of U.S. Provisional Patent Application No. 60/860,184, filed Nov. 20, 2006, and is a continuation-in-part of U.S. patent application Ser. No. 10/385,900, filed Mar. 10, 2003, which application claims the benefit of U.S. Provisional Patent Application No. 60/362,621, filed Mar. 8, 2002, and is a continuation-in-part of U.S. patent application Ser. No. 11/394,042, filed Mar. 29, 2006, which application claims the benefit of U.S. Provisional Patent Application No. 60/666,734, filed Mar. 29, 2005, the contents of each of which are incorporated herein by reference in their entirety for all purposes.

This invention was made with Government support under Grant Nos. AR047304, HL063348, and HL077921 awarded by the National Institutes of Health. The Government has certain rights to this invention.

FIELD OF THE INVENTION

The present invention relates generally to the field of treatment of cardiac conditions. More specifically, the present invention relates to the stabilization of the myocardium in the treatment of cardiac conditions.

BACKGROUND OF THE INVENTION

Congestive heart failure (CHF) occurs in over 5 million individuals in the United States today, and 500,000 additional cases are diagnosed each year. This condition is the leading cause for inpatient hospitalizations within the U.S. and is associated with high cardaic morbidity and mortality. (A. H. Assoc. (2006) *Heart and Stroke Statistical Update*: American Heart Association, Dallas, Tex.) CHF, systolic or diastolic, can result from a variety of structural or functional cardiac disorders or events that impair the heart's pump function. In ischemic heart disease, one of the major causes of CHF, necrotic myocyte death produces a vicious cycle of ventricular enlargement, increased myocyte fiber stress (particularly in the border zone) and eccentric myocyte hypertrophy (post-MI remodeling). Following an acute myocardial infarction (AMI), for example, necrotic tissue is replaced by fibrotic scar tissue to maintain the integrity of the ventricle, and, around this aneurysm, the infarct or a border zone (BZ) of hypocontractile and thinned myocardium develops and becomes subjected to substantially increased myocyte fiber stresses during the cardiac cycle. These increased stresses and abnormal strain on the region has been implicated in the pathological remodeling of the ventricle after an ischemic event, resulting in infarct extension and expansion and ultimately leading to congestive heart failure.

Attempts have also been made to address AMI injuries through various approaches. Drug therapy (ACE inhibitors and BETA blockers) has been shown to slow the remodeling that occurs after AMI, but has not been associated with return to normal left ventricular (LV) size and function. Solid organ cardiac transplantation is limited by donor shortage, and assist device therapy, although promising, is limited by persistent thrombotic events, infection, long-term materials compatibility, and the lack of an implantable power supply. Because of deficiencies in medical and standard surgical therapy for heart failure, innovative surgical procedures that reduce LV size or change LV shape are being investigated. Aneurysm repair, and radiofrequency infarct heating reduce LV volume, but LV function is either unchanged or mildly reduced. Partial left ventriculectomy reduces LV volume and wall stress, but significantly reduces LV function. Finally, passive cardiac constraint (Acorn cardiac support device, Acorn Cardiovascular) and shape change therapy with a novel tensioning device (Myosplint, Myocor) are promising, but seem unlikely to lead to large improvements in LV function.

Other approaches through tissue engineering and cell transplantation, with or without carrier matrices, into the infarct region have also been attempted to improve regional and global pump function, with mixed results. Survival of engraftment of the implanted cells has been poor and conclusive myocyte regeneration elusive despite demonstrated reduction in post-infarct loss of myocardial function with cellular and cellular/matrix injection. As such, there is a need for additional methods to stabilize the myocardium. The present invention provides compositions and methods useful in stabilizing the myocardium and mitigating function loss following ischemic injury to the heart.

Literature

1. R. A. Stile, W. R. Burghardt, and K. E. Healy, "Synthesis and characterization of injectable poly(N-isopropylacrylamide)-based hydrogels that support tissue formation in vitro," *Macromolecules*, vol. 32, pp. 7370-7379, 1999
2. S. Kim and K. E. Healy, "Synthesis and characterization of injectable poly(N-isopropylacrylamide-co-acrylic acid) hydrogels with proteolytically degradable cross-links," *Biomacromolecules*, vol. 4, pp. 1214-1223, 2003
3. R. A. Stile and K. E. Healy, "Poly(N-isopropylacrylamide)-based semi-interpenetrating polymer networks for tissue engineering applications. 1. Effects of linear poly(acrylic acid) chains on phase behavior," *Biomacromolecules*, vol. 3, pp. 591-600, 2002.
4. R. Pola, L. E. Ling, M. Silver, M. J. Corbley, M. Kearney, R. B. Pepinsky, R. Shapiro, F. R. Taylor, D. P. Baker, T. Asahara, and J. M. Isner, "The morphogen Sonic hedgehog is an indirect angiogenic agent upregulating two families of angiogenic growth factors," *Nature Medicine*, vol. 7, pp. 706-711, 2001.
5. R. J. Batista, J. Verde, P. Nery, L. Bocchino, N. Takeshita, J. N. Bhayana, J. Bergsland, S. Graham, J. P. Houck, and T. A. Salerno, "Partial left ventriculectomy to treat end-stage heart disease," *Ann Thorac Surg*, vol. 64, pp. 634-8., 1997.
6. J. M Guccione, S. M. Moonly, A. W. Wallace, M. B. Ratcliffe, "Residual stress produced by ventricular volume reduction surgery has little effect on ventricular function and mechanics: A finite element model study," *Journal of Thoracic and Cardiovascular Surgery*, vol. 122, pp. 592-599, 2001
7. M. B. Ratcliffe, J. Hong, A. Salahieh, S. Ruch, and A. W. Wallace, "The effect of ventricular volume reduction surgery in the dilated, poorly contractile left ventricle: a simple finite element analysis," *J Thorac Cardiovasc Surg*, vol. 116, pp. 566-77., 1998.
8. H. N. Sabbah, V. G. Sharov, P. A. Chaudhry, G. Suzuki, A. Todor, and H. Morita, "Chronic therapy with the acorn cardiac support device in dogs with chronic heart failure: three and six months hemodynamic, histologic and ultrastructural findings," *J Heart Lung Transplant*, vol. 20, pp. 189, 2001.
9. J. M Guccione, A Salahieh, S. M Moonly, J. Kortsmit, A. W. Wallace, M. B Ratcliffe, "Myosplint decreases wall 9. stress depressing function in the failing heart: A finite element model study" *Ann Thorac Surg*, vol. 76, pp. 1171-80, 2003
10. B. M. Jackson, J. H. Gorman, S. L. Moainie, T. S. Guy, N. Narula, J. Narula, M. G. John-Sutton, L. H. Edmunds, Jr., and R. C. Gorman, "Extension of borderzone myocardium in postinfarction dilated cardiomyopathy," *J Am Coll Cardiol*, vol. 40, pp. 1160-7; discussion 1168-71, 2002.
11. M. J. Moulton, S. W. Downing, L. L. Creswell, D. S. Fishman, D. M. Amsterdam, B. A. Szabo, J. L. Cox, and M. K. Pasque, "Mechanical dysfunction in the border zone of an ovine model of left ventricular aneurysm," *Ann Thorac Surg*, vol. 60, pp. 986-97; discussion 998, 1995.
12. J. M. Guccione, S. M. Moonly, P. Moustakidis, K. D. Costa, M. J. Moulton, M. B. Ratcliffe, and M. K. Pasque, "Mechanism Underlying Mechanical Dysfunction in the Border Zone of Left Ventricular Aneurysm: A Finite Element Model Study," *Ann. Thorac. Surg*, vol. 71 pp 654-62, 2001
13. D. Orlic, J. Kajstura, S. Chimenti, I. Jakoniuk, S. M. Anderson, B. S. Li, J. Pickel, R. McKay, B. Nadal-Ginard, D. M. Bodine, A. Leri, and P. Anversa, "Bone marrow cells regenerate infarcted myocardium," *Nature*, vol. 410, pp. 701-705, 2001.
14. J. M. Guccione, K. D. Costa, A. D. McCulloch, "Finite element stress analysis of left ventricular mechanics in the beating dog heart," *J Biomechanics*, vol. 28, pp. 1167-1177, 1995
15. J. H. Omens, K. D. May, A. D. McCulloch, "Transmural distribution of three-dimensional strain in the isolated arrested canine left ventricle," *Am J Physiol*, vol. 261, pp. H918-28. 1991
16. J. M. Guccione, A. D. McCulloch, L. K. Waldman, "Passive material properties of intact ventricular myocardium determined from a cylindrical model" *J Biomech Eng*, vol. 113 pp. 42-55, 1991
17. J. M. Gucionne, L. K. Waldman, A. D McCulloch, "Mechanics of active contraction in cardiac muscle: Part II—Cylindrical models of the systolic left ventricle," *J Biomech Eng*, vol. 115, pp. 82-90, 1993
18. Heart and Stroke Statistical Update: American Heart Association, Dallas; 2005.
19. Atkins B Z, Hueman M T, Meuchel J. Hutcheson K A, Glower D D, Taylor D A. Cellular cardiomyoplasty improves diastolic properties of injured heart. Journal Of Surgical Research 1999; 85(2):234-242.
20. Tomita G. Mickle D A G, Weisel R D, Jia Z C, Tumiati L C, Allidina Y. Liu P. Li R K. Improved heart function with myogenesis and angiogenesis after autologous porcine bone marrow stromal cell transplantation. Journal of Thoracic and Cardiovascular Surgery 2002; 123(6): 1132-1140.
21. Strauer B E, Brehm M. Zeus T, Kostering M. Hernandez A, Sorg R V, Kogler G, Wernet P. Repair of infarcted myocardium by autologous intracoronary mononuclear bone marrow cell transplantation in humans. Circulation 2002; 106(15):1913-1918.
22. Kawamoto A, Tkebuchava T. Yamaguchi J I, Nishimura H. Yoon Y S, Milliken C. Uchida S. Masuo 0, lwaguro H. Ma H. Hanley A, Silver M, Kearney M. Losordo D. lsner J, Asahara T. Intramyocardial transplantation of autologous endothelial progenitor cells for therapeutic neovascularization of myocardial ischemia. Circulation 2003; 107(3):461-468.
23. Kofidis T, Lebl D R, Martinez E C, Hoyt G, Tanaka M, Robbins R C. Novel injectable bioartificial tissue facilitates targeted, less invasive, large-scale tissue restoration on the beating heart after myocardial injury. Circulation 2005; 112(9):1173-1177.
24. Christman K L, Fok H H, Sievers R E, Fang Q H, Lee R J. Fibrin glue alone and skeletal myoblasts in a fibrin scaffold preserve cardiac function after myocardial infarction. Tissue Engineering 2004; 10(34):403-409.
25. Fuchs S, Baffour R, Zhou Y F, Shou M, Pierre A, Tio F O, Weissman N J, Leon M B, Epstein S E, Kornowski R. Transendocardial delivery of autologous bone marrow enhances collateral perfusion and regional function in pigs with chronic experimental myocardial ischemia. Journal of the American College of Cardiology 2001; 37(6):1726-1732.
26. Mangi A A, Noiseux N. Kong D L, He H M, Rezvani M, Ingwall J S, Dzau V J. Mesenchymal stem cells modified with Akt prevent remodeling and restore performance of infarcted hearts. Nature Medicine 2003; 9(9): 1195-1201.
27. Grossman W, Jones D. McLaurin L P. Wall Stress And Patterns Of Hypertrophy In Human Left-Ventricle. Journal Of Clinical Investigation 1975; 56(1):56-64.
28. Costa K D, Hunter P J, Wayne J S, Waldman L K, Guccione J M, McCulloch A D. A three-dimensional finite element method for large elastic deformations of ventricular myocardium.2. Prolate spheroidal coordinates. Journal Of Biomechanical Engineering-Transactions Of The Asme 1996; 118(4):464-472.
29. Guccione J M, Costa K D, McCulloch A D. Finite-Element Stress-Analysis Of Left-Ventricular Mechanics In The Beating Dog Heart. Journal Of Biomechanics 1995; 28(10):1167-1177.
30. Walker J C, Ratcliffe M B, Zhang P. Wallace A W, Fata B. Hsu E W, Saloner D. Guccione J M. MRI-based finite-element analysis of left ventricular aneurysm. American Journal Of Physiology-Heart And Circulatory Physiology 2005; 289(2):H692-H700.
31. Urech L. Bittermann A G, Hubbell J A, Hall H. Mechanical properties, proteolytic degradability and biological modifications affect angiogen) c process extension into native and modified fibrin matrices in vitro. Biomaterials 2005; 26(12):1369-1379.
32. Semler E J, Ranucci C S, Moghe P V. Mechanochemical manipulation of he aggregation can selectively induce or repress liver-specific function. Biotechnology And Bioengineering 2000; 69(4):359-369.
33. Barocas V H, Moon A G, Tranquillo R T. The Fibroblast-Populated Collagen Microsphere Assay Of Cell Traction Force.2. Measurement Of The Cell Traction Parameter. Journal Of Biomechanical Engineering-Transactions Of The Asme 1995; 117(2): 161-170.
34. Stile R A, Chung E. Burghardt W R, Healy K E. Poly (N-isopropylacrylamidey based semi-interpenetrating polymer networks for tissue engineering applications. Effects of linear poly(acrylic acid) chains on rheology. Journal of Biomaterials Science-Polymer Edition 2004; 15(7):865-878.
35. Kim G. Healy K E. Synthesis and characterization of injectable poly(Nisopropylacrylamide-co-acrylic acid) hydrogels with proteolytically degradable cross-links. Biomacromolecules 2003; 4(5):1214-1223.
36. Stokke B T, Draget K I, Smidsrod 0, Yuguchi Y, Urakawa H. Kajiwara K. Small-angle X-ray scattering and rheological characterization of alginate gels. 1. Ca-alginate gels. Macromolecules 2000; 33(5): 1853-1863.

37. Rizzi S C, Hubbell J A. Recombinant protein-co-PEG networks as cell-adhesive and proteolytically degradable hydrogel matrixes. Part 1: Development and physicochemical characteristics. Biomacromolecules 2005; 6(3):1226-1238.
38. He K L, Yi G H, Sherman W, Zhou H. Zhang G P, Gu A. Kao R. Haimes H B, Harvey J. Roos E. White D. Taylor D A, Wang J. Burkhoff D. Autologous skeletal myoblast transplantation improved hemodynamics and left ventricular function in chronic heart failure dogs. Journal Of Heart And Lung Transplantation 2005; 24(11):1940-1949.
39. Wollert, K. C., Meyer, G P, Lotz, J., Ringes-Lichtenberg S, Lippolt P. Breidenbach C. Fichtner S, Korte T, Hornig B. Messinger D. Arseniev L. Hertenstein B. Ganser A, Drexler H. Intracoronary autologous bone-marrow cell transfer after myocardial infarction: the BOOST randomised controlled clinical trial. Lancet 2004; 364(9429):141-148.
40. Meyer G P, Wollert K C, Lotz J. Steffens J. Lippolt P. Fichtner G. Hecker H. Schaefer A, Arseniev L. Hertenstein B. Ganser A, Drexler H. Intracoronary bone marrow cell transfer after myocardial infarction—Eighteen months' follow-up data from the randomized, controlled BOOST (BOne marrOw transfer to enhance ST-elevation infarct regeneration) trial. Circulation 2006; 113 (10):1287-1294.
41. van Oosterhout M F M, Arts T, Muijtjens A M M, Reneman R S, Prinzen F W. Remodeling by ventricular pacing in hypertrophying dog hearts. Cardiovascular Research 2001; 49(4):771-778.
42. Jackson B M, Gorman J H, Salgo I S, Moainie S L, Plappert T, St John-Sutton M. Edmunds L H, Gorman R C. Border zone geometry increases wall stress after myocardial infarction: contrast echocardiographic assessment. American Journal Of Physiology-Heart And Circulatory Physiology 2003; 284(2):H475-H479.
43. Moulton M J, Downing S W, Creswell L L, Fishman D S, Amsterdam D M, Szabo B A, Cox J L, Pasque M K. Mechanical Dysfunction In The Border Zone Of An Ovine Model Of Left-Ventricular Aneurysm. Annals Of Thoracic Surgery 1995; 60(4):986-998.
44. Orlic D, Kajstura J, Chimenti S, Limana F. Jakoniuk I, Quaini F. Nadal-Ginard B. Bodine D M, Led A. Anversa P. Mobilized bone marrow cells repair the infarcted heart, improving function and survival. Proceedings of the National Academy of Sciences of the United States of America 2001; 98(18):10344-10349.
45. Ratcliffe M B, Hong J. Salahieh A. Ruch G. Wallace A W. The effect of ventricular volume reduction surgery in the dilated, poorly contractile left ventricle: A simple finite element analysis. Journal Of Thoracic And Cardiovascular Surgery 1998; 116(4):566-577.
46. Dickstein M L, Spotnitz H M, Rose E A, Burkhoff D. Heart reduction surgery: An analysis of the impact on cardiac function. Journal Of Thoracic And Cardiovascular Surgery 1997; 113 (6):1032-1040.

BRIEF SUMMARY OF THE INVENTION

The present invention provides methods and compositions for stabilizing the myocardium and treating individuals with cardiac conditions such as dilated cardiomyopathy, myocardial infarction, and congestive heart failure. In particular, the invention provides compositions that can be applied to form a prosthetic structure in situ and/or to serve as an extracellular matrix (ECM) for cardiac tissue engineering. These compositions have the ability to stabilize the myocardium with or without the addition of transplant cells, e.g. bone marrow derived mesenchymal stem cells (BMSCs), skeletal myoblasts, endothelial precursor cells, embryonic stem cells, etc. by providing one or more of the following: a) biomechanical stabilization of an injured or defective myocardial wall; b) increase in wall thickness; c) stabilization of the left ventricle (LV) size; d) promotion of infiltration of local and viable cells into the structure that formed in situ; e) reduction of fiber stresses; f) inhibition of infarct extension; g) amelioration of the remodeling process; h) improved ventricular function; i) preservation of myocardial cells in infarct region of the heart; or j) reduction in progression toward congestive heart failure (CHF).

The present invention also provides enhanced methods to facilitate the delivery and survival of transplant cells in the myocardium. Finite element modeling methods described herein can be used to accurately estimate the acute ventricular mechanical effects of implant cells and materials and thereby allow for tuning of parameters, such as stiffness, volume, and positioning, etc., of the present compositions to account for conditions in the local environment as determined from MRI data.

Other aspects, objects, and advantages of the present invention will be apparent to those of ordinary skill in the art from the following detailed disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended Figures. These Figures form a part of the specification. It is to be noted, however, that the appended Figures illustrate preferred embodiments of the invention and therefore are not to be considered limiting in their scope.

FIG. 13 is a depiction of mesh changes to model in three performed simulations. FIG. 13B. Multiple peri-infarct border zone injections.

FIG. 14 Calculated local stress response to injection volume and material stiffness.

FIG. 25 FIG. 25A provides photomicrographs of sIPN conditions in 3D cultures after 14 days. Low modulus-RGD conditions show growing clusters of multiple cells (top left), while cell spreading can be seen in the high modulus, high RGD condition (bottom right).

FIG. 29 shows the localization of injected sIPN and present GFP cells at t=6 weeks according to an exemplary embodiment of the invention. In FIG. 29A, the trichrome stained ventricle indicates the region of injection and generated infarct. FIG. 29B shows the high magnification region of injection from FIG. 29A (dashed box), revealing degraded and remodeled hydrogel. FIG. 29C provides a fluorescent image of the same region as indicating presence of GFP positive cells. FIG. 29D shows the higher magnification image of box of interest in FIG. 29C (dashed box), showing presence of GFP cells.

DETAILED DESCRIPTION OF THE INVENTION

Abbreviations and Definitions

Figure 1A:
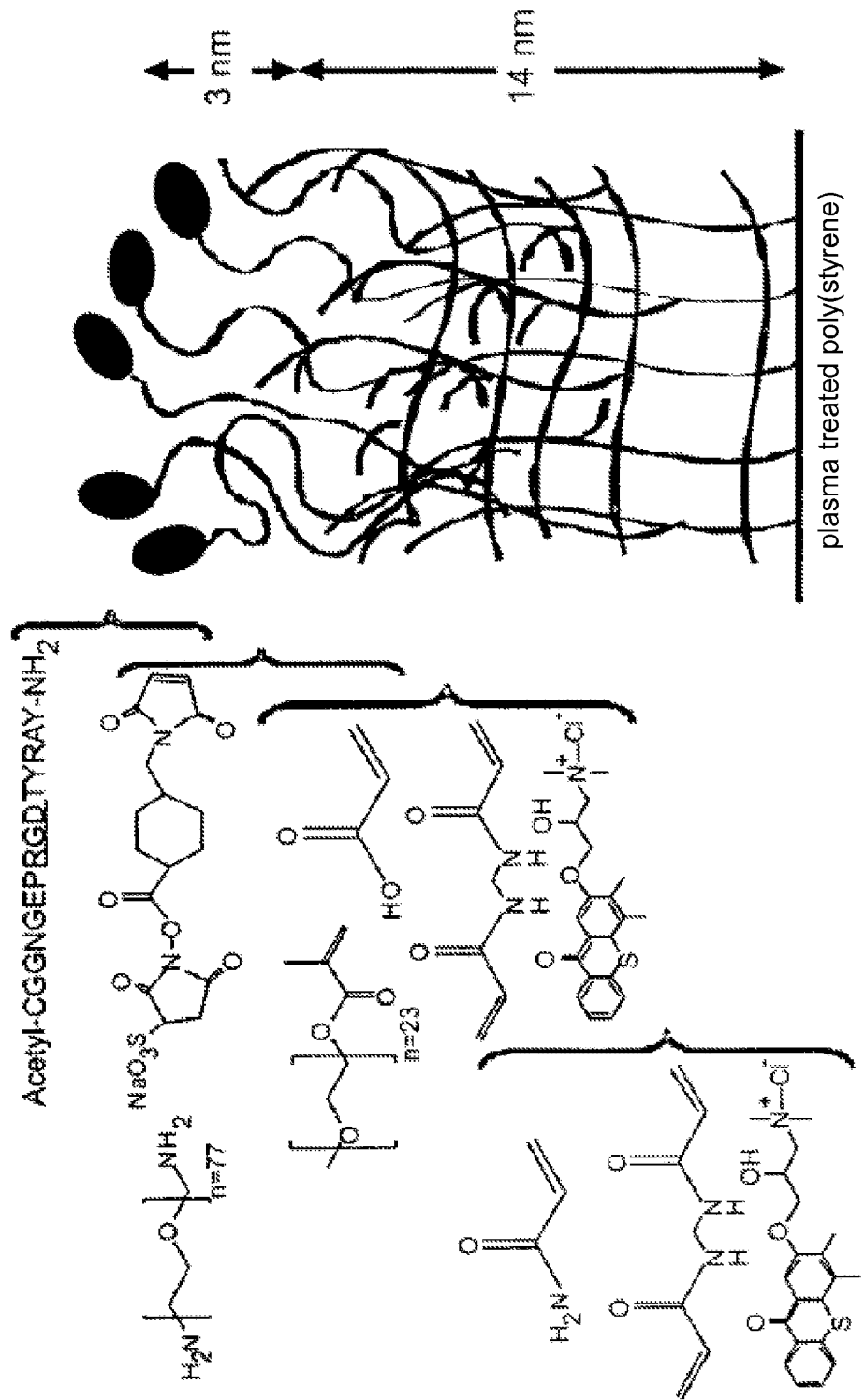
FIG. 1. Diagram and Characterization of IPN. a) Schematic of interpenetrating polymer network (IPN) synthesis (not to scale). Sequential polymerization steps create an IPN that is swollen in aqueous media and conjugated to bioactive peptides. b) & c) Representative results showing the thickness as well as the shear, loss, and complex shear moduli (G', G", and |G*| respectively, where $G^* = G' + iG''$) from the Kelvin-Voigt modeling of the PBS swelling of the hydrogel. The initial hydration of the hydrogel surface from the dry state is shown, as well as swelling of the surface. Zero modulus represents the unmodified substrate. There was an increase in thickness and a decrease in all moduli for all surfaces with swelling. Note that the dry characteristics of the IPN are as follows: XPS peak intensity ratios (i.e., O/N and C/N) indicated IPN coating of the poly(styrene) substrate, while angle-resolved studies demonstrated that the pAAm and PEG/AAc networks were interpenetrating with a dry thickness of ~3.5-4.4 nm. The dry thickness in ambient humidity (~5 nm in 49±7% relative humidity) was slightly larger than that determined by angle-resolved XPS (data not shown). d) Ligand density data (mean±s.d.) for bsp-RGD(15)-FITC: Data representing input concentrations from 0.0046 to 0.46 µM with respective densities of ≈0.5 to 18 pmol/cm².

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

As used herein, "NIPAAm," refers to "N-isopropylacrylamide." The term "p(NIPAAm)," as used herein, refers to "poly(N-isopropylacrylamide)." As used herein, "BIS," refers to "N,N'-methylenebisacrylamide." The term, "AAc," as used herein, refers to "acrylic acid." The term, "p(AAC)," as used herein, refers to linear "poly(acrylic acid)" chains. The term, "p(NIPAAm-co-AAc)," as used herein, refers to a sIPN formed from poly(N-isopropylacrylamide) and a linear poly(acrylic acid). "AP," as used herein, refers to "ammonium peroxydisulfate." "TEMED," as used herein, refers to "N,N, N',N'-tetramethylethylenediamine." "ECM," as used herein, refers to "extracellular matrix." The term "sIPN," as used herein, refers to "semi-interpenetrating polymer network." "IPN," refers to an "inter-penetrating polymer network." The term "EMCH," as used herein, refers to "N-ε-(maleimidocaproic acid)hydrazide." The term "RGD peptide" refers to a peptide that includes the three amino acid motif RGD.

"Peptide" refers to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. In addition, other peptidomimetics are also useful in the present invention. As used herein, "peptide" refers to both glycosylated and unglycosylated peptides. Also included are petides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

"Antibody," as used herein, generally refers to a polypeptide comprising a framework region from an immunoglobulin or fragments or immunoconjugates thereof that specifically binds and recognizes an antigen. The recognized immunoglobulins include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering" means oral administration, administration as a suppository, topical contact, intravenous, intraperitoneal, intramuscular, intralesional, intranasal or subcutaneous administration, or the implantation of a slow-release device e.g., a mini-osmotic pump, to the subject.

As used herein, the term "copolymer" describes a polymer which contains more than one type of subunit. The term encompasses polymer which include two, three, four, five, or six types of subunits.

As used herein, the term "essentially constant" refers to a second value which has only a small difference between a first, originally measured value. For example, a biochemical property, such as ligand density, is essentially constant between two sIPNs if the difference between the ligand density values in these sIPNs is 5% or less.

The term "isolated" refers to a material that is substantially or essentially free from components, which are used to produce the material. The lower end of the range of purity for the polymer networks is about 60%, about 70% or about 80% and the upper end of the range of purity is about 70%, about 80%, about 90% or more than about 90%.

"Hydrogel" refers to a water-insoluble and water-swellable cross-linked polymer that is capable of absorbing at least 3 times, preferably at least 10 times, its own weight of a liquid. "Hydrogel" and "thermo-responsive polymer" are used interchangeably herein.

The term "attached," as used herein encompasses interaction including, but not limited to, covalent bonding, ionic bonding, chemisorption, physisorption and combinations thereof.

The term "biomolecule" or "bioorganic molecule" refers to an organic molecule typically made by living organisms. This includes, for example, molecules comprising nucleotides, amino acids, sugars, fatty acids, steroids, nucleic acids, polypeptides, peptides, peptide fragments, carbohydrates, lipids, and combinations of these (e.g., glycoproteins, ribonucleoproteins, lipoproteins, or the like).

"RGD" peptides refer to peptides containing the arginine-glycine-aspartate (RGD) motif modulate cell adhesion.

"Small molecule," refers to species that are less than 1 kD in molecular weight, preferably, less than 600 D.

The term "autologous cells", as used herein, refers to cells which are person's own genetically identical cells.

The term "heterologous cells", as used herein, refers to cells which are not person's own and are genetically different cells.

The term "network", as used herein, refers to an interpenetrating polymer network (IPN), a semi-interpenetrating polymer network (sIPN), or both. These IPNs and sIPNs are functionalized with a ligand as described herein.

"Extracellular matrix" or "matrix" refers to one or more substances that provide substantially the same conditions for supporting cell growth as provided by an extracellular matrix synthesized by feeder cells. The matrix may be provided on a substrate. Alternatively, the component(s) comprising the matrix may be provided in solution. Components of an extracellular matrix can include laminin, collagen and fibronectin.

The term "stem cells", as used herein, refers to cells capable of differentiation into other cell types, including those having a particular, specialized function (i.e., terminally differentiated cells, such as erythrocytes, macrophages, etc.). Stem cells can be defined according to their source (adult/somatic stem cells, embryonic stem cells), or according to their potency (totipotent, pluripotent, multipotent and unipotent).

The term "unipotent", as used herein, refers to cells that can produce only one cell type, but have the property of self-renewal which distinguishes them from non-stem cells.

The term, "multipotent", or "progenitor", as used herein, refers to cells which can give rise to any one of several different terminally differentiated cell types. These different cell types are usually closely related (e.g. blood cells such as red blood cells, white blood cells and platelets). For example, mesenchymal stem cells (also known as marrow stromal cells) are multipotent cells, and are capable of forming osteoblasts, chondrocytes, myocytes, adipocytes, neuronal cells, and β-pancreatic islets cells.

The term "pluripotent", as used herein, refers to cells that give rise to some or many, but not all, of the cell types of an organism. Pluripotent stem cells are able to differentiate into any cell type in the body of a mature organism, although without reprogramming they are unable to de-differentiate into the cells from which they were derived. As will be appreciated, "multipotent"/progenitor cells (e.g., neural stem cells) have a more narrow differentiation potential than do pluripotent stem cells. Another class of cells even more primitive (i.e., uncommitted to a particular differentiation fate) than pluripotent stem cells are the so-called "totipotent" stem cells.

The term "totipotent", as used herein, refers to fertilized oocytes, as well as cells produced by the first few divisions of the fertilized egg cell (e.g., embryos at the two and four cell stages of development). Totipotent cells have the ability to differentiate into any type of cell of the particular species. For example, a single totipotent stem cell could give rise to a complete animal, as well as to any of the myriad of cell types found in the particular species (e.g., humans). In this specification, pluripotent and totipotent cells, as well as cells with the potential for differentiation into a complete organ or tissue, are referred as "primordial" stem cells.

The term "dedifferentiation", as used herein, refers to the return of a cell to a less specialized state. After dedifferentiation, such a cell will have the capacity to differentiate into more or different cell types than was possible prior to re-programming. The process of reverse differentiation (i.e., de-differentiation) is likely more complicated than differentiation and requires "re-programming" the cell to become more primitive. An example of dedifferentiation is the conversion of a myogenic progenitor cell, such as early primary myoblast, to a muscle stem cell or satellite cell.

The term "anti-aging environment", as used herein, is an environment which will cause a cell to dedifferentiate, or to maintain its current state of differentiation. For example, in an anti-aging environment, a myogenic progenitor cell would either maintain its current state of differentiation, or it would dedifferentiate into a satellite cell.

A "normal" stem cell refers to a stem cell (or its progeny) that does not exhibit an aberrant phenotype or have an aberrant genotype, and thus can give rise to the full range of cells that be derived from such a stem cell. In the context of a totipotent stem cell, for example, the cell could give rise to, for example, an entire, normal animal that is healthy. In contrast, an "abnormal" stem cell refers to a stem cell that is not normal, due, for example, to one or more mutations or genetic modifications or pathogens. Thus, abnormal stem cells differ from normal stem cells.

A "growth environment" is an environment in which stem cells will proliferate in vitro. Features of the environment include the medium in which the cells are cultured, and a supporting structure (such as a substrate on a solid surface) if present.

"Growth factor" refers to a substance that is effective to promote the growth of stem cells and which, unless added to the culture medium as a supplement, is not otherwise a component of the basal medium. Put another way, a growth factor is a molecule that is not secreted by cells being cultured (including any feeder cells, if present) or, if secreted by cells in the culture medium, is not secreted in an amount sufficient to achieve the result obtained by adding the growth factor exogenously. Growth factors include, but are not limited to, basic fibroblast growth factor (bFGF), acidic fibroblast growth factor (aFGF), epidermal growth factor (EGF), insulin-like growth factor-I (IGF-I), insulin-like growth factor-II (IGF-II), platelet-derived growth factor-AB (PDGF), and vascular endothelial cell growth factor (VEGF), activin-A, and bone morphogenic proteins (BMPs), insulin, cytokines, chemokines, morphogents, neutralizing antibodies, other proteins, and small molecules.

The term "differentiation factor", as used herein, refers to a molecule that induces a stem cell to commit to a particular specialized cell type.

The term "regenerative capacity", as used herein, refers to conversion of stem cell into dividing progenitor cell and differentiated tissue-specific cell.

The term, "self renewal", as used herein, refers to proliferation without lineage specification.

The term, "bsp-RGD(15)", as used herein, refers to the following 15-mer bone sialopeptide sequence: CGGNGEPRGDTYRAY (SEQ ID NO: 1).

The term, "bsp-RGD(15)-FITC", as used herein, refers to the following bone sialopeptide sequence: CGGNGEPRGD-TYRAYK(FITC) GG (SEQ ID NO: 2), wherein FITC refers to.

The term, "bsp-RGE(15)", as used herein, refers to the following nonsense 15-mer bone sialopeptide sequence: CGGNGEPRGETYRAY (SEQ ID NO: 3).

The term "biomolecule" or "bioorganic molecule" refers to an organic molecule typically made by living organisms. This includes, for example, molecules comprising nucleotides, amino acids, sugars, fatty acids, steroids, nucleic acids, polypeptides, peptides, peptide fragments, carbohydrates, lipids, and combinations of these (e.g., glycoproteins, ribonucleoproteins, lipoproteins, or the like).

The term, "stabilizing the myocardium," as used herein, refers generally to normalizing the structural and mechanical properties of the myocardium. Stabilizing the myocardium can involve achieving one or more of the following: a) biomechanical stabilization of an injured or defective myocardial wall; b) increase in wall thickness; c) stabilization of the left ventricle (LV) size; d) promotion of infiltration of local and viable cells into the structure that formed in situ; e) reduction of fiber stresses; f) inhibition of infarct extension; g) amelioration of the remodeling process; h) improved ventricular function; i) preservation of myocardial cells in infarct region of the heart; or j) reduction in progression toward congestive heart failure (CHF).

The term, "apply" or "applying" a material, as used herein, refers generally to laying or placing the material and includes all methods known in the art, including without limitation, injecting, depositing, implanting, and swabbing.

By "transplanted cell" is meant a cell which has been introduced into a host so as to be in contact with a cell within a host. For example, a recombinant cell or cells may be grafted and/or implanted into the cardiac tissue of a host.

By "therapeutically effective amount" in the context of stabilizing the myocardium is meant an amount effective to achieve one or more of the following: a) biomechanical stabilization of an injured or defective myocardial wall; b) increase in wall thickness; c) stabilization of the left ventricle (LV) size; d) promotion of infiltration of local and viable cells into the structure that formed in situ; e) reduction of fiber stresses; f) inhibition of infarct extension; g) amelioration of the remodeling process; h) improved ventricular function; i) preservation of myocardial cells in infarct region of the heart; or j) reduction in progression toward congestive heart failure (CHF).

The terms "subject", "patient", "host" and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

By "treatment", "treating", or "treat" is meant that at least an amelioraton of the symptoms associated with the condition afflicting the host is achieved, where amelioration is used in a broad sense to refer to at least a reduction in the magnitude of a parameter, e.g. symptom (such as ejection fraction, Starling relationship, regional ventricular wall strains, infarct extension, expansion of the border zone wall, border zone stress amplitude) associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

II Introduction

The present invention provides methods and compositions for stabilizing the myocardium and preventing progression towards CHF, as will be detailed in the following description.

Myocardial Stabilization

Compositions of the invention can be applied to myocardial tissue to form a prosthetic structure in situ that can also serve a dual function as an extracellular matrix for cardiac tissue engineering. In preferred embodiments, the compositions are applied to the myocardium soon after the ischemic event, e.g. acute myocardial infarction. Most preferably, the patient is treated within five days after AMI. The myocardium is stabilized with application of the disclosed compositions by affecting general myocardial and ventricle geometry and mechanics, preserving myocardial cells in infarct region, promoting infiltration of local and viable cells into the structure to facilitate the regenerative process, and supporting the survival of transplant cells. More specifically, the present invention provides for one or more of the following: a) biomechanical stabilization of an injured or defective myocardial wall; b) increase in wall thickness; c) stabilization of the left ventricle (LV) size; d) promotion of infiltration of local and viable cells into the structure that formed in situ; e) reduction of fiber stresses; f) inhibition of infarct extension; g) amelioration of the remodeling process; h) improved ventricular function; i) preservation of myocardial cells in infarct region of the heart; or j) reduction in progression toward congestive heart failure (CHF).

As will be understood from the instant disclosure, the prosthetic structures and/or extracellular matrices described above can be further functionalized with ligands, e.g. angiogenic agents such as Sonic Hedgehog, growth factors, cell adhesion motifs, cell signaling agents such as cytokines, etc. to enhance the regenerative process, promote angiogenesis, or effect cytokine-mediated reduction of apoptosis.

Compositions

With guidance from the present disclosure, various materials known in the art can be used, alone or in combination, with the methods described herein. In preferred embodiments, a physiologically acceptable material capable of direct application to myocardial tissue is employed. In some embodiments, a contractile material is used. In other preferred embodiments, a non-contractile material is used. Such compositions include, without limitation, fibrin glue and other polymer agents capable of setting and integrating with the myocardium structure to form a prosthetic in situ. These compositions can be directly applied to the myocardial tissue or as a precursor to the prosthetic material to be formed in situ. In some preferred embodiments, the physiologically acceptable material is a low modulus material that can be directly injected into the myocardium where it stiffens in situ and form a stress-bearing structure with material properties compatible with those of the native myocardium. In preferred embodiments, the range of modulus for supporting stress in the myocardium while still being injectable is approximately between about 100 Pa to about 2000 Pa.

Depending on the ductility of the polymer matrix, the materials described herein can range from being extremely rigid to soft and pliable. Practical considerations however dictate as rigid materials would need to be implanted surgically whereas more ductile or in situ forming prosthetic/matrix can be injected and thereby reduce the invasiveness of the implantation procedure. In instances where the material is surgically implanted, then a material with a greater range of moduli can be used, as readily appreciated by those of ordinary skill in the art. One class of materials which meet the requirements for injection are thermoresponsive hydrogels, such as polymers based around the monomer N-Isopropylacrylamide, which undergo a reversible phase change when brought from room temperature to 37° C., stiffening significantly from an injectable gel into a viscoelastic solid. In addition to being injectable and capable of undergoing a phase transition in situ, materials useful for this invention should be compatible with the host tissue in order to share the dynamic load during the cardiac cycle. Therefore, the use of ligand-functionalized materials which foster cellular engagement, such as those incorporating the arg-gly-asp (-RGD-) cellular peptide binding motif or other cellular binding signals or sites, offer particular advantages for the applications described herein. In alternative embodiments, the material may also contain drug or gene delivery vehicles, thus operating as both a mechanical and chemical therapeutic device.

Polymer mixtures that demonstrate lower critical phase separation are used in preferred embodiments of the present invention. For example, poly(N-isopropylacrylamide) [p(NIPAAm)] chains and cross-linked hydrogels exhibit unique phase properties in aqueous media when heated above the LCST, which is ~32° C. At temperatures below the LCST, p(NIPAAm) chains are soluble in water and cross-linked hydrogels swell, while at the LCST, the chains precipitate out of solution, and the hydrogels demonstrate a volume-phase transition, during which they collapse considerably, expel a large amount of pore water, and become stiff and opaque. This behavior is reversible and can be modified by polymerizing the NIPAAm monomer with more hydrophobic or more hydrophilic comonomers.

In order to induce interactions between a material and a biological system, the material is commonly modified with biologically active synthetic peptides containing sequences that interact with cell-surface receptors. The amino acid sequence -Arg-Gly-Asp-(RGD), a ubiquitous cell-binding domain found in many ECM proteins and recognized by cell-surface receptors called integrins, has been extensively studied as a means to manipulate cell-material interactions. Different integrins demonstrate different binding specificity to the RGD peptide sequence based on the amino acids flanking the attachment signal and the conformation of the protein. Thus, RGD-containing peptides of various lengths have been covalently grafted to 2D substratesor within 3D networks.

In preferred embodiments, injectable semi-interpenetrating polymer networks (sIPNs), comprised of poly(N-isopropylacrylamide-co-acrylic acid), p(NIPAAm-co-AAc), hydrogels with linear peptide-modified poly(acrylic acid), p(AAc), chains physically entangled within the network are used. These sIPNs were synthesized by first grafting RGD-containing peptides to the —COO⁻ groups on the linear polymer chains, and then simultaneously polymerizing and cross-linking NIPAAm and AAc in the presence of the peptide-functionalized p(AAc) chains. These p (NIPAAm-co-AAc) hydrogels had very low cross-link densities, which allowed the matrices to be injected through a small-diameter aperture at 22° C. (i.e., a 30 gauge needle). When heated to body temperature (i.e., 37° C.), the hydrogels demonstrated a significant increase in rigidity (i.e., complex shear modulus, G*), without exhibiting a change in the volume or water content of the matrix. Since the p(AAc) chains or other polymer chains are modified with peptides prior to the sIPN synthesis, the p(NIPAAm-co-AAc) hydrogel phase transition properties remain largely unaffected by the addition of the functionalized linear chains.

Protease-based Matrix Degradation. In preferred embodiments of the invention, the materials used are protease degradable. Greater control over material degradation, cell ingrowth, and tissue regeneration can be achieved with bio-adaptable matrices that are designed to respond to the presence of cells and molecules they synthesize (e.g., proteases). Thus, one can design for specific degradation of the matrix by including protease (e.g., matrix metalloproteinase (MMP) family) specific crosslinker chemistry into the sIPN hydrogel. MMP's are a structurally and functionally related family of zinc-dependent endopeptidases that cleave either one or several ECM proteins. More recently, variants of ECM analogs exploiting proteolytically degradable domains have been developed. Thus, the feasibility of protease degradation of oligopeptide crosslinked hydrogels has been demonstrated in vitro and in vivo. In some embodiments of the invention, sIPNs with peptide crosslinkers based on known cleavage sites for MMP-13, -9, and -2, since the temporal expression of MMP-1, -2, -3, -7, -9, -11, -12, -13, and -14 and their inhibitors, TIMP-1, -2, -3, and -4 are used as these MMPs are significantly upregulated during the first week post MI.

In vivo, these materials support regeneration of site specific tissue, such as bone marrow, and do not cause an adverse tissue reaction when injected into either the murine or ovine hearts. These studies confirmed the ability of the p(NIPAAm-co-AAc) hydrogels to promote the growth of mammalian cells and that they were not cytotoxic.

Exemplary materials of the invention are semi-interpenetrating polymer networks (sIPNs) and interpenetrating polymer networks (IPNs). The physical and chemical properties of sIPNs and IPNs (polymers which can contain a significant volume of water) are exploited to provide a prosthetic structure in the myocardium and/or to mimic the native matrix surrounding mammalian cells (extracellular matrix, ECM), which serve to lessen the fiber stresses in the heart and foster recapitulation of the regenerative process. Exemplary semi-interpenetrating polymer networks (sIPNs) are composed of a cross-linked polymer network with entangled linear polymer chains. sIPNs are of use in a number of applications, including solute delivery and molecular separations. Exemplary interpenetrating polymer networks (IPNs) are composed of two cross-linked polymer networks.

IPNs

In a first aspect, the invention provides a network which is an interpenetrating polymer network. The interpenetrating polymer network includes (a) a first cross-linked polymer; and (b) a second cross-linked polymer. Covalently grafted to the first cross-linked polymer and/or the second cross-linked polymer is a ligand which affects the adhesion of the stem cell to the network or the growth or differentiation of a cell, e.g. cardiomyocytes and their progenitor cells derived from embryonic stem cells. Exemplary ligands of use in the invention, such as adhesion peptides, growth factors and differentiation factors, are defined herein.

The properties of the cross-linked polymers of the invention can be varied by choice of monomer(s), cross-linking agent and degree of polymer cross-linking. An exemplary variation in the monomer properties is hydrophobicity/hydrophilicity.

In general, providing larger hydrophobic moieties on a cross-linked polymer decreases water swellability. For example, hydrogels made of isopropyl acrylamide are water swellable and possess small hydrophobic moieties (i.e., an isopropyl group). The hydrophobic binding character of these gels is salt dependent. However, when the isopropyl group is replaced by a larger hydrophobic moiety, e.g., an octyl group, the gel loses some of its water swellability.

Exemplary hydrophilic moieties are derived from monomers that include N-methacryloyl-tris(hydroxymethyl)methylamine, hydroxyethyl acrylamide, hydroxypropyl methacrylamide, N-acrylamido-1-deoxysorbitol, hydroxyethylmethacrylate, hydroxypropylacrylate, hydroxyphenylmethacrylate, poly(ethylene glycol)monomethacrylate, poly(ethylene glycol) dimethacrylate, acrylamide, glycerol monomethacrylate, 2-hydroxypropyl acrylate, 4-hydroxybutyl methacrylate, 2-methacryloxyethyl glucoside, poly(ethyleneglycol) monomethyl ether monomethacrylate, vinyl 4-hydroxybutyl ether, and derivatives thereof.

Presently preferred hydrophilic moieties are derived from monomers that include a poly(oxyalkylene) group within their structure. Poly(ethylene glycol)-containing monomers are particularly preferred. PEG of any molecular weight, e.g., 100Da, 200Da, 250Da, 300Da, 350Da, 400Da, 500Da, 550Da, 600Da, 650Da, 700Da, 750Da, 800Da, 850Da, 900Da, 950Da, 1 kDa, 1500 Da, 2 kDa, 5 kDa, 10 kDa, 15 kDa, 20 kDa, 30 kDa and 40 kDa is of use in the present invention.

Presently preferred hydrophobic moieties are derived from acrylamide monomers in which the amine nitrogen of the amide group is substituted with one or more alkyl residues.

Exemplary hydrophobic moieties are derived from monomers selected from N-isopropylacrylamide, N,N-dimethylacrylamide, N,N-diethyl(meth)acrylamide, N-methyl methacrylamide, N-ethylmethacrylamide, N-propylacrylamide, N-butylacrylamide, N-octyl (meth)acrylamide, N-dodecylmethacrylamide, N-octadecylacrylamide, propyl(meth)acrylate, decyl(meth)acrylate, stearyl(meth)acrylate, octyl-triphenylmethylacrylamide, butyl-triphenylmethylacrylamide, octadedcyl-triphenylmethylacrylamide, phenyl-triphenylmethylacrlamide, benzyl-triphenylmethylacrylamide, and derivatives thereof.

An exemplary cross-linked polymer is a thermoresponsive polymer that changes from a first state to a second when the ambient temperature to which it is exposed is changed. Thus, in an exemplary embodiment, the invention utilizes a thermoresponsive polymer that becomes more rigid, and less flowable, generally more closely resembling an ECM, as it is heated. A preferred polymer changes state, becoming more rigid, within a temperature range that includes mammalian body temperatures, particularly 37° C.

In yet a further exemplary embodiment, the network includes a cross-linked polymer having a subunit derived from a synthetic polymer, peptide, nucleic acid and/or carbohydrate.

In an exemplary embodiment, the cross-linked polymer of the network comprises a subunit derived from N-isopropylacrylamide. In another exemplary embodiment, the cross-linked polymer is N-isopropylacrylamide.

Methods of Making the IPNs

Methods of making IPNs are known in the art. Examples of IPN synthesis are provided in the Examples section.

Cross-linking groups can be used to form the cross-links in either the IPNs or the sIPNs. The following discussion can also apply and to attach the method of attaching the ligand to the network. Thus, the discussion that follows is relevant to both types of cross-linking interactions: ligand cross-linking to the cross-linked or linear polymer; and cross-links within the thermo-responsive polymer.

Both the amount and the identity of the cross-linking agent used in the embodiments of the present invention are variable without limitation. For example, the amount of the cross-linking agent with respect to the polymerizable monomers can vary and it is well within the abilities of one of skill in the art to determine an appropriate amount of cross-linking agent to form an IPN or a sIPN having desired characteristics. In an exemplary embodiment, the cross-linking agent is used in an amount ranging preferably from 0.0001 weight parts to 10 weight parts, more preferably from 0.001 weight parts to 5 weight parts, most preferably from 0.01 weight parts to 2 weight parts, based on 100 parts by weight of either the hydrophobic or hydrophilic monomer.

Exemplary bifunctional compounds which can be used in the present invention include, but are not limited to, bifunctional poly(ethyleneglycols), polyamides, polyethers, polyesters and the like. General approaches for cross-linking two components are known in the literature. See, for example, Lee et al., *Biochemistry* 28: 1856 (1989); Bhatia et al., *Anal. Biochem.* 178: 408 (1989); Janda et al *J. Am. Chem. Soc.* 112: 8886 (1990) and Bednarski et al., WO 92/18135. In the discussion that follows, the reactive groups are discussed as components of the linear polymer. The focus of the discussion is for clarity of illustration. Those of skill in the art will appreciate that the discussion is relevant to reactive groups on the ligand as well.

In an exemplary strategy for species that contain thiol groups (e.g., proteins or synthetic peptides containing cysteine residues), the —SH groups are grafted to the —COO⁻ groups of, e.g., the p(AAc) chains using the cross-linker N-ϵ-(maleimidocaproic acid) hydrazide (EMCH; Pierce, Rockford, Ill.). The hydrazide end of EMCH is first reacted with the —COO⁻ groups in the p(AAc) chains using a dehydation agent such as, 1-ethyl-3-(3-dimethylaminopropyl) carbodiimide in the presence of N-hydroxysulfosuccinimide in 2-(N-morpholino) ethanesulfonic acid. The unreacted components are removed via dialysis, the product is lyophylized, and then the maleimide end of EMCH is reacted with the SH groups of the biomolecule in sodium phosphate buffer (pH 6.6).

Another exemplary strategy involves incorporation of a protected sulfhydryl onto the polymer chain using the heterobifunctional crosslinker SPDP (n-succinimidyl-3-(2-pyridyldithio)propionate and then deprotecting the sulfhydryl for formation of a disulfide bond with another sulfhydryl on the modifying group.

If SPDP detrimentally affects the properties of the linear polymer, there is an array of other crosslinkers such as 2-iminothiolane or N-succinimidyl S-acetylthioacetate (SATA), available for forming disulfide bonds. 2-iminothiolane reacts with primary amines, instantly incorporating an unprotected sulfhydryl onto the amine-containing molecule. SATA also reacts with primary amines, but incorporates a protected sulfhydryl, which is later deacetaylated using hydroxylamine to produce a free sulfhydryl. In each case, the incorporated sulfhydryl is free to react with other sulfhydryls or protected sulfhydryl, like SPDP, forming the required disulfide bond.

The above-described strategies are exemplary, and not limiting, of linkers of use in the invention. Other crosslinkers are available that can be used in different strategies for crosslinking the modifying group to the peptide. For example, TPCH (S-(2-thiopyridyl)-L-cysteine hydrazide and TPMPH ((S-(2-thiopyridyl) mercapto-propionohydrazide) react with aldehydes, thus forming a hydrazone bond between the hydrazide portion of the crosslinker and the periodate generated aldehydes. TPCH and TPMPH introduce a 2-pyridylthione protected sulfhydryl group onto a species, which can be deprotected with DTT and then subsequently used for conjugation, such as forming disulfide bonds between components.

If disulfide bonding is found unsuitable for producing stable networks, other crosslinkers may be used that incorporate more stable bonds between components. The heterobifunctional crosslinkers GMBS (N-gama-malimidobutyryloxy)succinimide) and SMCC (succinimidyl 4-(N-maleimido-methyl)cyclohexane) react with primary amines, thus introducing a maleimide group onto the component. The maleimide group can subsequently react with sulfhydryls on the other component, which can be introduced by previously mentioned crosslinkers, thus forming a stable thioether bond between the components. If steric hindrance between components interferes with either component's activity or the ability of the linear polymer to act as a glycosyltransferase substrate, crosslinkers can be used which introduce long spacer arms between components and include derivatives of some of the previously mentioned crosslinkers (i.e., SPDP). Thus, there is an abundance of suitable crosslinkers, which are useful; each of which is selected depending on the effects it has on optimal peptide conjugate and linear polymer production.

A variety of reagents are used to modify the components of the networks with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bi-functional reagents contain two identical or two dissimilar sites, respectively, which may be reactive for amino, sulfhydryl, guanidino, indole, or nonspecific groups.

Preferred Specific Sites in Crosslinking Reagents

1. Amino-Reactive Groups

In one preferred embodiment, the sites on the cross-linker are amino-reactive groups. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of a sIPN component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the sIPN components. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained.

Isocyanates (and isothiocyanates) react with the primary amines of the sIPN components to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of sIPN components, but also with sulfhydryl and imidazole groups.

p-Nitrophenyl esters of mono- and dicarboxylic acids are also useful amino-reactive groups. Although the reagent specificity is not very high, α- and ε-amino groups appear to react most rapidly.

Aldehydes such as glutaraldehyde react with primary amines of the linear polymer or components of the cross-linked polymer. Although unstable Schiff bases are formed upon reaction of the amino groups with the aldehydes of the aldehydes, glutaraldehyde is capable of modifying a component of the sIPN with stable crosslinks. At pH 6-8, the pH of typical crosslinking conditions, the cyclic polymers undergo a dehydration to form α-β unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites of the sIPN components, but reaction with the amino groups is the most important, resulting in a stable sulfonamide linkage.

2. Sulfhydryl-Reactive Groups

In another preferred embodiment, the sites are sulfhydryl-reactive groups. Useful, non-limiting examples of sulfhydryl-reactive groups include maleimides, alkyl halides, pyridyl disulfides, and thiophthalimides.

Maleimides react preferentially with the sulfhydryl group of the IPN or sIPN components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form disulfides.

3. Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage teach how to modify a carboxyl group with carbodiimde (Yamada et al., *Biochemistry* 20: 4836-4842, 1981).

Preferred Nonspecific Sites in Crosslinking Reagents

In addition to the use of site-specific reactive moieties, the present invention contemplates the use of non-specific reactive groups to link together two components of the IPN or sIPN.

Exemplary non-specific cross-linkers include photoactivatable groups, completely inert in the dark, which are converted to reactive species upon absorption of a photon of appropriate energy. In one preferred embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wave length. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming crosslinks.

Homobifunctional Reagents

1. Homobifunctional Crosslinkers Reactive with Primary Amines

Synthesis, properties, and applications of amine-reactive cross-linkers are commercially described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy) ethylsulfone (BSOCOES), bis-2-(sulfosuccinimidooxy-carbonyloxy)ethylsulfone (sulfo-BSOCOE S), ethylene glycolbis(succinimidylsuccinate) (EGS), ethylene glycolbis (sulfosuccinimidylsuccinate) (sulfo-EGS), dithiobis (succinimidyl-propionate) (DSP), and dithiobis (sulfosuccinimidylpropionate (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3,3'-(tetramethylenedioxy)-dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and α-naphthol-2,4-disulfonyl chloride.

Preferred, non-limiting examples of additional amino-reactive homobifunctional reagents include erythritolbiscarbonate which reacts with amines to give biscarbamates.

2. Homobifunctional Crosslinkers Reactive with Free Sulfhydryl Groups

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene) bismaleimide, N,N'-(1,2-phenylene)bismaleimide, azophenyldimaleimide, and bis(N-maleimidomethyl) ether.

Preferred, non-limiting examples of homobifunctional pyridyl disulfides include 1,4-di-3'-(2'-pyridyldithio)propionamidobutane (DPDPB).

Preferred, non-limiting examples of homobifunctional alkyl halides include 2,2'-dicarboxy-4,4'-diiodoacetamidoazobenzene, α,α'-diiodo-p-xylenesulfonic acid, α, α'-dibromo-p-xylenesulfonic acid, N,N'-bis(b-bromoethyl)benzylamine, N,N'-di(bromoacetyl)phenylthydrazine, and 1,2-di(bromoacetyl)amino-3-phenylpropane.

3. Homobifunctional Photoactivatable Crosslinkers

Synthesis, properties, and applications of such reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-β-(4-azidosalicylamido)ethyldisulfide (BASED), di-N-(2-nitro-4-azidophenyl)-cystamine-S,S-dioxide (DNCO), and 4,4'-dithiobisphenylazide.

HeteroBifunctional Reagents

1. Amino-Reactive HeteroBifunctional Reagents with a Pyridyl Disulfide Moiety

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio) propionate (SPDP), succinimidyl 63-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio) toluene (SMPT), and sulfosuccinimidyl 6-α-methyl-α-(2-pyridyldithio)toluamidohexanoate (sulfo-LC-SMPT).

2. Amino-Reactive HeteroBifunctional Reagents with a Maleimide Moiety

Synthesis, properties, and applications of such reagents are described in the literature. Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MB S), m-maleimidobenzoyl-N-hydroxysulfosuccinimide ester (sulfo-MB S), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

3. Amino-Reactive HeteroBifunctional Reagents with an Alkyl Halide Moiety

Synthesis, properties, and applications of such reagents are described in the literature. Preferred, non-limiting examples of hetero-bifunctional reagents with an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino)hexanoylamino)hexanoate (SIAXX), succinimidyl-6-(((4-(iodoacetyl)-amino)-methyl)-cyclohexane-1-carbonyl)aminohexanoate (SIACX), and succinimidyl-4((iodoacetyl)-amino)methylcyclohexane-1-carboxylate (SIAC).

A preferred example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety for primary amino groups is defined by the reaction temperature (McKenzie et al., *Protein Chem.* 7: 581-592 (1988)).

Preferred, non-limiting examples of hetero-bifunctional reagents with an alkyl halide moiety and an amino-reactive p-nitrophenyl ester moiety include p-nitrophenyl iodoacetate (NPIA).

Other cross-linking agents are known to those of skill in the art (see, for example, Pomato et al., U.S. Pat. No. 5,965,106. It is within the abilities of one of skill in the art to choose an appropriate cross-linking agent for a particular application.

Purification of the Networks of the Invention

The products produced (either IPNs or sIPNs) by the processes described herein can be used without purification. However, it is usually preferred to recover the product. Standard, well-known techniques for recovery of polymers such as thin or thick layer chromatography, column chromatography, ion exchange chromatography, gel permeation chromatography or membrane filtration can be used. It is preferred to use membrane filtration, more preferably utilizing a nanofiltration or reverse osmotic membrane, or one or more column chromatographic techniques for the recovery as is discussed hereinafter and in the literature cited herein. For instance, membrane filtration can be used to remove unreacted or incompletely reacted monomers and oligomers. Nanofiltration or reverse osmosis can be used to remove salts and/or purify the products. Nanofilter membranes are a class of reverse osmosis membranes that pass monovalent salts but retain polyvalent salts and uncharged solutes larger than about 100 to about 2,000 Daltons, depending upon the membrane used. Thus, in a typical application, IPNs or sIPNs prepared by the methods of the present invention will be retained in the membrane and contaminating salts will pass through.

If the IPN or sIPN results in the formation of a solid, the particulate material is removed, for example, by centrifugation or ultrafiltration.

Other methods of purification of IPNs or sIPNs of the invention that are derivatized with a ligand include, e.g., immunoaffinity chromatography, ion-exchange column fractionation (e.g., on diethylaminoethyl (DEAE) or networks containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

A protease inhibitor, e.g., methylsulfonylfluoride (PMSF) may be included in any of the foregoing steps to inhibit proteolysis and antibiotics may be included to prevent the growth of adventitious contaminants.

Finally, one or more RP-HPLC steps employing hydrophobic RP-HPLC media, e.g., silica gel having pendant methyl or other aliphatic groups, may be employed to further purify a polypeptide variant composition. Some or all of the foregoing purification steps, in various combinations, can also be employed to provide a homogeneous modified glycoprotein.

sIPNs

In a second aspect, the invention provides a network which is a semi-interpenetrating polymer network. The semi-interpenetrating polymer network includes (a) a cross-linked polymer; and (b) a linear polymer entangled within said cross-linked polymer. Covalently grafted to the cross-linked polymer and/or the linear polymer is a ligand which affects the adhesion of the stem cell to the network or the growth or differentiation of a stem cell. Exemplary ligands of use in the invention, such as adhesion peptides, growth factors and differentiation factors, are defined herein.

Cross-linking polymers of use in the sIPN are described and discussed in the IPN section. All of the cross-linked polymers discussed herein can be employed in the sIPNs of the invention.

Similar to the cross-linked polymer, properties (e.g., the hydrophobicity/hydrophilicity) of the linear polymer can be varied. Moreover, characteristics of the polymer such as length and number and identity of reactive functional groups can be varied as desired for a particular application.

Useful linear polymer chains include any long-chain polymer that contains a functional group (e.g., —$NH_2$, —$COO^-$, —SH, etc.) that is amenable to modification with biomolecules. Examples of such linear polymers are hyaluronic acid (HA), poly(methacrylic acid), poly(ethylene glycol) (EG), or poly(lysine). The linear polymer chain can also be a copolymer, e.g. p(AAc-co-EG), or a terpolymer. The only requirement for the linear chain is that is amenable to either grafting biological molecules or particles, e.g., for gene therapy and does not interfere with the phase change properties of the cross-linked network.

Another exemplary class of linear polymers is electrically-responsive polymers for fostering growth of electrically-responsive cells such as cardiac myocytes or neurons. In addition to p(AAc), linear chains of poly(methacrylic acid), poly(dimethyl-aminopropylacrylamide), poly(2-acrylamido-2-methylpropane sulphonic acid), HA, copolymers of these polymers, and other electro-responsive linear polymers that change their shape under an electric field or potential can be incorporated into the sIPN. These chains can be additionally functionalized with biomolecules to make an electrically and bioactive hydrogel capable of stimulating cell growth and alignment. The cellular alignment is caused by the templating of the cells on the aligned electrically active linear polymer chains.

In some embodiments, the linear polymer or copolymer chain described herein can be grafted with peptides used for cell adhesion, e.g. those that engage with integrins, or added directly with cells to aggregate the cells and cluster them for implantation. In still further embodiments, the polymers described herein can be functionalized with HA combined with HA binding peptides to cross-link the gel. The HA binding peptides can have a "center" portion that is biodegradable to achieve the advantages of the invention as discussed herein.

Methods of Making the sIPNs

Methods of making sIPNs are known in the art. Examples of sIPN synthesis are provided in the Examples section.

Ligands

The networks of the invention also include a ligand, e.g., a biomolecule such as a functional protein, enzyme, antigen, antibody, peptide, nucleic acid (e.g., single nucleotides or nucleosides, oligonucleotides, polynucleotides and single- and higher-stranded nucleic acids), lectin, receptor, saccharide, ganglioside, cerebroside or a combination thereof.

Biomolecules useful in practicing the present invention can be derived from any source. The biomolecules can be isolated from natural sources or they can be produced by synthetic methods. Peptides can be natural peptides or mutated peptides. Mutations can be effected by chemical mutagenesis, site-directed mutagenesis or other means of inducing mutations known to those of skill in the art. Peptides and proteins useful in practicing the instant invention include, for example, enzymes, antigens, antibodies and receptors. Antibodies can be either polyclonal or monoclonal.

Biomolecules of use in the compositions of the present invention include natural and modified biomolecules and therapeutic moieties. The discussion that follows focuses on the use of a peptide as an exemplary biomolecule. The focus is for clarity of illustration only. It will be apparent to those of skill in the art that substantially any biomolecule can be incorporated into the compositions of the invention.

In an exemplary embodiment, the ligand promotes the adhesion, growth or differentiation of a stem cell. Examples of these stem cells include embryonic stem cells, adult marrow stem cells, adult neural stem cells, cord blood stem cells, adult skin stem cells, adult liver stem cells, adult olfactory stem cells, adult adipose-derived stem cells, adult hair follicle stem cells, adult skeletal muscle stem cells, and adult myogenic muscle stem cells.

Exemplary peptides that can be utilized in forming the compositions of the invention are set forth in Table 1.

TABLE 1

| Hormones and Growth Factors | Receptors and Chimeric Receptors |
|---|---|
| G-CSF | CD4 |
| GM-CSF | Tumor Necrosis Factor (TNF) receptor |
| TPO | |
| EPO | Alpha-CD20 |
| EPO variants | MAb-CD20 |
| alpha-TNF | MAb-alpha-CD3 |
| Leptin | MAb-TNF receptor |
| Hedgehogs | MAb-CD4 |
| Fibroblast Growth Factors | PSGL-1 |
| Wnt | MAb-PSGL-1 |
| Activin | Complement |
| Delta/Notch | GlyCAM or its chimera |
| Bone Morphogenetic Proteins | N-CAM or its chimera |
| TGF-β | Monoclonal Antibodies |
| Enzymes and Inhibitors | (Immunoglobulins) |
| t-PA | MAb-anti-RSV |
| t-PA variants | MAb-anti-IL-2 receptor |
| Urokinase | MAb-anti-CEA |
| Factors VII, VIII, IX, X | MAb-anti-platelet IIb/IIIa receptor |
| DNase | MAb-anti-EGF |
| Glucocerebrosidase | MAb-anti-Her-2 receptor |
| Hirudin | Cells |
| α1 antitrypsin | Red blood cells |
| Antithrombin III | White blood cells (e.g., T cells, |
| Cytokines and Chimeric Cytokines | B cells, dendritic cells, |
| Interleukin-1 (IL-1), 1B, 2, 3, 4, 6 and 11 | macrophages, NK cells, neutrophils, monocytes and the |
| Interferon-alpha (IFN-alpha) | like |
| IFN-alpha-2b | Stem cells |
| IFN-beta | |
| IFN-gamma | |
| Chimeric diptheria toxin-IL-2 | |

Other exemplary peptides useful in the composition of the invention include members of the immunoglobulin family (e.g., antibodies, MHC molecules, T cell receptors, and the like), intercellular receptors (e.g., integrins, receptors for hormones or growth factors and the like) lectins, and cytokines (e.g., interleukins). Additional examples include tissue-type plasminogen activator (t-PA), renin, clotting factors such as factor VIII and factor IX, bombesin, thrombin, hematopoietic growth factor, colony stimulating factors, viral antigens, complement proteins, α1-antitrypsin, erythropoietin, P-selectin glycopeptide ligand-1 (PSGL-1), granulocyte-macrophage colony stimulating factor, anti-thrombin III, interleukins, interferons, proteins A and C, fibrinogen, herceptin, leptin, glycosidases, among many others. This list of polypeptides is exemplary, not exclusive. The network of the invention can also include a chimeric protein, including, but not limited to, chimeric proteins that include a moiety derived from an immunoglobulin, such as IgG.

Other biomolecules that can be grafted to a network of the invention, include Nestin, Vimentin, Prominin/CD133, Sonic hedgehog and other hedgehog ligands, Wnt ligands, Neurocan/tenascin C, Nurr 1, Pax-6, Sox-2, Musashi-1, NG2/CSPG-4, Neuro D3, Neurogenin 1, and fragments and subsequences of these molecules. Growth factors are also of use in the materials and methods of the invention, e.g., CNTF, BDNF, and GDNF.

Other exemplary biomolecules include Beta tubulin III, MAP2, Neuron specific enolase, NCAM, CD24, HAS, Synapsin I, Synaptophysin, CAMK Iia, Tyrosine hydroxylase, Glutamate transporter, Glutamate receptor, Choline receptor, nicotinic A2, EphB2, GABA-A receptor, Serotonin (5HT-3) receptor, Choline acetyltransferase and fragments and subsequences thereof. These biomolecules can be particularly important when the stem cell of interest is a neuronal stem cell.

When the cells are astrocytes or progenitors thereof exemplary biomolecules of use in the materials and methods of the invention include GFAP, GAD65, S100 and fragments and subsequences thereof.

When the cells are oligodendrocytes or progenitors thereof, exemplary biomolecules of use in the materials and methods of the invention include Olig 1, Plp/DM20, Myelin basic protein, and fragments and subsequences thereof.

Certain disease related biomolecules of use in the invention include, e.g., Presenilin-1, Beta APP, Bc1-2, Huntington's disease protein, and fragments and subsequences thereof.

The invention also provides networks in which the biomolecule is a member selected from GAPDH, Beta actin, Lamin A, Hat1, Hat5, and YBBR, and fragments and subsequences thereof.

In another exemplary embodiment, the biomolecule is a peptide that promotes adhesion of the stem cell to the network. An example is a peptide that contains the arginine-glycine-aspartate (RGD) motif. The RGD tripeptide motif is found in proteins of the extracellular matrix. Integrins link the intracellular cytoskeleton of cells with the extracellular matrix by recognizing peptides that include the RGD motif. RGD peptides interact with the integrin receptor sites, which can initiate cell-signaling processes and influence many different cellular processes (Kantlehner et al., *Angew. Chem. Int. Ed.* 38: 560 (1999)).

The covalent grafting of RGD peptides to the network provides a novel material that controls cell adhesion to itself and, hence, to other materials to which it is attached. Accordingly, the present invention provides a sIPN that includes a peptide having the RGD motif.

Frequently, active RGD peptides are head-to-tail cyclic pentapeptides. In an exemplary embodiment, the network of the invention includes a ligand which is a cyclic pentapetpide. An exemplary bicyclic RGD peptide, H-Glu[cyclo (Arg-Gly-Asp-D-Phe-Lys)]$_2$, was recently reported by Janssen et al. to possess high affinity $\alpha v \beta 3$ integrin binding (IC50=0.9 nM) with low affinity for $\alpha v \beta 5$ and $\alpha II \beta 3$ integrin (IC$_{50}$=10 nM) (Janssen et al., *Cancer Research* 62: 6146 (2002)). In another exemplary embodiment, the peptide is cyclo (Arg-Gly-Asp-D-Phe-Lys).

In another exemplary embodiment, the invention provides a network to stimulate bone formation incorporating the adhesion peptides bsp-RGD(15) [(acetyl)-CGGNGEPRGD-TYRAY-NH$_2$] (SEQ ID NO: 1) (-RGD-) and (acetyl)-CGG-FHRRIKA-NH$_2$ (SEQ ID NO: 4) (—FHRRIKA-; SEQ ID NO: 5), selected from the cell-binding and heparin-binding domains of bone sialoprotein (BSP), to accelerate proliferation of stem cells in contact with the peptide modified p(NIPAAm-co-AAc) hydrogels.

The peptides of use as ligands in the networks of the invention can also include amino acid residues upon which an array of conjugation reactions can be practiced. For example, a peptide, cyclo(Arg-Gly-Asp-D-Tyr-Lys) (SEQ ID NO: 6) incorporates a tyrosine into this active motif for iodination and for glycosylation (Haubner et al., *J. Nucl. Med.* 42: 326-36 (2001)).

The biomolecule of the invention can be grafted to a network either directly or through a crosslinking agent.

Both naturally derived and synthetic peptides and nucleic acids are of use as ligands in conjunction with the present invention; these molecules can be grafted to a component of the network by any available reactive group. For example, peptides can be grafted through a reactive amine, carboxyl, sulfhydryl, or hydroxyl group. The reactive group can reside at a peptide terminus or at a site internal to the peptide chain. Nucleic acids can be grafted through a reactive group on a base (e.g., exocyclic amine) or an available hydroxyl group on a sugar moiety (e.g., 3'-or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In a further preferred embodiment, the network includes a ligand which is a targeting species that is selected to direct the network of the invention to a specific tissue. Exemplary species of use for targeting applications include signaling peptides, peptides which bind to cell-surface receptors, antibodies and hormones.

The materials of the invention also allow for variation in peptide structure in order to optimize a property of the bound cell, e.g., binding to the material, proliferation, differentiation, etc.

Moreover, the density of the ligand on the network of the invention can be varied. For example, peptide densities from as low as about 0.01 pM to as high as about 100 pM are of use in the present invention.

Methods of Conjugating Ligands to a Network of the Invention

Methods of conjugating ligand to networks are well known to those of skill in the art. See, for example Hermanson, BIOCONIUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991.

The ligand is grafted to either a cross-linked polymer or a linear polymer either directly or through a cross-linking agent. Either of these modes of attachment can be engineered to produce a linkage that is either stable under biologically relevant conditions, or which is cleaved under selected conditions, releasing the ligand from the network.

In general, the polymers of the networks (either cross-linked or linear) and the ligand are linked together through the use of reactive groups, which are typically transformed by the linking process into a new organic functional group or unreactive species. The reactive functional group(s), is located at any position of the biomolecule and the linear polymer that is convenient. Reactive groups and classes of reactions useful in practicing the present invention are generally those that are well known in the art of bioconjugate chemistry. Currently favored classes of reactions available with reactive species are those, which proceed under relatively mild conditions. These include, but are not limited to nucleophilic substitutions (e.g., reactions of amines and alcohols with acyl halides, active esters), electrophilic substitutions (e.g., enamine reactions)

and additions to carbon-carbon and carbon-heteroatom multiple bonds (e.g., Michael reaction, Diels-Alder addition). These and other useful reactions are discussed in numerous texts and literature references, for example, March, ADVANCED ORGANIC CHEMISTRY, 3rd Ed., John Wiley & Sons, New York, 1985; Hermanson, BIOCONIUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Methods and chemistry for activating polymers, as well as methods for conjugating ligands onto polymers, are described in the literature. See, R. F. Taylor, (1991), PROTEIN IMMOBILISATION. FUNDAMENTALS AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, *Macronol. Chem. Phys*. C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); and Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), haemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Useful reactive functional groups pendent from a cross-linked polymer, linear polymer or ligand include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the IPN, sIPN or their components. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Degradable Cross-Links

In another aspect, the IPN or sIPN can comprise a degradable cross-linker. This cross-linker can be used to attach the ligand to the cross-linked polymer or the linear polymer. The cross-linker can also be used as a component of the cross-linked polymer. the cross-linker can be cleaved to dissociate the cross-linked species.

Many cleaveable groups are known in the art. See, for example, Jung et al., *Biochem. Biophys. Acta* 761: 152-162 (1983); Joshi et al., *J. Biol. Chem.* 265: 14518-14525 (1990); Zarling et al., *J. Immunol.* 124: 913-920 (1980); Bouizar et al., *Eur. J. Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups are commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to their being endocytized (e.g., cis-aconityl; see, Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

In another exemplary embodiment, the crosslinkers are degradable via hydrolysis. Examples of such cross-linkers include poly(glycolide) [poly(glycolic acid)], poly(lactide) (pL) [poly(lactic acid], poly($\epsilon$-caprolactone) (pEC), other $\alpha$-hydroxy acid esters, and copolymers of these materials with pEG [e.g., random, block].

In yet another exemplary embodiment, the IPNs and sIPNs of the invention are used in the context of the natural process of proteolytic remodeling of the extracellular matrix, which is essential in tissue morphogenesis during fetal development, inflammation, arthritis, cancer, and wound healing and tissue regeneration (Massova et al., *FASEB Journal*, 12:1075-1095 (1998); Johansson et al., *Developmental Dynamics*, 208:387-397 (1997)). To make the networks degradable oligopeptide crosslinkers that are specifically cleaved by the matrix metalloproteinase (MMP) family are incorporated into the IPNs and sIPNs. MMPs are a structurally and functionally related family of zinc-dependent endopeptidases that cleave either one or several ECM proteins (Massova et al., *FASEB Journal*, 12:1075-1095 (1998)). Recently, West and Hubbell (West et al., *Macromolecules*, 32:241-244 (1999)) developed a new class of telechelic biodegradable block copolymers that when synthesized into a crosslinked hydrogel were specifically degraded by either plasmin or crude collagenase. Thus, the feasibility of protease degradation of oligopeptide crosslinked hydrogels has been demonstrated in vitro (West et al., *Macromolecules,* 32:241-244 (1999)).

Figure 30:
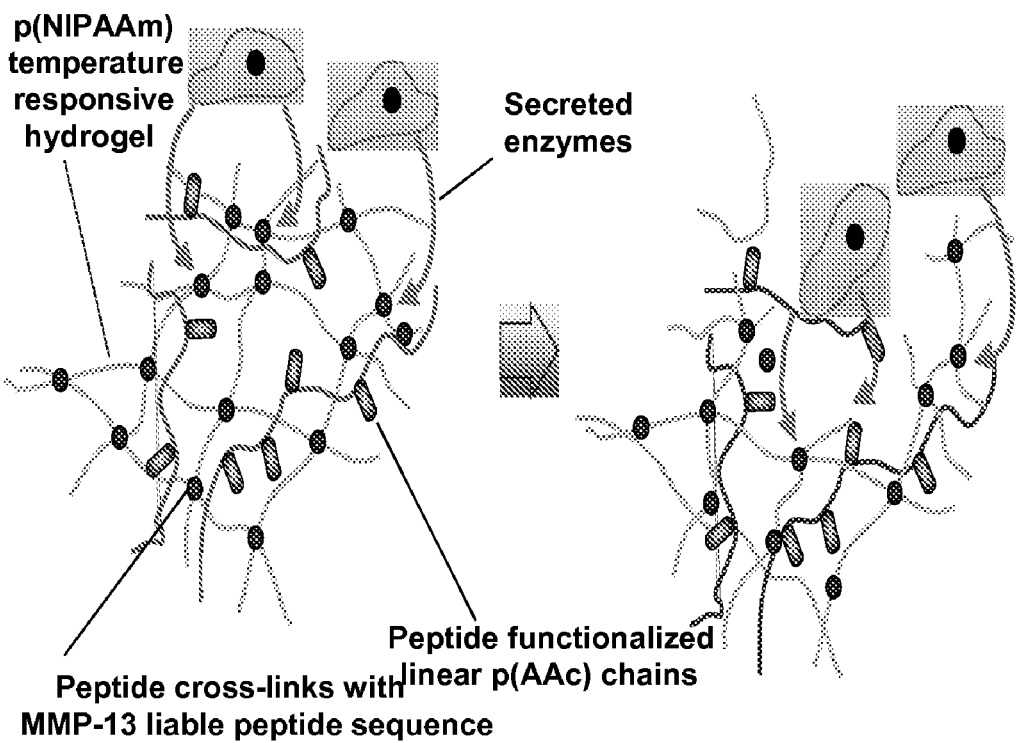
FIG. 30 provides a schematic representation of the injectable semi-interpenetrating polymer networks (sIPNs), comprised of p(NIPAAm-co-AAc) hydrogels with linear peptide-modified p(AAc) or HyA chains physically entangled within the network. Cells degrade the matrix via enzymatic degradation of the MMP-13 labile crosslinks holding the network together.

An exemplary embodiment of the invention is an IPN or sIPN which incorporates peptide crosslinkers that are cleaved by collagenase-3 (MMP-13). See FIG. 30. Since MMP-13 has primary, secondary, and tertiary cleavage sites for type II collagen, all with different enzyme-substrate affinity ($K_M$) and maximal catalytic rate when substrate is saturating ($k_{cat}$), (Mitchell et al., *Journal of Clinical Investigation,* 97:761-768 (1996)) then theoretically the degradation rate of the hydrogel could be tailored by selecting peptides with the appropriate cleavage site.

In an exemplary embodiment, the IPN or sIPN of the invention includes a peptide crosslinker (see Example 8 for a discussion specifically involving sIPNs) as a component. The degradation rates of the IPNs and sIPNs with peptide crosslinkers can be altered by synthesizing the network with mixed crosslinkers with different cleavage sites for MMP-13, e.g. primary versus tertiary sites, by changing the crosslinker density, and by changing substrate length or amino acids flanking the cleavage site (West et al., *Macromolecules,* 32:241-244 (1999); (Netzel-Arnett et al., *Journal of Biological Chemistry,* 266:6747-6755 (1991)). The aforementioned modifications to the networks alter the degradation rates by changing $k_{cat}/K_M$, an index of substrate specificity.

Peptide crosslinkers can be synthesized on a commercial peptide synthesizer, purified, and verified to be >97% pure by HPLC and mass spectroscopy. The peptides are synthesized using standard methods with side group protection. Protection of the amine groups is critical since it is important for the docking of the MMP-13 to the peptide substrate (Mitchell et al., *Journal of Clinical Investigation,* 97:761-768 (1996)). To acrylate the peptides, while still on the resin, the Fmoc protection group from the N terminus is cleaved with 20% piperidine in dimethylformamide (DMF) and the free amine is acrylated by reacting acrylic acid with 1-ethyl-3-(3-dimethylaminopropyl) carbodiimide (EDC, Pierce, Rockford, Ill., USA) with the $NH_2$ in a similar manner to that described previously by Bearinger et al. (Bearinger et al., *Journal of Biomaterials Science, Polymer Edition,* 9:629-52 (1998)). Briefly, the carboxylic acid on the acrylic acid is linked to the N terminal amine by inducing a carbodiimide reaction utilizing 0.400 mg/ml EDC and 1.100 mg/ml N-Hydroxysulfosuccinimide (Sulfo-NHS, Pierce) in [2-(N-Morpholino) ethanesulfonic acid, 0.100 M, in 0.5 M NaCl conjugation buffer (MES, Pierce) at a pH of 6.0. Although this pH is low, it is not nearly low enough to cleave the peptide off the resin or remove side chain protection. The reaction proceeds for 1 h, and then the resin is rinsed with 10% TFA to cleave the peptide from the resin with side group protection intact. The carboxyl termini is acrylated in solution by reacting the —COOH with ethylenediamine with EDC (similar conditions as above) to generate a free amine and then following the reaction scheme outlined above for coupling acrylic acid with the —$NH_2$.

To synthesize the degradable network, the synthetic route and conditions for polymerization for a non-degradable network is used, replacing the non-degradable crosslinker with the peptide crosslinkers. The side chain protection groups on the cross-linkers are deprotected, e.g., with 90% TFA prior to synthesis. Degradable networks synthesized as described herein can be used in a similar manner to the non-degradable networks; however, the scaffold will be temporary based on the enzymatic cleavage of the cross-links. In the present invention, biodegradable networks can be used to provide a prosthetic that forms in situ and functions as a temporary fixation device. In some embodiments, a non-degradable network can also be used to serve as a permanent prosthetic.

In addition to the sIPN and IPN materials detailed above, other exemplary materials useful for the present invention includes alginate, hyaluronic acid, and type I collagen, self-assembling peptide-amphiphiles and nanofibers, and synthetic polymers, such as poly(glycolic acid), poly(lactic acid), copolymers of poly(glycolic acid) and poly(lactic acid), copolymers of poly(ethylene glycol), and polyester urethane urea.

With respect to the use of alginate, this polymerized polysaccharide can be adapted for injection and provide various of the benefits described herein. In some embodiments, alginate can be prepared in an injectable form by varying the concentration of the polysaccharide and calcium, as appreciated by those of skill in the art with guidance from the instant disclosure. Such preparation, or other injectable preparation, may then be applied to cardiac tissue structures according to various aspects described herein, either alone or in combination with other materials known in the art.

More specifically, compositions useful with the methods of the invention also include synthetic polymers, such as polyethylene oxide ("PEO"), PEO-poly-1-lactic acid ("PLLA-PEO block copolymer"), pluronics, and poly-(N-vinyl-2-pyrrolidone) ("PVP"), which can be adapted by those of ordinary skill in the art to provide the contemplated prosthetic structures or artificial extracellular matrices for transplanted cells. Various biologic polymers such as alginate, collagen, and fibrin glue, can be prepared in a manner for use as an injectable material to form the prosthetic and/or ECM structure under certain conditions. Benefits of each of these polymers include that they may be injected into the desired location without the need for more invasive implantation. Those of ordinary skill in the art, guided by the present disclosure, will be equipped to select materials having the appropriate properties or constitutive parameters, e.g. LCST, stiffness, bioactivity, suitable for use with the methods described herein.

In one more specific example, PEO is generally considered biocompatible and is known not to react with proteins and most biologic macromolecules. It is injectable, though larger needles such as 22 gauges are typically used for this material. According to another example, PEO-PLLA-PEO block copolymers are also generally considered biocompatible and biodegradable. However, formulations with this compound will typically undergo gel solution transitions around about 45° C., and are typically injected at temperatures above body temperature. A respective treatment system would in such circumstance generally also include a heater assembly. Pluronics are also known to be generally biocompatible, but are not typically considered biodegradable. They remain liquid at temperatures lower than 4° C., and thus catheter delivery may also further include active cooling and/or insulation along the catheter to provide and maintain the material at such temperatures until delivered. PVP is a material that may be injected through smaller gauge needles such as 30 gauge. It is also generally non-antigenic and non-toxic; however, it is generally not considered biodegradable. Alginate gels are typically linked together by calcium ions, which will dissociate and render the gel mechanically unstable over a period of time. They are also generally considered non-biodegradable and have been observed to be immunogenic in certain settings. Collagen gels are generally considered biocompatible and biodegradable, but are not typically mechanically stable.

Additional details on the materials described above can be found in one or more of the following references: MERRILL E W. "Poly(ethylene oxide) star molecules: synthesis, characterization, and applications in medicine and biology," J Biomater Sci Polym Ed, 1993; 5:1-11; PEPPAS N A, Langer R. "New challenges in biomaterials," Science, 1994; 263: 1715-20; SIMS C D, Butler P E, Casanova R, Lee B T, Randolph M A, Lee W P, Vacanti C A, Yaremchuk M J, "Injectable cartilage using polyethylene oxide polymer substrates," Plast Reconstr Surg. 1996; 98:843-50; JEONG B, Bae Y H, Lee D S, Kim S W, "Biodegradable block copolymers as injectable drug-delivery systems," Nature, 1997; 388: 860-2;ARPEY C J, Chang L K, Whitaker D C, "Injectability and tissue compatibility of poly-(N-vinyl-2-pyrrolidone) in the skin of rats: a pilot study," Dermatol Surg, 2000; 26:441-5; discussion 445-6; SMIDSROD O, Skjak-Braek G. "Alginate as immobilization matrix for cells," Trends Biotechnol, 1990; 8:71-8; Paige K T, Cima L G, Yaremchuk M J, Vacanti J P, Vacanti C A. "Injectable cartilage," Plast Reconstr Surg, 1995; 96:1390-8; discussion 1399-400. The disclosures of these references are incorporated herein by reference in their entireties for all purposes.

Moreover, whereas polymers are an exemplary means of providing a support structure and ECM in the myocardium, other non-polymer materials may be be used according to various aspects of the invention and embodiments. For example, integrin is an example of a protein which has been observed to enhance cellular binding and thus may be injected into cardiac tissue structures to provide substantial benefit to cellular tissue formation and/or retention there. For further illustration, further particular embodiments may also include integrin in combination with cell delivery, and/or in combination with other materials described as useful according to one or more of the aspects of the invention.

Guided Application of the Compositions to the Myocardium

To enhance the effectiveness and precision of the myocardial stabilizing methods of the invention, an advanced FEM methd, as described below, can be used in some embodiments to model the acute ventricular mechanical effects of implanted materials, e.g. IPN or a sIPN with or without entrained cells, and cellular masses, at one or more sites in the myocardium and thereby guide the application of the compositions and ultimately the placement or positioning of the prosthetic structure and/or supporting matrix. Application of the materials described herein can alter cardiac mechanics in a volume, stiffness, and location-dependent manner. Application of fractional volume of material as little as about 0.5% to about 5%, preferably at least about 0.5%, more preferably at least about 4.5%, of the total wall volume is sufficient to significantly reduce fiber stresses in a given injured myocardium region to levels found in remote regions, improve ejection fraction, and stroke volume (SV)/end-diastolic volume relationship. In preferred embodiments, a non-contractile material is used. In some embodiments, the materials described herein are applied to the border zone. In still further embodiments, modern drug or gene delivery methods can be used in conjunction with the materials and methods described herein to provide additional chemical therapeutic effect.

As the finite element methods described herein can provide a representative 3-dimensional geometry and accounts for the diastolic and systolic material properties for an actual imaged heart, these methods allow for patient-specific treatment of infarct injuries. The use of a finite element model for the analysis of an individual heart with specific geometry, cardiac fiber angles, and infarct/border zone location and dimension offers significant advantages over unguided positioning of the prosthetic structure and ECM. Using a finite element model of a patient's heart based on imaging data, obtainable by conventional procedures, allows for the optimization of individual treatment with regards to amount and placement of any tissue engineering materials to stabilize abnormally high stresses at certain site(s) unique to each patient.

In still further embodiments, the finite element methods described herein can be enhanced by refining the mesh to allow for intramural elements of injected material to delineate myocardial stresses that are generated on the myocytes compared to what is generated on added material during cardiac function. This approach can determine the effect of material properties of the implanted material in a more precise manner, especially with low stiffness materials.

The finite element model described herein is constructed from imaging data obtained from an ovine LV suffering from an antero-apical transmural dyskinetic infarct, and the resulting global function and local stresses were calculated for simulated injections of material as a function of volume, stiffness, and location. The model's mesh and regional material properties were modified to simulate expected changes. Three sets of simulations were run: (a) single injection to the anterior border zone; (b) therapeutic multiple border zone injections; and (c) injecting material to the infarct region.

Finite Element Model Calculations

To determine the effect of material injection to the LV, the three dimensional FEM method developed by Costa et al for large elastic deformations of ventricular myocardium was used, together with the passive diastolic and active systolic mathematical descriptions of Guccione et al describing the anisotropic stress-strain relationship of normal and dysfunctional myocardium. All model calculations were performed on a Silicon Graphics 02+ workstation (Mountain View, Calif.).

Previously Developed Finite Element Mesh

A previously developed and validated FEM simulation of an ovine heart suffering from an antero-apical infarct was used as the starting point for modeling the material injection. This previous work consisted of a 216 element mesh in a 12×18×1 grid (circumferential×longitudinal×transmural) with dimensions and model parameters fit to MRI measured cardiac geometry, fiber angle distribution, and mechanical properties of individual left ventricles that had surgically induced antero-apical transmural infarcts which expanded and became dyskinetic. The mesh had been divided into three different regions to best fit the physiological data—remote myocardium with normal passive myocardium properties, a border zone with normal passive myocardium but reduced active contraction, and a dyskinetic infarct with increased stiffness and no active contraction.

Simulation of synthetic ECM Injections

Figure 13A:
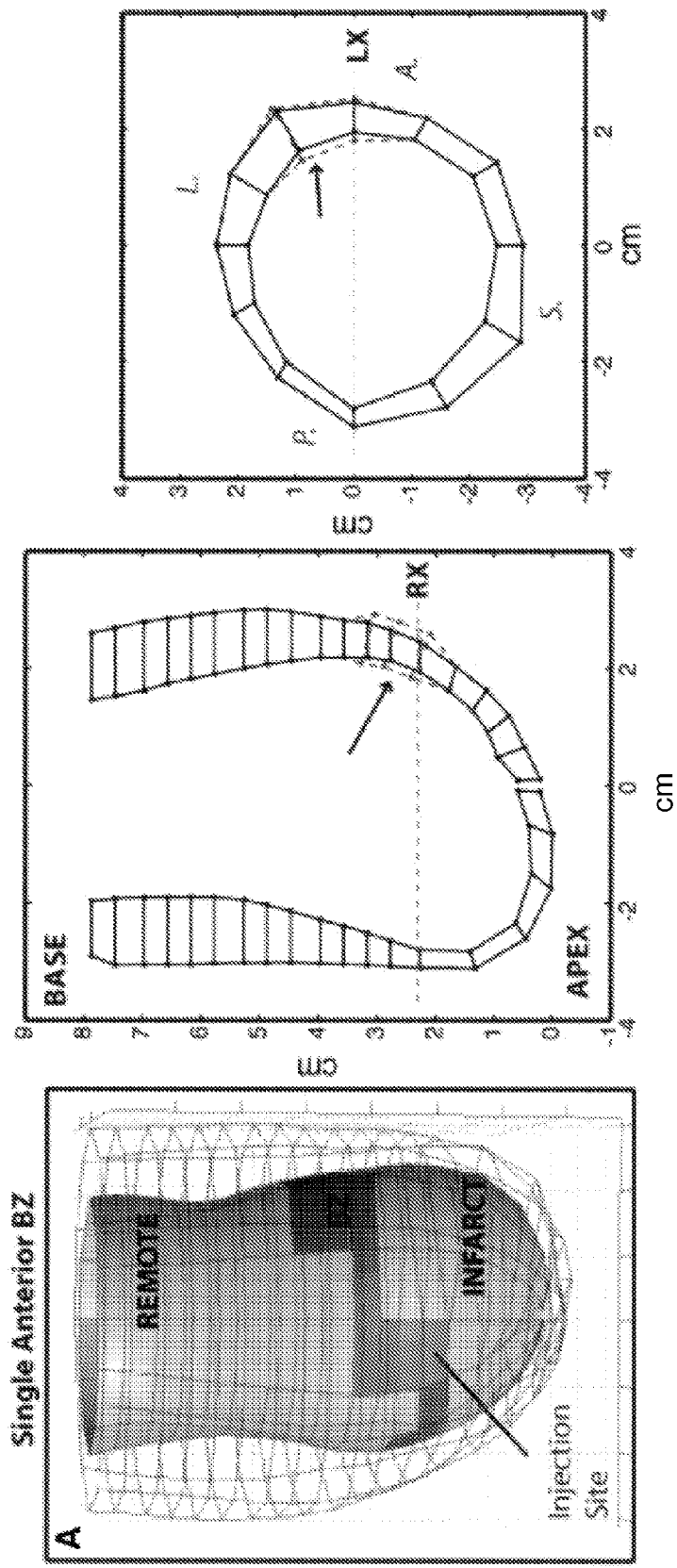
FIG. 13A. Single injection to anterior infarct border zone wall.

Simulated Injection into the Anterior Border Zone:

Injection of material to the anterior wall of the infarct border zone was simulated by changing the transmural coordinates of epicardial and endocardial mesh nodes in 3 of the anterior border zone elements to create local bulging in the apical anterior wall. The resulting deformation in the 3 chosen elements and surrounding 9 elements was varied to achieve a total wall volume increase of 0.5-1.5 mL (FIG. 13A). To simulate the addition of non-contractile volume, for each of the 12 elements with a deformation induced change of volume, contractility of the element as defined by the active contraction $T_{max}$ parameter[12] was reduced proportionally to the change in volume.

In addition, to investigate the role that stiffness (stress response to strain) of the injected material contributes to changes in cardiac mechanics, the passive material parameters of the strain energy constitutive equation[12] ($C$, $b_f$, $b_t$, $b_{fs}$) of the combined material/myocardium elements were modified to model added material using a volume-mixing rule. For these simulations, added material stiffness of 1-200% of the average stiffness of passive myocardium across was tested. This stiffness range (an elastic modulus range of ~10 Pa-20 kPa) was chosen to encompass a wide variety of possible injectable materials, estimated from literature values of shear storage modulus as determined by parallel plate rheology. This simulated range includes derived ECM materials such as fibrin (~50 Pa)[14] Matrigel™, (30-120 Pa for uncrosslinked and crosslinked),[15] and type I collagen gels (20-80 Pa for 13 mg/mL),[16] as well as newer synthetic ECM materials such as bioactive hydrogels (IPNs or sIPNs) based on N-isopropylacrylamide (100 Pa-400 Pa),[17,18] alginate (100 Pa-6 kPa),[19] and poly-ethylene glycol (1-5 kPa).[20] In addition, as most materials are significantly softer than the upper range tested in the simulations, the higher range also evaluates the likely effect that after injection and integration, materials and/or cells will stiffen beyond their initial properties.

Simulated Multiple Border Zone Injections:

A second simulation tested the global effect of injected material as a potential therapy, with a total of 4.4 mL (~4.5% of total wall volume) added in multiple locations in the infarct border zone. In this simulation, a total of 12 border zone elements in 4 surgically accessible locations (in the anterior, posterior, and septal walls) were modified, with the epicardial nodes scaled by a factor of 1.03 and the endocardial nodes by 0.97, both in the transmural direction, to locally thicken the wall in this region (FIG. 13B). In all modified elements, contractility ($T_{max}$) was proportionally decreased to the volume increase, and material stiffness (C, $b_f$, $b_t$, $b_{fs}$) of the composite elements reduced by a mixing rule, with the added volume fraction having 20% of the passive stiffness of normal myocardium.

Figure 13C:
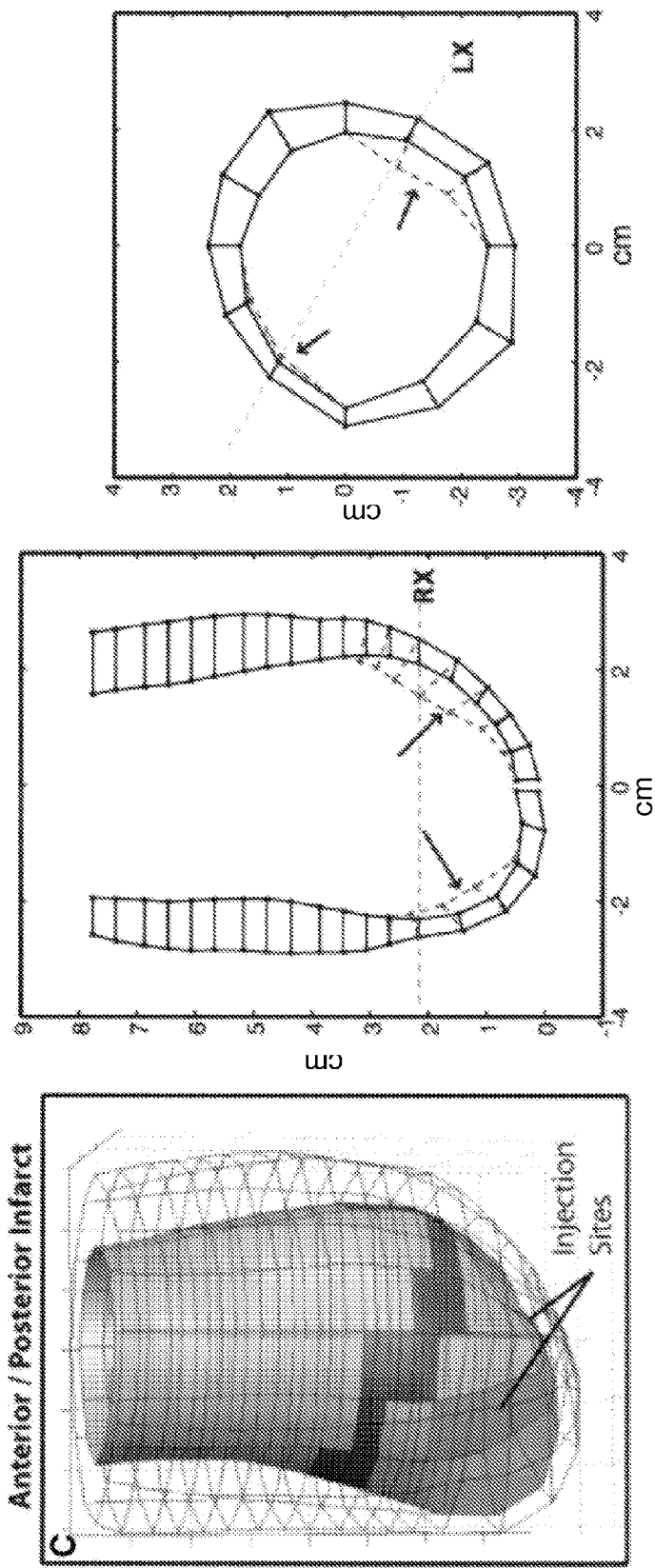
FIG. 13C. Injection of material to infarct region. Left panel: shows 3-dimensional representation of modeled ventricle where the wireframe depicts the epicardial surface and the solid color mesh the endocardial surface. Green elements are modeled as remote myocardium, red elements hypocontractile border zone, yellow elements infracted myocardium, and blue elements show regions where the mesh has been modified to simulate injection. Middle and right panels show longitudinal (LX) and radial cross sections (RX) respectively of modified regions with arrows indicating regions of volume additions and the dotted line indicating where the depicted longitudinal and radial cross sections are taken from in the ventricle model. The bottom panel also gives relative orientation of the depicted ventricle around the radial cross section (a=anterior, l =lateral, p =posterior, s =septal).

Simulated Injection into Anterior and Posterior Infarct:

A third set of simulations determined the effect of added material directly to the non-contractile infarct region. In these simulations, two regions of the apical infarct mesh were modified by transmural modifications to the epicardial nodes to model the geometry of material added to the infarct wall (FIG. 13C). Multiple simulations were performed with varying infarct deformations to test a total volume addition range of 0-5.3 mL. Material properties were also modified using a volume-mixing rule for the combined element with the added material having 20% stiffness of passive myocardium.

Calculation of End-Systolic and End-Diastolic Pressure-Volume Relationships

For each scenario. FEM diastolic solutions were obtained for LV pressures of 0-2.6 kPa (0-20 mmHg), after which active contraction was added and FEM end-systolic solutions calculated for LV pressures of 0-16 kPa (0-120 mmHg). Chamber end-diastolic and end-systolic volume ($V_{ED}$ and $V_{ES}$) solutions were used with the corresponding pressures ($P_{ED}$ and $P_{ES}$) to plot the end-diastolic and end-systolic pressure volume relationships (ESPVR and EDPVR), which were then fit to appropriate polynomial equations. The following linear equation used to estimate the ESPVR:

$$P_{ES}=E_{ES}(V_{ED}-V_0) \quad (1)$$

Where $E_{ES}$ is the end-systolic elastance and $V_0$ is the volume intercept of the ESPVR, each determined by linear regression of the data.

The polynomial equation used to estimate the EDPVR was:

$$P_{ED}=E_{0,ED}+E_{1,ED}V_{ED}+E_{2,ED}V_{ED}^2 \quad (2)$$

Where $E_{0,ED}$, $E_{1,ED}$, and $E_{2,ED}$ represent stiffness of the LV diastolic compliance, again determined by linear regression.

Calculation of EF, $SV/P_{ED}$ and $SV/V_{ED}$ Relationships

In order to determine global changes to pump function, the $SV/P_{ED}$ and $SVN_{ED}$ relationships were calculated and plotted. These relationships were determined by first calculating SV for the in vivo validated cardiac cycle, with $P_{ED}$=1.09 kPa (8.2 mmHg) and $P_{ES}$=10.24 kPa (76.8 mmHg). Using this calculated SV value and the EDPVR fit parameters; aortic elastance ($E_a$) could be solved for using the following equation:

$$SV = \frac{V_{ED} - V_0}{1 + E_{ES}/E_A} \quad (3)$$

With the calculated value of $E_A$, SV for all $P_{ED}$ as well as the EF, or SV as a percent of $V_{ED}$, could be determined and the relationships between SV and $P_{ED}$ and $V_{ED}$ plotted.

Calculation of Systolic Fiber Stress

Previously developed finite element methods for ventricular mechanics were used to calculate midwall stresses in reference to the local muscle fiber orientation at end systole. For the treatment simulations, the same in vivo measured end-systolic LV pressure of 10.24 kPa (76.8 mmHg) from the infarct model was chosen as the end-systolic pressure for stress calculation and for comparison of calculated stresses. This chosen end-systolic pressure is based on the assumption that the addition of non-contractile material to the ventricle does not significantly alter the pressure, which is a reasonable assumption since no contractility has been added and no changes in aortic elastance from the procedure are expected. In addition, published literature examples of cellular additions to the ventricle do not significantly alter the end-systolic pressure.

Figure 14A:
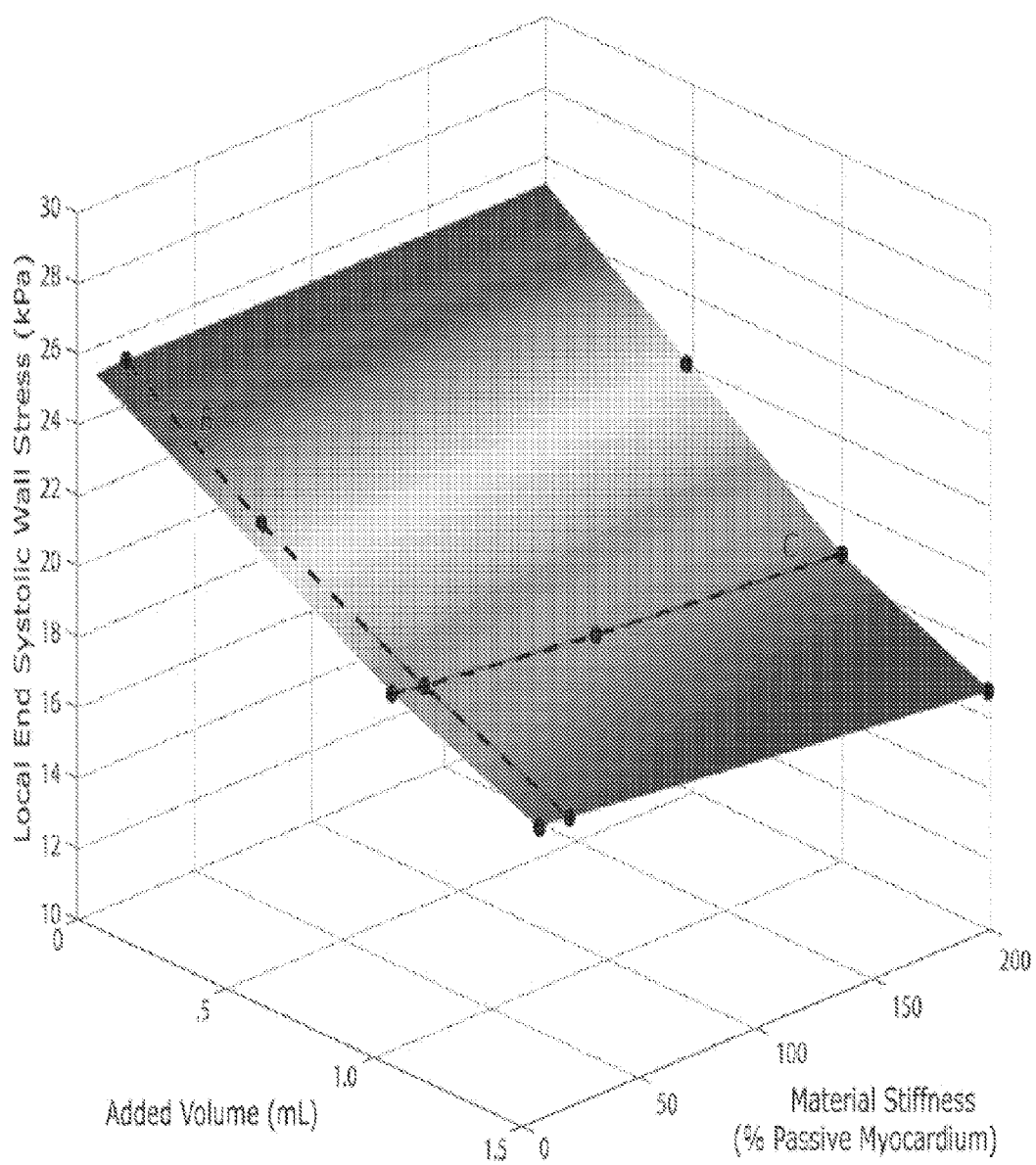
FIG. 14A. Local mean end systolic fiber stress in BZ and remote region elements with altered geometry from simulated injection. Filled circles represent simulated conditions with dotted lines depicting the surface cross sections shown in FIGS. 14B and 14C.

Simulated Injection into the Anterior Border Zone:

Mid-wall end-systolic fiber stresses in the local injection area were calculated at an LV pressure of 10.24 (76.8 mmHg) kPa for a range of injected volumes (0.5-1.5 mL), and a range of material properties (1-200% of normal diastolic stiffness). There are 12 elements in the volume-altered anterior region of these simulations, 6 of which are infarct elements and 6 of which are remote and BZ. The mean local fiber stress response of the BZ and remote region elements to both variables is depicted in FIG. 14A, with cross sections of this surface along with infarct element response shown in FIG. 14B and FIG. 14C.

Figure 14B:
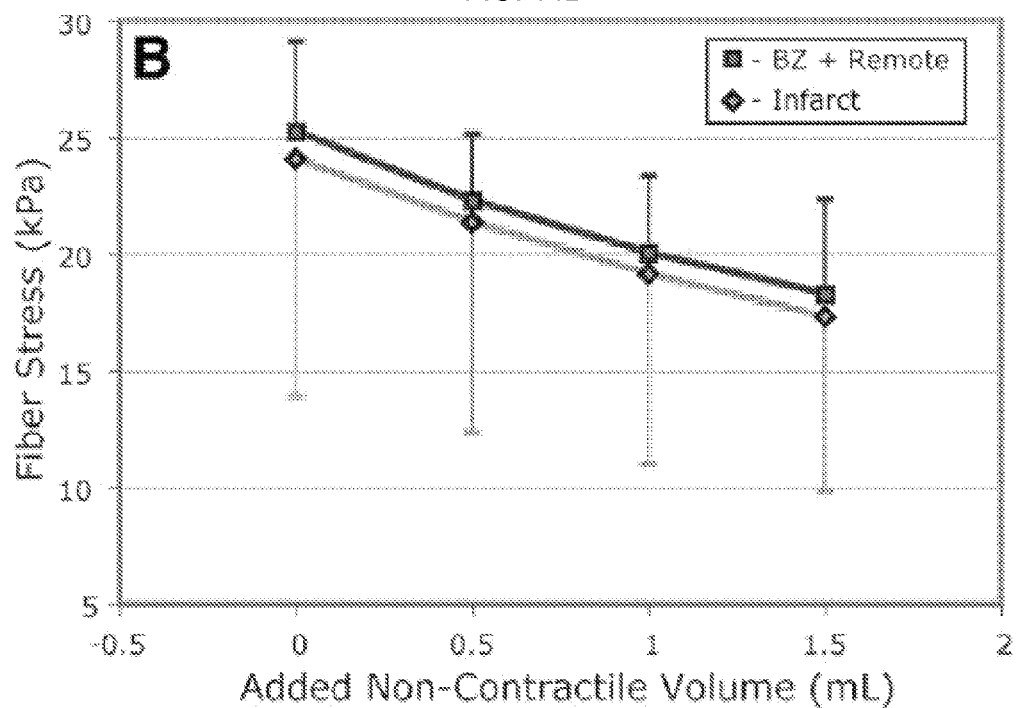
FIG. 14B. Fiber stress as a function of simulated injected volume with constant material stiffness. Values represent average mid wall stress and error bars standard deviations for the six infarct elements and the six remote + BZ elements in the local region.
Figure 14C:
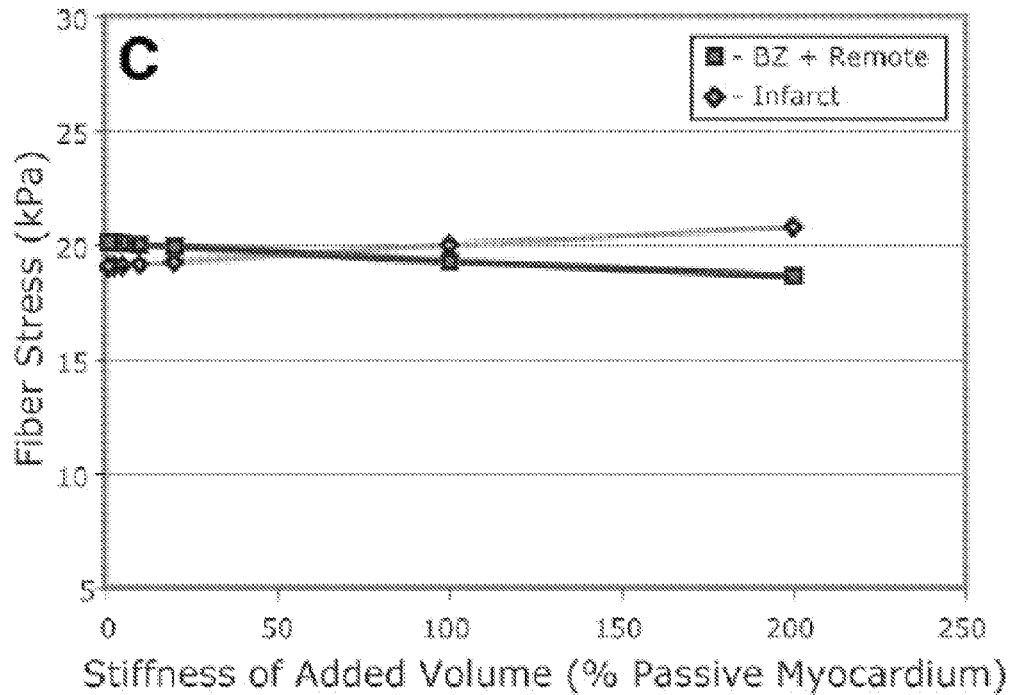
FIG. 14C. Change in local fiber stress for the simulated injection of 1 mL of volume as a function of material stiffness of the added volume. Values again represent the mean mid-wall fiber stresses of the group of six infarct elements and the six remote + BZ elements in the local region that were modified by non-contractile volume addition, standard deviations are omitted for clarity.

Mean volume weighted stress each of these two groups of elements shows a linear decrease with increasing added volume (FIG. 14B). Material properties also appears to have an effect, with the higher material stiffness materials bearing more of the load in the softer remote and BZ regions than the stiffer infarct and therefore resulting in a increased reduction in remote and BZ stresses (FIG. 14C). The small fractional volumes (0.5-1.5%) used in this single injection simulation have no significant effect on EF or global function.

Figure 15:
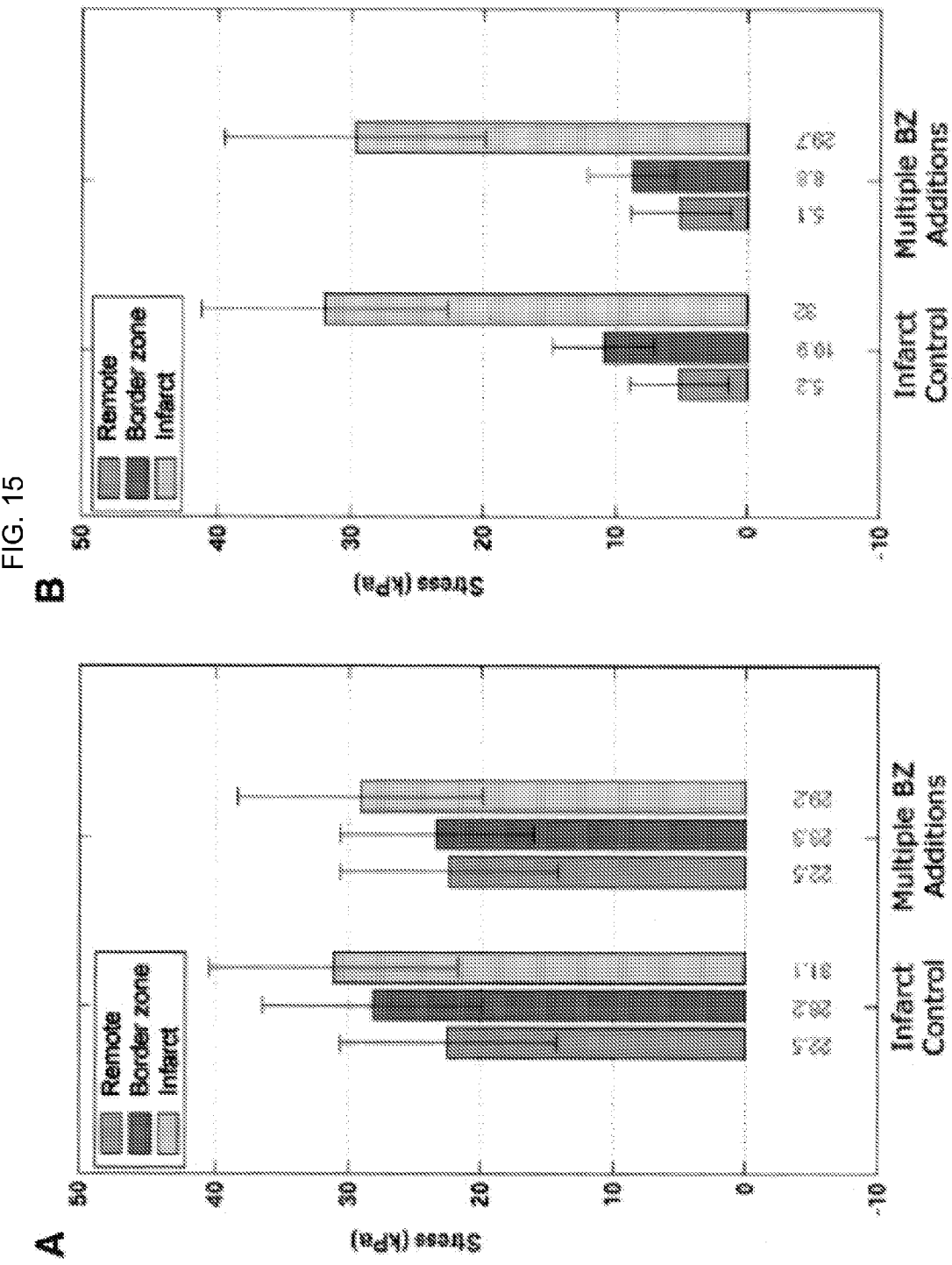
FIG. 15 Changes in average fiber (A) and cross fiber (B) stress as a function of the simulated injection of a total of 4.4 mL of material to the infarct border zone region in multiple injection sites. Bar heights represent the mean systolic mid-wall fiber stress for the groups of elements that make up the remote, border zone, and infarct simulation regions. Error bars represent the standard deviations of these mid-wall fiber stresses for each group.

Simulated Multiple Border Zone Injections:

In the simulation to investigate the effect of a potential treatment of multiple implantations throughout the peri-infarct border zone, results indicate that the addition of ~4.5% of the total wall volume (4.4 mL total volume change) to the border zone can bring mean volume weighted end-systolic fiber stress in the border zone back down to near levels in the remote myocardium (FIG. 15A). However, cross fiber stresses are not dramatically decreased (FIG. 15B) and the other four stress components are not changed significantly (data not shown). As mathematical models produce discreet results, statistical analysis is difficult to use to ascertain the significance of computed changes in variables. However, if the groups of elements that form the 'remote', 'BZ', and 'infarct' regions are assumed to represent biological variation, then their variance can be used to estimate significant differences between the data sets. In this case, using an analysis of variance on the 6 data sets in FIG. 15 followed by pairwise Holm's t-tests, the observed reduction in BZ fiber stress can be considered to be statistically significant (p<0.05) while the cross fiber stress is not significantly reduced.

Figure 16A:
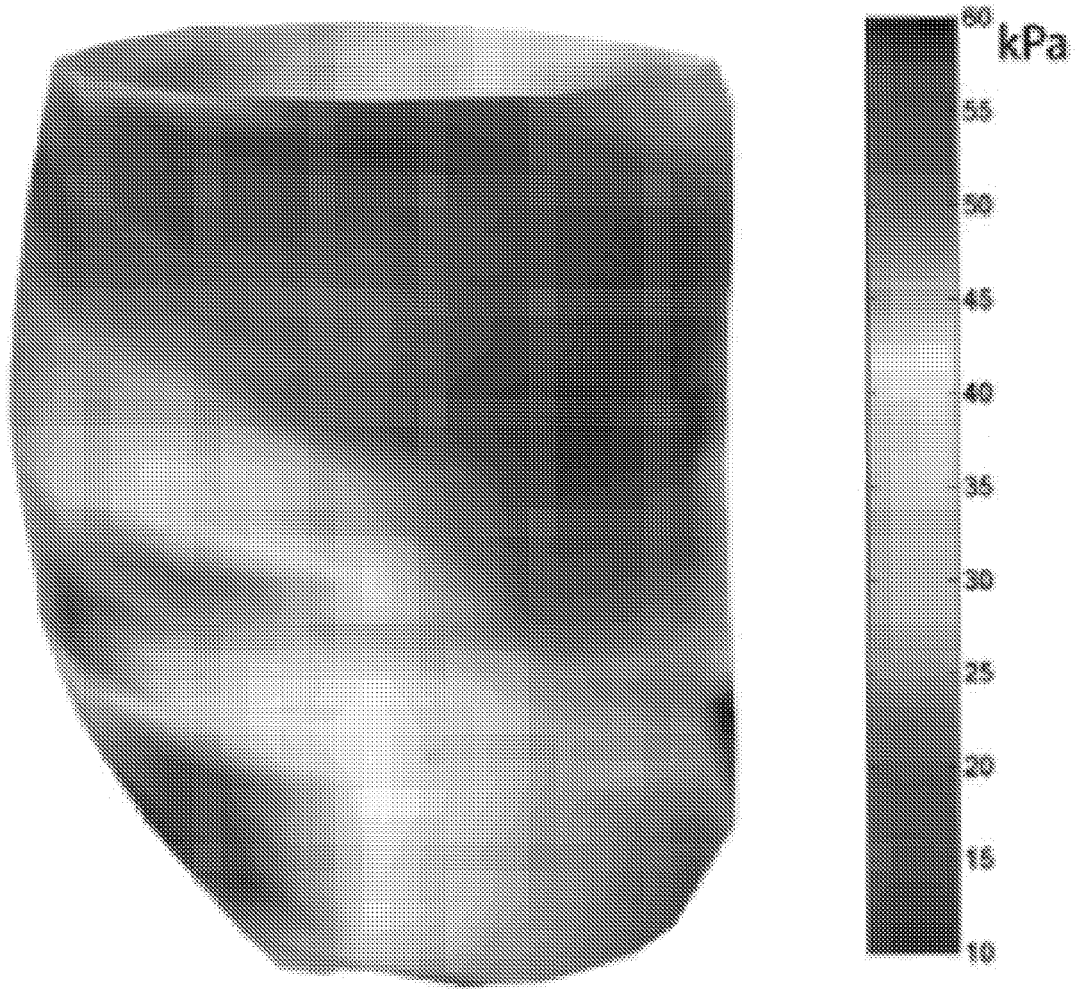
FIG. 16A. Mid wall fiber stress in the control infarct simulation.
Figure 16B:
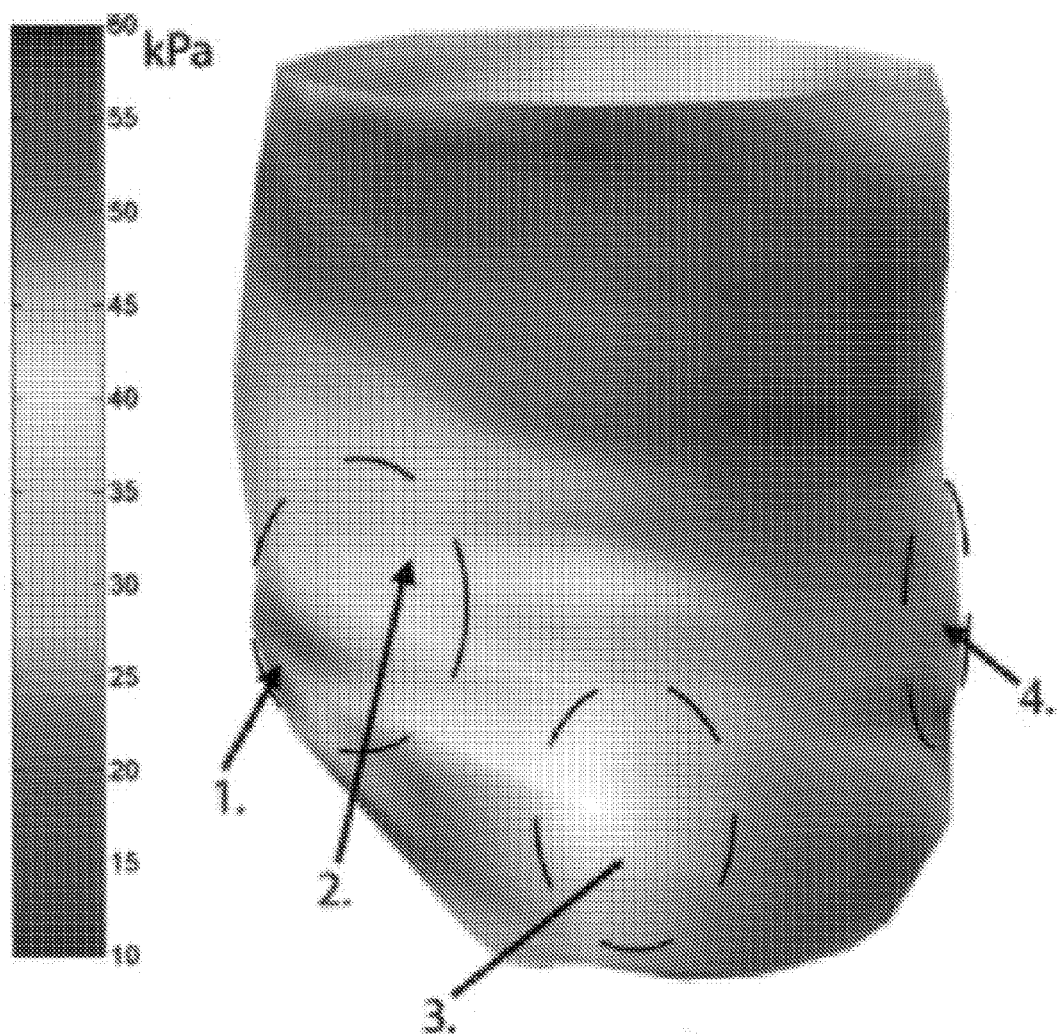
FIG. 16B. Mid wall fiber stress in simulation with the injection of 4.4 mL of material to the border zone in 4 noted locations FIG. 16C. Stress difference between the control and treatment simulations that demonstrates location of stress reduction in relation to injection sites (arrows).
Figure 16C:
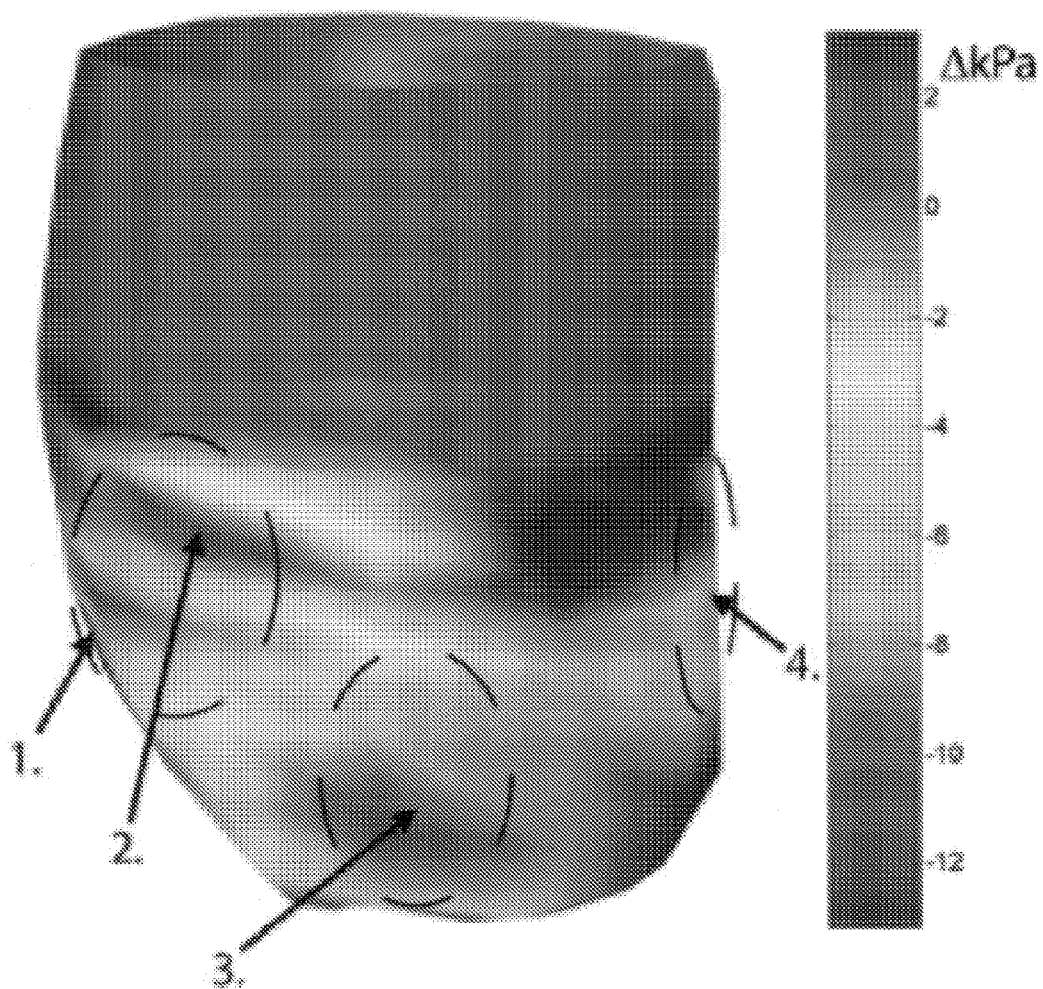
FIG. 16 Representation of ventricular fiber stress as a function of position in the heart.

FIG. 16 shows a three-dimensional color representation of mean end-systolic fiber stress before (A) and after (B) the injection of material to the ventricle wall, with yellow-red indicating areas of elevated fiber stress compared to the rest of the ventricle. FIG. 16 also shows the difference between the two (C), with blue regions indicating areas of decreased stress as a result of the model changes. Changes in stress are localized in the regions of injection simulation.

Figure 17A:
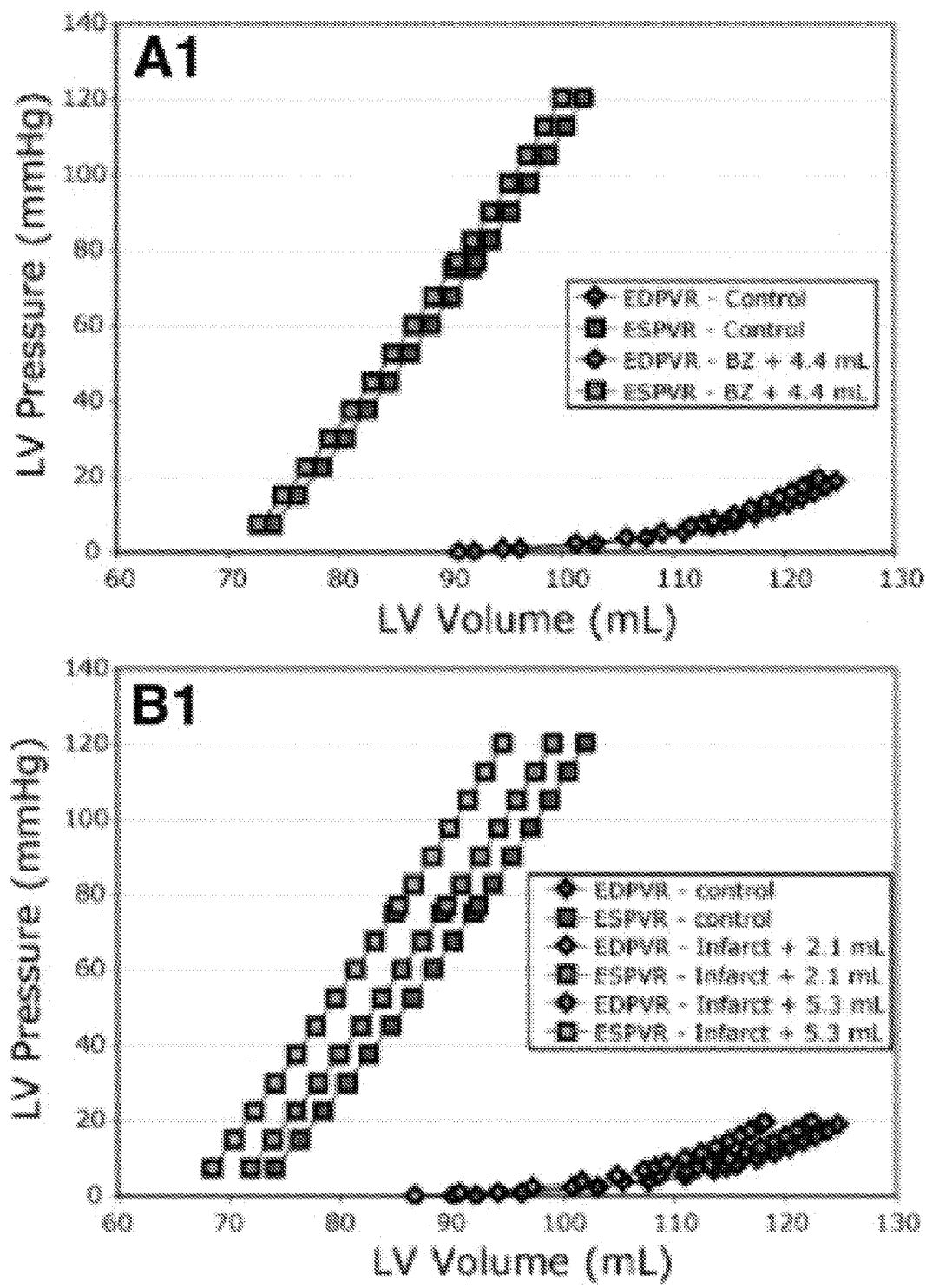
FIG. 17 Top: Cardiac function for the pen-infarct border zone injection simulation. End-systolic and end-diastolic pressure-volume relationships (FIG. 17A), and stroke volume versus $P_{ED}$ (FIG. 17B) and $V_{ED}$ (FIG. 17C). Bottom: Cardiac function for the dual infarct injection simulation. End-systolic and end-diastolic pressure-volume relationships (FIG. 17A), and stroke volume versus $P_{ED}$ (FIG. 17B) and $V_{ED}$ (FIG. 17C).
Figure 18:
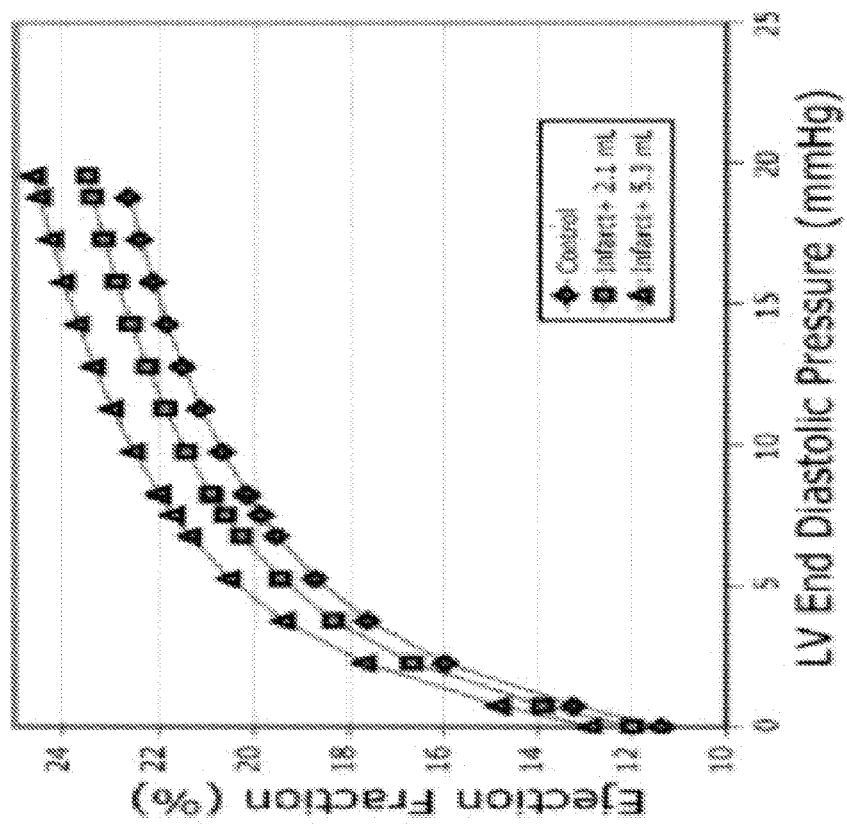
FIG. 18 EF as a function of end-diastolic pressure for the simulated injection of non-contractile volume to the border zone (A) and infarct (B) region. Little observed difference is seen in the border zone injection, but in the infarct a 2% increase in wall volume produces a 1 percentage point increase in EF over control simulations, while a 5% increase in wall volume creates a 2 percentage point increase in EF.
Figure 18:
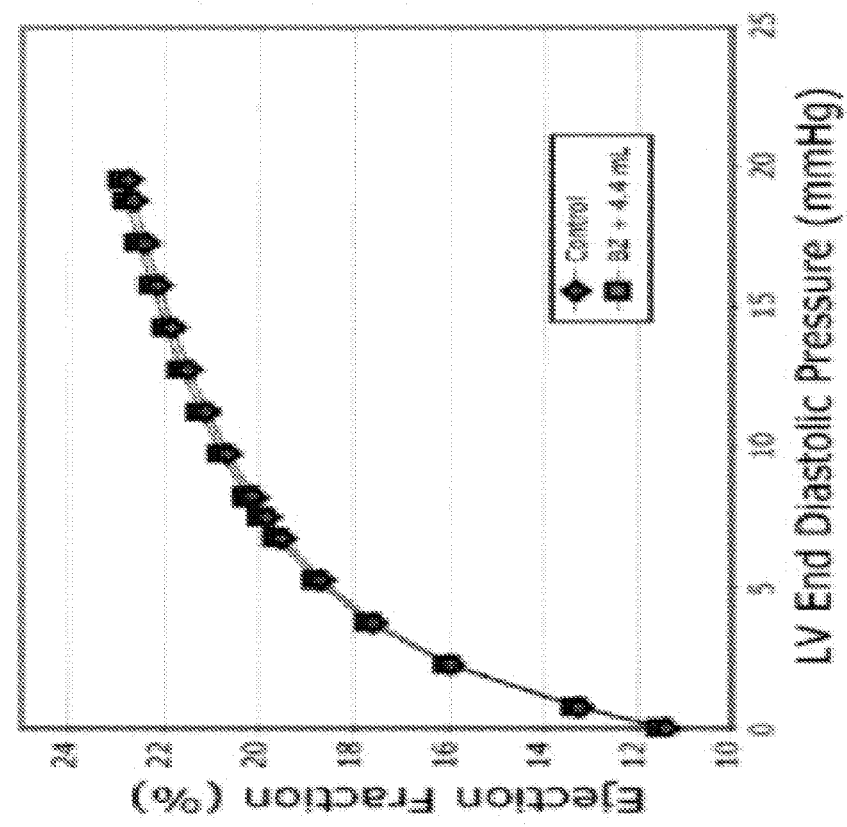

In addition, material addition to the border zone in this simulation caused slight shifts to both the ESPVR and EDPVR (FIG. 17A1). Meanwhile, global heart function as estimated by $SV/P_{ED}$ was not significantly altered by the model changes, with the multiple injections providing no change over the control simulation (FIG. 17A2). $SV/V_{ED}$ (FIG. 17A3) and ejection fraction (FIG. 18) were only slightly altered.

Figure 17B:
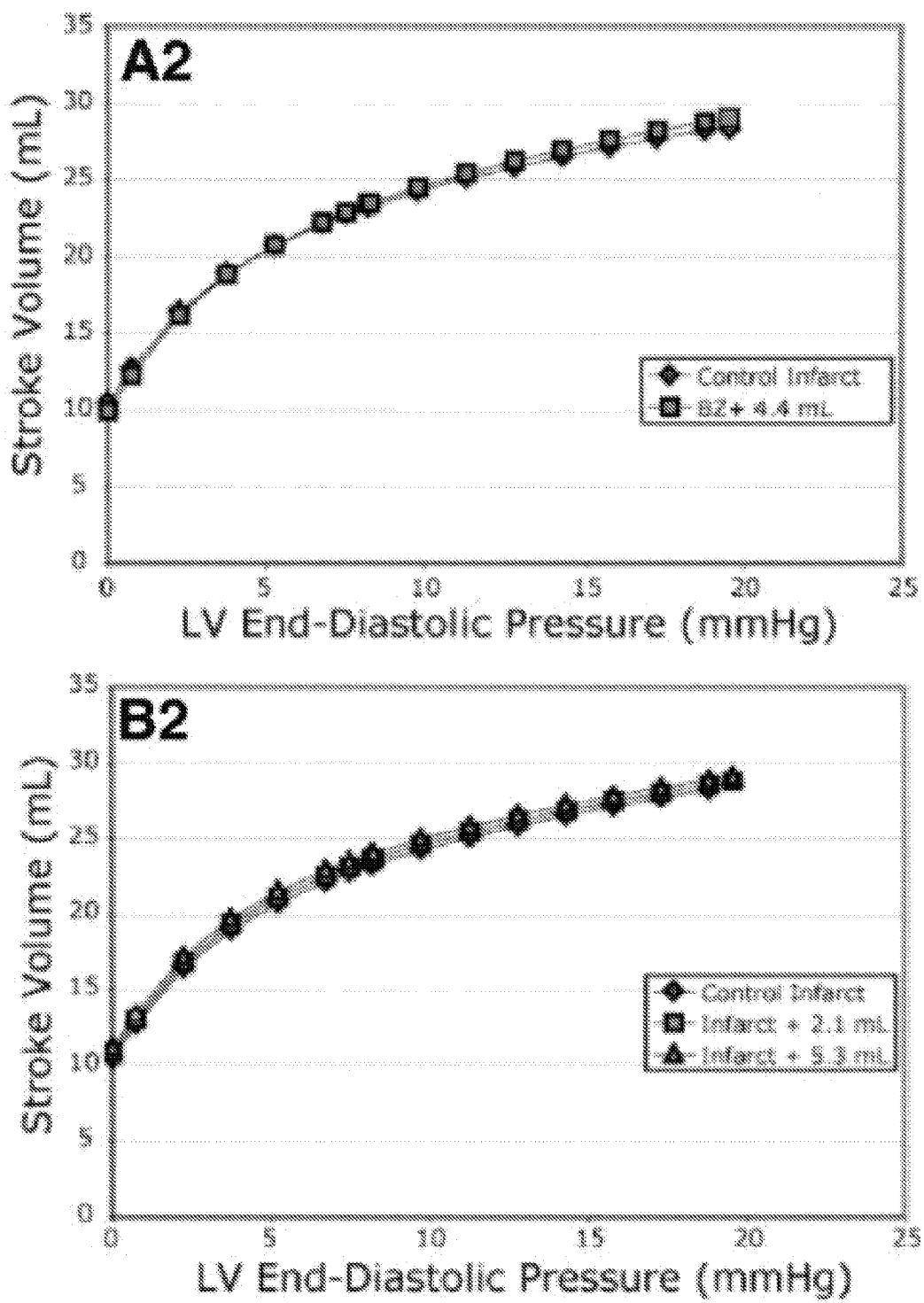
Figure 17C:
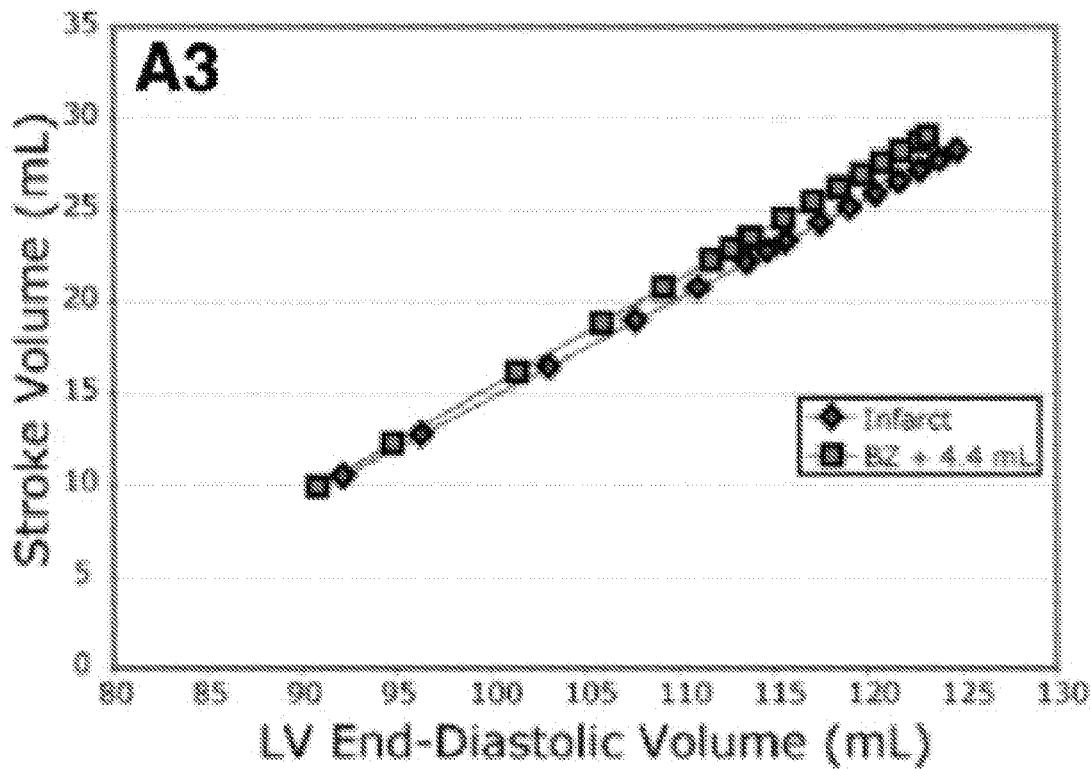
Figure 17C:
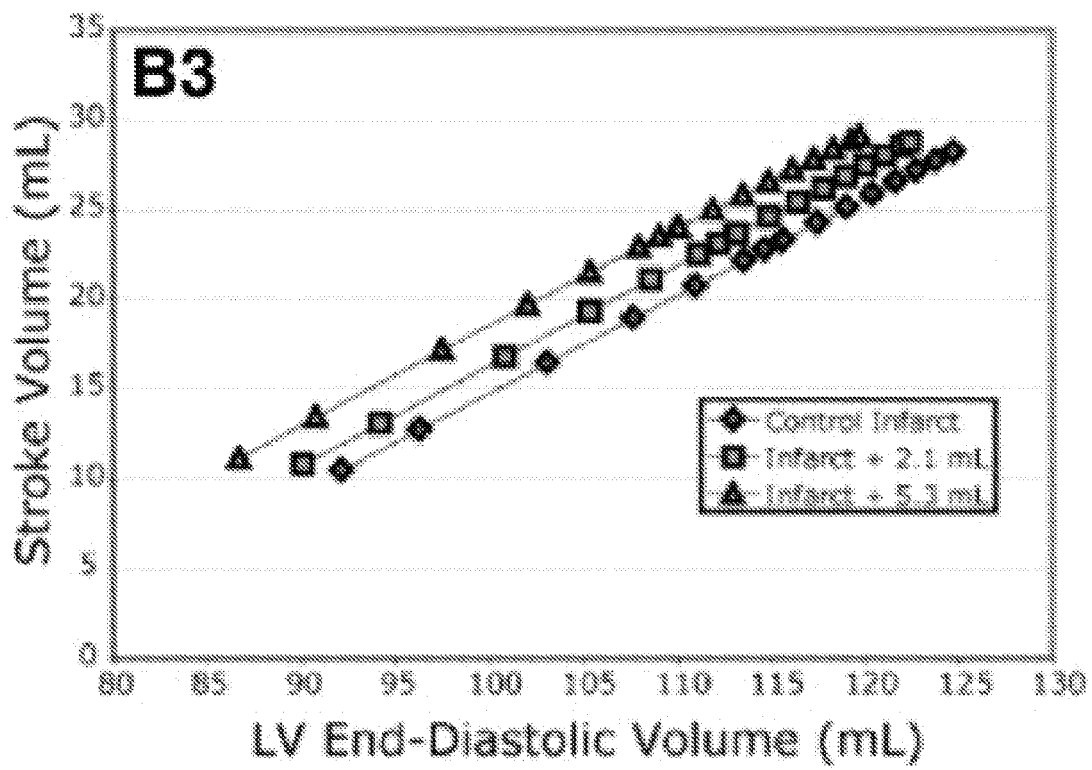

Simulated Injection into Anterior and Posterior Infarct:

Results show that direct injection of material to the infarct region can alter the EDPVR and ESPVR proportionally to the amount added (FIG. 17B1), moving the EDPVR and ESPVR leftward, with a slight upward change to the slope of the ESPVR. These changes result as a combination of 2 factors, the increased elastance of the ventricle from added material and the changes to ventricular volume. While not significantly altering the $SV/P_{ED}$ relationship (FIG. 17B2), these geometric changes can lead to observed differences in $SV/V_{ED}$ relationship (FIG. 17B3) and the often-reported metric EF (FIG. 18B). A modest fractional increase in volume of the infarct (5.3 mL compared to a 97 mL total wall volume) is capable of increasing the EF by approximately 2 percentage points over the infarct control (24 versus 22) or 10%.

Our studies demonstrate that a small fractional change (0.5-5%) in myocardium wall volume can alter cardiac mechanics; decreasing wall stresses, affecting ESPVR and EDPVR, and increasing EF and $SV/V_{ED}$ without improving $SV/P_{ED}$. These acute mechanical effects are dependant on the location of the injection, the fractional volume of material added and its relative stiffness to the local myocardium. In view of practical considerations, the direct injection of material into the beating myocardium will likely result in significant losses (upwards of 50%) due to material being expelled during the cardiac cycle or poor cellular engraftment, the range of 0.5-5% chosen for the described simulations therefore represents a realistic clinical scenario of added non-contractile volume to the LV wall.

As such, tje mechanical changes in ventricular performance that these small volume additions bring about have important implications for tissue engineering applications. As previously stated, wall thickening achieved by application, e.g. injection, and integration of a cell population or the use of an in-situ forming prosthetic structure can help normalize cardiac wall stress in an injured ventricle.

The stress reduction potential of injected material is highly significant, as in a dyskinetic transmural infarct, the elevated stresses in the infarct border zone region can contribute significantly to pathological remodeling in the post infarct heart. Reducing these stresses in turn minimizes stress induced apoptosis and border zone extension and expansion, reducing further remodeling and preventing the progression into CHF. Although the average level of stress reduction is on the order of 2094, it is important to note that the resulting border zone fiber stress levels are equivalent to those calculated in the remote region. The reduction of one fiber stress component in this sensitive area provides an effective means to mitigate post infarct loss of cardiac function.

The finite element models described herein clearly demonstrate the global pressure-volume relationships, the $SV/V_{ED}$, and the often-reported cardiac metric, EF, can be affected by adding a physiologically acceptable material and the benefits obtained therefrom when the prosthetic structure is properly positioned.

Tuning the Constitutive Parameters

The constitutive parameters of the materials of the present invention can be tuned for optimizing self-renewal, differentiation, and/or proliferation of transplanted or native cells for the myocardial applications described herein. In some embodiments, one independent parameter in the materials described herein can be tuned based on in vivo or ex vivo data. In other embodiments, a plurality of independent parameters of the materials is independently tuned based on in vivo or ex vivo data. Exemplary tunable properties include, without limitation, biochemical properties, or signaling ligands that the material presents to the cells, and the physical properties, e.g. stiffness, which depends on the degree of crosslinking of the polymer network. To optimize self-renewal, differentiation, or proliferation, methods such as response surface methodology can be employed to design experiments independently varying the biochemical and mechanical properties of the material.

In preferred embodiments, IPNs and sIPNs are used to form the prosthetic structure or cellular matrix support of the invention. As those of skill in the art will discern from the foregoing disclosure on methods of forming the materials of the invention, these IPNs and sIPNs can adopt any of a large range of mechanical and biochemical properties. Depending on the temperature, identity and concentration of the network components, mechanical properties such as the shear modulus (G), Young's modulus (E), complex shear modulus, complex Young's modulus, and loss angle can be manipulated. Depending on the identity and concentration of the network components, ligand density, ligand type and method of ligand attachment, biochemical properties such as biological interactions (fouling), cell growth, differentiation, and rates of growth and differentiation, can be manipulated.

In an exemplary embodiment, the ligand has a density in the network of from 0.1 pmol/cm.sup.2 to 20 pmol/cm$^2$. In an exemplary embodiment, the density is from 0.1 to 0.5. In an exemplary embodiment, the density is from 0.1 to 1. In an exemplary embodiment, the density is from 1 to 8. In an exemplary embodiment, the density is from 5 to 20. In an exemplary embodiment, the density is from 5 to 14. In an exemplary embodiment, the density is from 0.5 to 9.

In an exemplary embodiment, the ligand has a density in the network of from 50 µM to 500 µM. In an exemplary embodiment, the ligand has a density in the network of from 75 µM to 400 µM. In an exemplary embodiment, the ligand has a density in the network of from 100 µM to 240 µM. In an exemplary embodiment, the ligand has a density in the network of from 350 µM to 500 µM. In an exemplary embodiment, the ligand has a density in the network of from 175 µM to 375 µM. In an exemplary embodiment, the ligand has a density in the network of from 290 µM to 500 µM.

A modulus is a constant or coefficient which expresses the measure of some property, such as elasticity, and can be used to relate one quantity, such as imposed force or stress, to another, such as deformation or strain.

Young's modulus, also known as elastic modulus, (E) is a material property that reflects the resistance of a material to tensile axial deformation. It is defined as the rate of change of tensile stress with tensile strain in the limit of small strains.

As opposed to axial strain, in which deformation of a plane occurs in a direction perpendicular to the plane, shear strain is characterized by deformation in a direction parallel to the plane. There is a resulting shape change without a corresponding volume change.

Shear modulus (G) is an analogous but independent material property that reflects the resistance of a material to shear deformation. It is defined as the rate of change of shear stress with shear strain at small strains.

In some exemplary embodiments, the network has a shear modulus of from 300 Pa to 50 kPa. In an exemplary embodiment, the network has a shear modulus of from 400 Pa to 30 kPa. In an exemplary embodiment, the network has a shear modulus of from 1 kPa to 25 kPa. In an exemplary embodiment, the network has a shear modulus of from 2 Pa to 17 kPa. In an exemplary embodiment, the network has a shear modulus of from 30 Pa to 50 kPa. In an exemplary embodiment, the network has a shear modulus of from 16 Pa to 45 kPa.

Exemplary materials of the invention are able to undergo a shift between a first state and a second state upon a change in their environment. For example, selected materials of the invention shift between a first state and a second state upon a change in the ambient temperature to which the material is exposed. In exemplary embodiments, one of the states more closely in resembles a natural ECM in one or more properties than the other state. For example, in functional terms, in one state a stem cell population proliferates essentially without differentiating; in the second state, the stem cell population differentiates.

As an example, a physical and/or chemical property of a network of the invention is exploited to mimic the native matrix surrounding stem cells (extracellular matrix, ECM). An exemplary property that can be manipulated is the water content of the network of the invention. Networks with differing water contents can be designed to mimic an ECM. For example, selected networks of the invention include a water content of at least about 20%, preferably, at least about 50% and still more preferably, at least about 70%. A selected hydrogel of the invention is designed to have a water content approximately that of the relevant ECM.

In another embodiment, there is provided a network that is shiftable between a first water content and a second water content. IPNs and sIPNs according to this design can be shifted between the first state and the second state, thereby controlling stem cell destiny. In general, one of the two states will more closely resemble an ECM than the other. Thus, for example, the material with the stem cells bound thereto can be shifted from the first state in which the cell population is essentially non-differentiated into the second state, more closely mimicking an ECM, inducing the stem cells to commit to a lineage. The invention also provides a material that undergoes a change in a modulus upon perturbation of its surroundings. In an exemplary embodiment, the modulus is selected from the shear modulus of the material, its tensile modulus and combinations thereof.

In an exemplary embodiment, the invention provides a material having a shear modulus of about 100 Pa to 5 kPa. Selected IPNs and sIPN have a modulus of about 50 PA in the first state and a modulus of about 400 PA in the second state. An example of a polymer that undergoes approximately this sort of phase change is a sIPN that includes a thermoresponsive polymer. The condition that promotes the first state is a temperature approximately room temperature (e.g., about 25° C.), while that promoting the second state is a temperature that is approximately human body temperature (e.g., 37° C.). HANDBOOK OF BIOMATERIAL PROPERTIES, Editors J. Black and G. Hastings, Chapman & Hall, (1998).

For example, selected IPNs and sIPNs of the invention are extremely pliable and fluid-like at room temperature (RT), but demonstrate a phase transition as the IPN or sIPN warms from RT to body temperature, yielding more rigid structures. Thus, the networks offer the benefit of in situ stabilization without the potential adverse effects of in situ polymerization (e.g., residual monomers, initiators, catalysts, etc.). The networks of the invention are preferably injectable through a syringe with about a 2 mm-diameter aperture without appreciable macroscopic fracture, are functionalized or amenable to functionalization with ligands that interact with cell surface receptors. An exemplary network is functionalized with a ligand that binds to a cell surface receptor, and the material supports cell proliferation in vitro when seeded with cells.

The networks of the invention are tunable in terms of their delivery, and dosing of a therapeutic species (e.g., stem cells). The mechanical and biochemical properties of the materials of the invention are also tunable.

In yet another exemplary embodiment, the invention provides an IPN or an sIPN that exists in a state in which it is readily deployable by minimally invasive methods. Accordingly, at room temperature (i.e., approx. 20-27° C.) these IPNs or sIPNs are flowable, e.g., injectable through a small diameter aperture (from about 1 mm in diameter to about 5 mm in diameter), and are essentially free of macroscopic fracture following injection. Exemplary IPNs or sIPNs of the invention shift from the flowable state to a more rigid, less flowable state upon being heated. The shift preferably occurs at a temperature that is approximately a mammalian body temperature, e.g., 37° C.

To make a biomimetic sIPNs, a diverse array of crosslinking reagents and strategies can be used. Crosslinking exploiting orthogonal chemistry may have distinct advantages over free radical polymerization: 1) biocompatibility is increased since no free radicals are used during sIPN synthesis; 2) stem cells or other cells can be encapsulated during sIPN synthesis; and, 3) sIPN synthesis uses an "orthogonal" chemistry that is not reactive to the cell surface thereby allowing only the full ligand definition in the cell microenvironment. For example, if we activate pAAc chains with maleimide terminated grafts of EMCH, these chains can be reacted with any dithiol-containing molecule to generate a crosslinked network or sIPN. In the example below, we used di-thiol pEG and HyA chains with maleimide terminated grafts of EMCH; however, any other dithiol would suffice, including the MMP degradable peptides with a cysteine group at both ends. Candidate chemistries other than thiol-maleimide include, BrdU-thiol, phosphine-azide linkages via Staudinger ligation, and ketone-aminooxy linkages (as reviewed in Prescher and Bertozzi, Nature Chemical Biology 1, 13-21 (2005)). Also, differing chemistries at opposing ends of the crosslinking chain can be used. One example of a crosslinking chain that carries two different chemistries would be a Phosphine-Asp-Tyr-Lys-Asp-Asp-Asp-Asp-Lys-Cys peptide (phosphine-FLAG-Cys). Mixing this peptide with polymer chains that are activated with azide groups and with polymer chains activated with maleimide groups forms a gel in mild reaction conditions. Lastly, a sIPN can be grafted directly to cell receptors during sIPN synthesis by alternate chemistries if desired.

In exemplary embodiments having two independent parameters, self-renewal, differentiation, or proliferation of the cell population in vivo or ex vivo is measured. The results of the series of experiments can be represented in a graphical map (i.e., surface) of cell response as a function of biochemistry and mechanics. Response surface analytical methods known in the art can then be applied to identify the combination of biochemistry and mechanics that optimizes (i.e., a peak or maximum in the response surface) the ability of the material to control a desired cell response (i.e., self-renewal, differentiation, proliferation). Information provided by such models can in turn be used by those of ordinary skill in the art to enhance the survival and maintenance of transplant or native cells in the actual host environment, e.g. injured myocardium in a patient to be treated.

In alternative embodiments of the above methodology, one parameter, e.g. biochemical, is held constant while the other parameter(s), e.g. mechanical, are systematically varied across a range. Each of the plurality of parameter(s) can be independently held constant at systematically varied values of other parameters to provide one or a plurality of maps using response surface methods known in the art. Surface response analysis can then be applied to identify the combination of independent parameters for optimizing the material's ability to promote the desired cell response.

In some embodiments of the invention, the physical parameter being tuned is stiffness. In additional embodiments, the physical parameter is measured as complex modulus of the material.

The materials, methods and devices of the present invention are further illustrated by the examples, which follow. These examples are offered to illustrate, but not to limit the claimed invention.

EXAMPLES

Example 1

The present example details the formation of an IPN to stimulate neural stem cell proliferation incorporating bsp-RGD(15), selected from the cell-binding of bone sialoprotein (BSP), to accelerate proliferation of rat hippocamal neural stem (NSC) cells in contact with the peptide modified p(AAm-co-AAc) hydrogels. FIG. 1 provides an example of an IPN that incorporates a peptide from laminin A chain, 1am-IKVAV(19).

The materials used to synthesize the IPN include the following: Acrylamide (AAm), poly(ethylene glycol) 1000 monomethyl ether monomethacrylate (PEG1000MA), acrylic acid (AAc), and N,N'-methylenebis(acrylamide) (BIS; Chemzymes ultrapure grade) were purchased from Polysciences, Inc. (Warrington, Pa.). N-hydroxysulfosuccinimide (sulfo-NHS), 2- N-morpholino) ethanesulfonic acid, 0.9% sodium chloride buffer (MES), and sulfosuccinimidyl 4- (N-maleimidomethyl)cyclohexane-1-carboxylate (sulfo-SMCC) were acquired from Pierce (Rockford, Ill.). QTX ([3-(3,4-Dimethyl-9-oxo-9H-thioxanthen-2-yloxy)-2-hydroxypropyl] trimethylammonium chloride) was obtained from Aldrich (Milwaukee, Wis.). Allyltrichlorosilane (ATC) was obtained from Gelest (Morrisville, Pa.). Diamino-poly (ethylene glycol) [3400-PEG($NH_2$)$_2$; 3400 g.mol$^{-1}$, Chromatographically pure] was purchased from Nektar (Huntsville, Ala.). All peptides were synthesized by American Peptide Co. (Sunnyvale, Calif.) and characterized using mass spectrometry and high performance liquid chromatography (purities>95%). RGD or RGE peptides were based off the integrin-binding sequence from rat bone sialoprotein: (bsp-RGD(15) peptide (SEQ ID NO: 1); bsp-RGE(15) peptide (SEQ ID NO: 3); bsp-RGD(15)-FITC) (SEQ ID NO: 2)_ (Note that bsp-RGD(15) peptide is the same as 1-RGD as described previously (Harbers, et al., Langmuir, 21(18):8374-8384. (2005); (Harbers et al., Journal Of Biomedical Materials Research Part A, 75A(4):855-869 (2005)). The 1am-IKVAV(19) peptide was from laminin A chain (amino acids 2091-2108, i.e. laminin peptide PA222): CSRARKQAASIKVAVSADR (SEQ ID NO: 7). Polystyrene 8-well strips (Costar #2580) and 35 mm tissue culture polystyrene dishes were purchased from Fisher Scientific (Santa Clara, Calif.). For characterization by quartz crystal microbalance with dissipation monitoring (QCM-D), quartz sensor crystals were purchased from Q-sense (Newport Beach, Calif.). All other chemicals used were reagent grade and used as purchased without further purification. All glassware was cleaned as described previously (Irwin, et al., Langmuir, 21(12):5529-36 (2005)).

The synthesis of the polymeric networks is separated into two parts: first the monomers are polymerized on a polystyrene surface to create an IPN; subsequently, the IPNs are functionalized with a biomolecule of interest. In short, AAm was crosslinked (BIS) and grafted to a oxygen plasma cleaned, polystyrene 8-well strip surface using a water soluble photoinitiator, QTX. The IPN was formed by subsequent UV-initiated polymerization of the crosslinked (BIS) network of EG/AAc. The modulus of the IPN can be controlled by adjusting the concentration of crosslinker, in either stage. A diamino-PEG spacer chain was coupled to the AAc sites using carbodiimide reaction chemistry and finally functionalized with the -RGD-peptide via a heterobifunctional cross-linker.

1.1 Synthesis of the p(AAm-co-EG/AAc) IPNs

The synthesis of the polymeric networks is separated into two parts: first the monomers are polymerized on a polystyrene surface to create an IPN; subsequently, the IPNs were functionalized with a biomolecule of interest. In short, AAm was crosslinked (BIS) and grafted to an oxygen plasma cleaned, polystyrene 8-well strip surface using a water soluble photoinitiator, QTX. The IPN was formed by subsequent UV-initiated polymerization of the crosslinked (BIS) network of EG/AAc. The modulus of the IPN can be controlled by adjusting the concentration of crosslinker, in either stage (see, Example 2). A diamino-PEG spacer chain was coupled to the AAc sites using carbodiimide reaction chemistry and finally functionalized with the -RGD-peptide via a heterobifunctional cross-linker. Polymerization and conjugation details can be found elsewhere (Harbers, et al., Langmuir, 21(18):8374-8384. (2005)), but are described briefly below.

Specifically, all reactions were carried out at room temperature unless otherwise stated. Polystyrene surfaces were cleaned by submersion in a 5 M NaOH ethanol/ASTM Reagent grade I water (water) solution (v/v, 70/30) for 1 h, rinsed, and sonicated (30 min) in water (Branson model 5510, 40 kHz, 469 W, 117 V). After cleaning, the samples were dried ($N_2$) and activated with an oxygen plasma. The IPN was then grafted to PS using a two-step sequential photopolymerization similar to previously published protocols. After an 8-10 min AAm solution (0.1485 g/mL AAm, 0.0015 g/mL BIS, 0.01 g/mL QTX, 0.03 mL/mL isopropyl alcohol, 0.97 mL/mL water) adsorption, the samples underwent QTX photoinitiated free radical polymerization using a transilluminator table (model TFL-40; Ultra-Violet Products, Upland, Calif.) for 4.5 minutes. The power of the table was measured at 2.3 mW/cm$^2$ using a radiometer (International Light, Inc., Massachusetts) with a band-pass filter (352-377 nm). Following polymerization, excess homopolymer was aspirated and the samples were placed in water (>10 min), rinsed, and sonicated (water, 5 min). After sonication, the samples were rinsed (water) and dried ($N_2$). An IPN of p(AAm-co-EG/AAc) was then formed (FIG. 1A) after the pAAm layer was exposed to an 810 min PEG/AAc solution (0.0200 g/mL PEG, 0.0100 g/mL BIS, 0.005 g/mL QTX, 0.0162 mL/mL, 0.5 mL/mL isopropyl alcohol, 0.5 mL/mL water) and subsequent photoinitiated polymerization for 6 minutes. Following the formation of the IPN, the samples were treated as they were after pAAm grafting.

1.2 Peptide Modification to the IPN

To functionalize the p(AAm-co-EG/AAc) IPN with biological ligands, the IPN was first equilibrated with buffer (>30 min, MES, 0.5 M, pH 7) and then 3400-PEG(NH$_2$)$_2$ spacer chains were grafted to the AAc sites via a carbodiimide reaction (60 min, MES, 0.5 M, pH 7, 0.150 g/mL 3400-PEG (NH$_2$)$_2$, 0.005 g/mL EDC, 0.0025 g/mL Sulfo-NHS). After the reaction, the solution was aspirated and the samples were rinsed 2× with 0.1M MES buffer (pH 7.0) followed by 2× with 50 mM sodium borate buffer (pH 7.5). To couple bioactive molecules to the PEG(NH$_2$)$_2$-modified IPN, the heterobifunctional cross-linker, sulfo-SMCC, was reacted with the free amine on the PEG(NH$_2$)$_2$ chains (0.0005 g/mL Sulfo-SMCC, pH 7.5, borate buffer). The solution was then aspirated, and the samples were rinsed 2× with borate buffer followed by 2× with peptide-coupling buffer (sodium phosphate, 0.1M, pH 6.6). Finally, the peptide containing a free thiolthe N-terminus [i.e., bsp-RGD(15), bsp-RGE(15), or 1am-IKVAV(19)] was coupled (0-20 µM) to the maleimide (sulfo-SMCC). Following the reaction, the solution was aspirated and the samples were rinsed 4-5 times with coupling buffer, sonicated (water, 5 min), rinsed (water), and dried (N$_2$). Samples were removed at each stage and stored in an N$_2$ ambient environment for up to 1 year.

1.3 Characterization of IPN

To analyze the IPN chemical and mechanical properties of the IPN, X-ray photoelectron spectroscopy (XPS), fluorescently-tagged ligands, and quartz crystal microbalance with dissipation monitoring (QCM-D) were used. After each step of synthesis, XPS peak intensity ratios (i.e., O/N and C/N) indicated that the IPN coated the poly(styrene) substrate, while angle-resolved studies demonstrated that the pAAm and PEG/AAc networks were interpenetrating as previously described. XPS spectra were recorded using a PHI5400 instrument (Physical Electronics, Chanhassen, Minn.) with a non-monochromatic Mg anode as the X-ray source at a take-off angle of 55° using the same method as described elsewhere (Harbers, et al., *Langmuir,* 21(18):8374-8384. (2005); (Barber, et al., *Biomaterials,* 26(34):6897-905 (2005)).

Figure 1B:
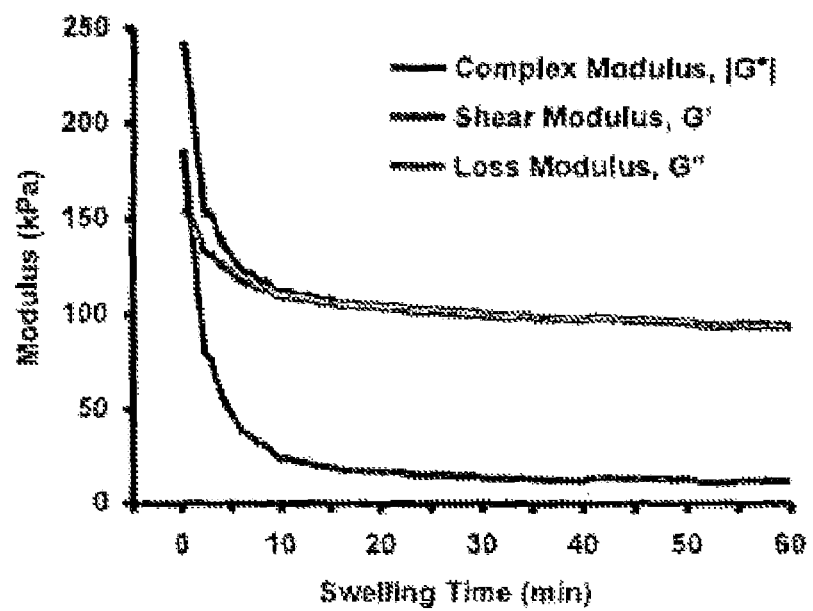
Figure 1C:
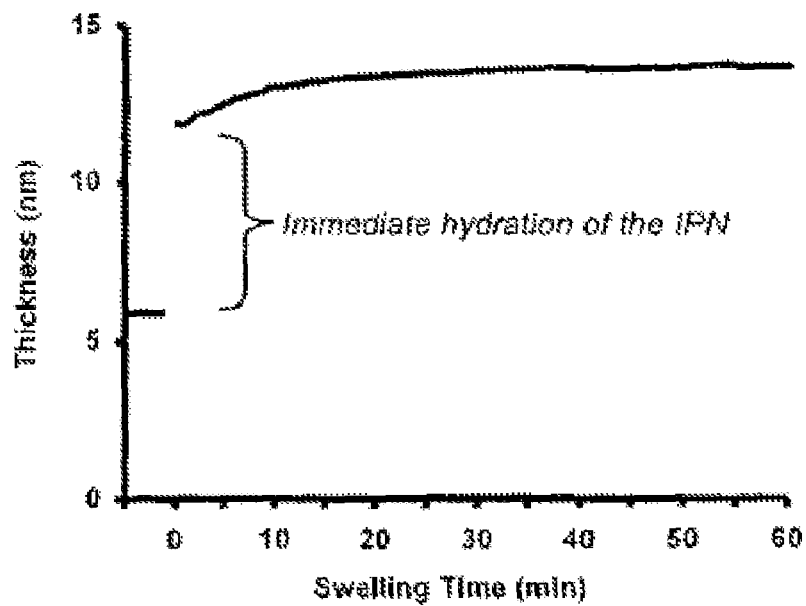
Figure 1D:
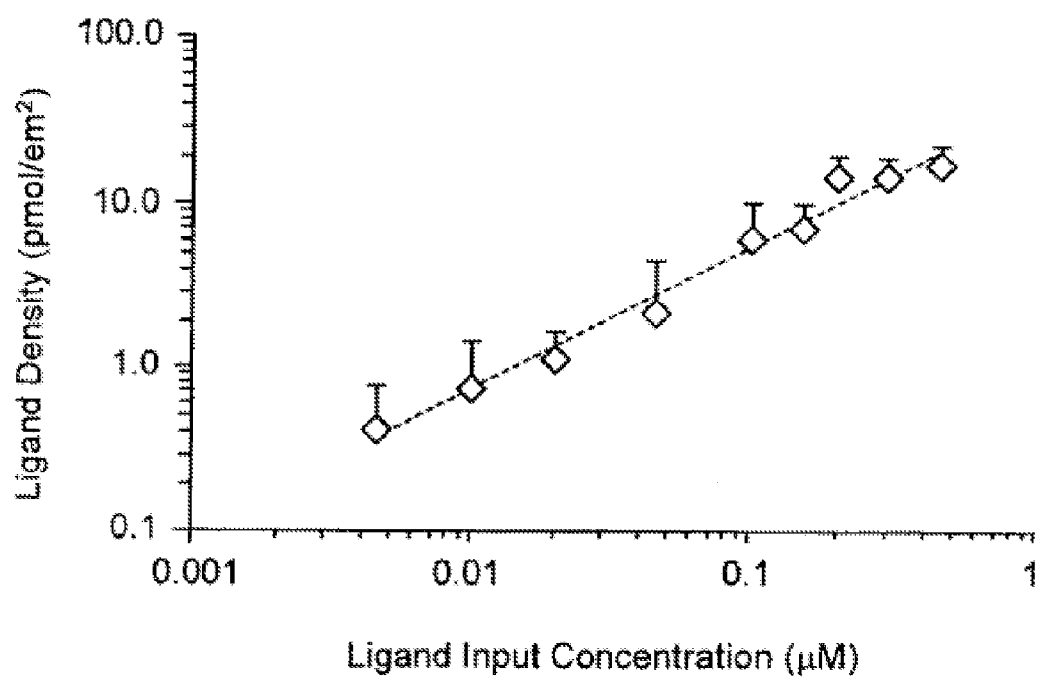
Figure 2:
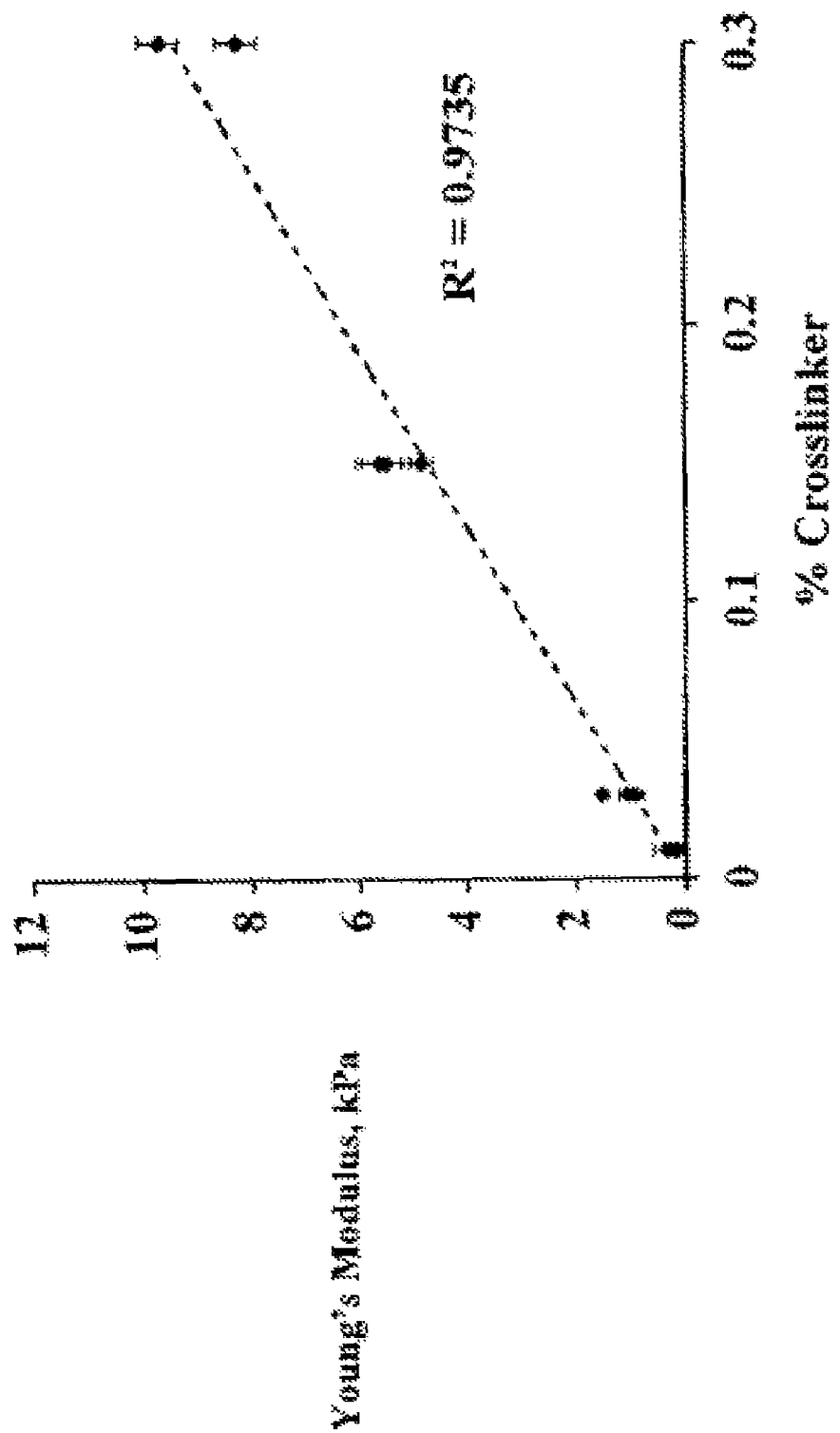
FIG. 2 depicts the change in the Young's modulus (E) as the concentration of BIS is used in the polymerization of the AAm layer is varied. The E of the gels varied linearly from 0.23±0.09 kPa to 9.86±0.14 kPa, and the square of the correlation coefficient ($R^2$) is 0.9735.

IPN physical properties, specifically thickness as well as shear storage and loss moduli, were measured by modeling QCM-D frequency and dissipation changes upon swelling of the IPN in phosphate buffered saline (PBS) (Irwin, et al., *Langmuir,* 21(12):5529-36 (2005)) (FIG. 1*b-c*). Upon exposure to PBS, the IPN swelled immediately to ~12 nm and was non-fouling (i.e., low protein adsorption) to media components (Irwin, et al., *Langmuir,* 21(12):5529-36 (2005)). The surfaces of the QCM-D sensor crystals were modified for characterization with an IPN of p(AAm-co-EG/AAc) as described herein, except that a unsaturated silane was chemisorbed to the surface prior to the polymerization step as described previously (Irwin, et al., *Langmuir,* 21(12):5529-36 (2005)). Briefly, sensor crystals are coated with 200 nm of silicon/silicon dioxide (Si/SiO$_2$), and then an unsaturated organosilane, ATC, was grafted onto the Si/SiO$_2$ surfaces by soaking them in a 1.25% (v/v) solution of ATC in anhydrous toluene (prepared in a glovebox) for 5 min. After baking them for 30 min at 125° C., the IPN synthesis of p(AAm-co-EG/AAc) proceeded as described herein. A QCM-D D300 (Q-sense) was used in this study, as described in detail elsewhere (Irwin, et al., *Langmuir,* 21(12):5529-36 (2005)).

Briefly, in a QCM-D experiment, four separate resonant frequencies (overtones, n) were used to drive oscillation of the shear wave through the crystal: ~5 MHz (fundamental overtone, n=1), ~15 MHz (n=3), ~25 MHz (n=5), and ~35 MHz (n=7). The applied voltage for each resonant frequency was sequentially pulsed across the sensor crystal, allowing shear wave dissipation with the simultaneous measurement of the absolute dissipation (D) and the absolute resonant frequency (f) of the crystal for all four overtones. All measurements were taken at 37° C. The f and D values were recorded for the crystals before and after ex situ modification both dry and in PBS. Dry thickness was calculated via the Sauerbrey relationship, $\Delta M = -C \cdot \Delta f \cdot n^{-1}$, where $\Delta M$ was the total change in mass of a rigid, elastic adlayer, C was a 17.7 ng.cm$^{-1}$.Hz$^{-1}$ constant based on the physical properties of the quartz crystal, and n was the overtone number. The IPN surfaces were swollen in PBS (sample size of 3). Degassed PBS was introduced into the measurement chamber, and the chamber was sealed shut during the 16 hr swelling period. For protein adsorption studies, proliferation or differentiation media (see neural stem cell culture) was introduced for 1 hr, and then rinsed twice with PBS for 5 min.

FITC-labeled peptides were used in several IPN preparations to determine the surface density of bioactive peptides as a function of the amount of soluble peptide added to the surface conjugation reaction (data not shown), which allowed subsequent fine-tuning of peptide surface density. Peptide density and degradation analysis of such surfaces have been characterized elsewhere (Harbers, et al., *Langmuir,* 21(18): 8374-8384. (2005); (Harbers et al., *Journal Of Biomedical Materials Research Part A,* 75A(4):855-869 (2005)) (Irwin, et al., *Langmuir,* 21(12):5529-36 (2005); (Barber, et al., *Biomaterials,* 26(34):6897-905 (2005)).

The density of a biologically relevant ligand was measured after grafting to the IPN. A fluorescence assay was developed to quantify ligand density on IPN modified surfaces. (Harbers, et al., *Langmuir,* 21(18):8374-8384. (2005)). Samples were modified by substituting bsp-RGD(15)-FITC for bsp-RGD(15). Surfaces lacking the SMCC cross-linker were used as controls to ensure that signal from entrapped or non-specifically adsorbed fluorophore could be subtracted as background. Following the IPN synthesis, samples were dried (N$_2$) and either stored under nitrogen or immediately prepared for measurement. To improve quantum efficiency, 10 µl of ligand coupling buffer were added to each dried sample well to form a hydrated thin IPN. Samples were then inverted and immediately read using a Spectramax GeminiXS spectrofluorometer (Molecular Devices, CA; ex/em/cutoff, 485/538/530 nm)). Density standards were generated by adding 50 µL of RGD-FITC solutions prepared in water to PEG (NH$_2$)$_2$ modified wells and drying under vacuum for >2 hrs to form a dried film of known ligand density (0.11 to 37.15 pmol/cm$^2$). After drying, density standards were treated the same as experimental wells. Figure xx shows the ligand density data for RGD-FITC coupled to the IPN surface as a function of input concentration. Figure xx represents the data on a log-log scale demonstrating the linear control of ligand density based on solution input concentration. These results demonstrate that ligand density saturated at ≈20 pmol/cm$^2$ at input concentrations≧0.46 mM. These results are in agreement with an independent fluorescent density measurement technique that relies on enzymatic cleavage and subsequent release of the surface bound FITC labeled peptide into solution. (Harbers et al., *J Biomed Mater Res A,* (2005)). Given the close agreement between these two independent methods, the fluorescent technique used was an effective, sensitive, and simplistic method to measure ligand densities on the IPN.

Therefore, the peptide-modified IPN ligand density (1.2-21 pmol/cm$^2$), hydrated thickness (14 nm), swelling behavior (polymer volume fraction, $v_{2s}$=0.43), complex shear modulus ($|G^*|$=94 kPa), and non-fouling properties define a specific cellular microenvironment, namely by specifying the dose and mechanical context of the chemical signals presented to stem cells.

Example 2

This example details the creation of IPN coatings of varying stiffness to investigate the combined effects of substrate modulus and ligand density on stem cell self-renewal and fate determination. The materials used in this synthesis were the following:
methacryloxypropyltrimethoxysilane (MPMS) obtained from Gelest (Morrisville, Pa.); acetic acid (AA), acrylamide (AAm), bisacrylamide (Bis), N,N,N',N'-tetramethylethylenediamine (TEMED), poly(ethylene glycol) monomethyl ether monomethacrylate, MW 1000) (PEGMA), camphorquinone (CQ), acrylic acid (AAc), and 3400 MW diamino-PEG [PEG(NH$_2$)$_2$] obtained from Polysciences (Warrington, Pa.); ammonium persulfate (AP), methanol (MeOH), and dichlorodimethylsilane (CMS) obtained from Sigma-Aldrich (St. Louis, Mo.); 1-ethyl-3-[3-dimethylaminopropyl]-carbodiimide hydrochloride (EDC), N-hydroxysulfosuccinimide (Sulfo-NHS), and Sulfosuccinimidyl-4- (N-maleimidomethyl)-cyclohexane-1-carboxylate (sulfo-SMCC) obtained from Pierce (Rockford, Ill.); and bsp-RGD(15) from American Peptide (Sunnyvale, Calif.).

The IPN coating was polymerized in two parts: first an AAm layer was polymerized directly on quartz discs, and next a poly(ethylene glycol/acrylic acid) (PEG/AAc) layer was polymerized within the AAm network. The IPNs were then modified with an RGD cell-binding peptide isolated from bone sialoprotein to allow for cell attachment. Quartz discs (1" O.D.×¼" thick; Chemglass, Inc) were cleaned with an oxygen plasma (March Plasmod; Concord, Calif.) for 5 min at 1 Torr. The discs were functionalized with an organosilane, MPMS, by immersing in a solution composed of 94% (v/v) MeOH, 5% (v/v) water, 1% (v/v) MPMS, and 1 mM AAm for 5 min, rinsed in MeOH, and baked for 30 min at 110° C. Solutions of 10% AAm and 0.01-0.3% Bis were prepared in water and degassed. Polymerization was initiated with AP and TEMED. AAm solutions were pipetted onto functionalized quartz discs and sandwiched with top coverslips that were been modified with CMS. After polymerization, the samples were immersed in water, and top coverslips were removed carefully. A second layer of PEG/AAc was polymerized on top of and within the AAm layer by previous methods (Bearinger et al., *Journal of Biomaterials Science-Polymer Edition* 9(7):629-652). The AAm-modified quartz discs were allowed to equilibrate in a solution of 0.02 g/mL PEGMA, 0.01 g/mL Bis, 0.3348 g/mL CQ, and AAc in methanol for 5 min. The PEG/AAc layer was polymerized in a light box (Rayonet; Branford, Conn.) for 40 min, and samples were rinsed in methanol and water.

The surfaces were then functionalized with an RGD cell-binding peptide. PEG spacer chains were tethered to the AAc sites in the PEG/AAc layer by exposure to a solution of 0.20 g/mL of PEG(NH$_2$)$_2$, 0.4 mg/mL EDC, and 1.1 mg/mL Sulfo-NHS for one hour. Next, a heterobifunctional crosslinker, sulfo-SMCC (0.5 mg/mL in sodium borate buffer, pH 7.5, 30 min) was used to attach a cell-binding RGD peptide (0.1M solution in sodium borate buffer, pH 6.6, reacted overnight).

Atomic Force Microscopy (AFM) Experiments were performed in order to measure the Young's modulus (E) of the gels. A Bioscope AFM in force-mode and a fluid cell were used in these experiments. A v-shaped silicon nitride tip was modified with a 10 um polystyrene bead in order to reduce strain on the gels during measurements. The E of the gels varied linearly from 0.23±0.09 kPa to 9.86±0.14 kPa depending on the concentration of BIS used in the polymerization of the AAm layer. Data depicting this behavior is presented in FIG. 2, where the square of the correlation coefficient ($R^2$) is 0.9735.

Example 3

IPN Seeded with Growth Factors and Satellite Cells
Cell Culture and Seeding. Four-month-old B6.129S7-Gt (ROSA)26Sor/J mice (The Jackson Laboratory) are killed, and the satellite cells are isolated from hindlimbs, as described in Irintchev et al, *Eur. J. Neurosci.*, 10:366 (1998). Briefly, hindlimb skeletal musculature are surgically excised, finely minced, and disassociated in 0.02% Trypsin (GIBCO) and 2% Collagenase type 4 (Worthington) for 60 min at 37° C./5% CO$_2$ while agitating on an orbital shaker. Disassociated muscle can be strained in a 70-µm sieve, centrifuged at 1,600 rpm (Eppendorf 5810R) for 5 min, and resuspended in 10-mL-high glucose DMEM, supplemented with pyruvate (GIBCO). Media is further supplemented with 10% FBS and 1% penicillin/streptomycin (GIBCO). Resuspended cells are plated on an IPN of the invention, such as described in Example 1, and HGF (50 ng/mL) and FGF2 (50 ng/mL) are added to the medium. After 7 days, cultures are passaged, and purified satellite cell suspensions are obtained via Percoll fractionation, as described in McKinney-Freeman et al, *Proc. Natl. Acad. Sci. USA,* 99: 13411346, (2002). Purified cultures a incubated for 7 days at 37° C. until 80% confluent and then collected via trypsinization and seeded at 10$^7$ cells/ml onto an modified open-pore polymer scaffolds.

Example 4

In this study, rat adult neural stem cells (NSCs) were grown on an IPN consisting of two crosslinked polymer networks, one of poly(acrylamide) and the other of poly(ethylene-co-acrylic acid) [(p(AAm-co-EG/AAc)]. In addition, (bsp-RGD 15) was grafted via the acrylic acid sites on the p(AAm-co-EG/AAc) IPN to provide cell binding domains. An important feature of this IPN is that ligand density is easily tunable by varying the concentration of [bsp-RGD(15)] peptide during grafting. Furthermore, ligand density is completely defined for the culturing surface, as the non-fouling nature (i.e., low protein adsorption) to media components of the remainder of the IPN [i.e., p(AAm-co-EG) IPN] has been extensively characterized (Harbers, et al., *Langmuir,* 21(18):8374-8384. (2005); (Bearinger et al., *Journal of Biomaterials Science-Polymer Edition,* 9(7):629-652 (1998)). Examples 1 and 2 describe the synthesis and characterization of bsp-RGD(15)-modified IPNs. After synthesis, IPNs were sterilized by the use of ethanol as previously described (Huebsch et al., *J Biomed Mater Res B Appl Biomater,* 74(1):4407 (2005)).

As a positive control in this study, cell culture surfaces were coated with an ECM protein, laminin, using traditional stem cells culturing protocols. The positive control surfaces were coated with poly-ornithine and saturated with mouse laminin I (Invitrogen, from the Engelbreth-Holm-Swarm (EHS) sarcoma) as described in the literature (Lai, K., et al., *Nat Neurosci,* 6(1):21-7 (2003)). Briefly, poly-ornithine (10 µg.mL$^{-1}$ in water) was added to cover a polystyrene culture well (~50 µL) and incubated overnight at room temperature. Wells were then rinsed twice with sterile water, and laminin (~5 µg.mL$^{-1}$ in phosphate buffered saline) was added to cover the well. After incubation overnight at 37° C., wells were frozen at −20° C. until use.

As a negative control in this study, IPNs grafted with bsp-RGE(15) were used to test the specificity of cell response to the RGD motif in bsp-RGD(15)-modified IPNs.

4.1 NSC Isolation and Culturing Conditions

Neural stem cells were isolated from the hippocampi of adult female Fischer 344 rats as previously described (Lai, K., et al., *Nat Neurosci,* 6(1):21-7 (2003)). Cells at (200-10,000 cells/well) were seeded onto peptide-modified IPNs and laminin-modified culture wells and incubated (37° C., 5% $CO_2$) in serum-free media consisting of DMEM/Hams F-12 medium with N-2 supplement. These media conditions were supplemented with various soluble factors to modulate cell behavior: 20 ng.ml$^{-1}$ basic fibroblast growth factor (bFGF) for cell proliferation or 1 µM retinoic acid with 5 µM forskolin for neuronal differentiation. Wells were rinsed every 48 hrs with fresh media.

4.2 NSC Proliferation on bsp-RGD(15)-Modified IPNs

NSCs isolated from the adult hippocampus were seeded onto bsp-RGD(15)-modified IPNs at various cell densities over four orders of magnitude. Under media conditions that include a factor critical for self-renewal, bFGF (i.e., proliferating media conditions), cell adhesion and morphology on the RGD surfaces were similar to that on laminin (FIG. 2 a-b). By contrast, on surfaces with either low or no bsp-RGD(15), cells did not adhere effectively (FIG. 2 c-d) and resembled NSC growth in suspension as neurospheres Sen et al., *Biotechnol Prog.* 18(2):337-45 (2002)). Such spheres provide less precise control over the cellular microenvironment, due in part to spatial gradients in signaling and nutrients and internal necrosis. The bsp-RGE(15), which differs from the bsp-RGD(15) peptide by only a methylene group, did not support attachment and thus highlighted the specificity of the NSC engagement with the peptide-modified IPN.

For quantitative assays of proliferation, the NSCs were seeded at 1000 cells per well on various surfaces and grown for 3-6 days, and cell number was determined using a fluorescent dye that binds to nucleic acids, CyQUANT (Molecular Probes, Eugene, Oreg.). Briefly, cells grown on a particular surface for a fixed duration were washed once with phosphate buffer saline and lysed in the manufacturer's buffer with dye. Next, the fluorescent intensity of resulting solution was measured. Importantly, the bsp-RGD(15)-modified IPN also supported NSC proliferation in a ligand dose-dependent fashion, and IPNs with the highest bsp-RGD(15) density supported faster cell proliferation than standard laminin-coated surfaces (FIG. 2 e). Any increase in cell number on the negative control bsp-RGE(15)-modified IPNs reflected growth of weakly adherent neurospheres (FIG. 2 d-e). About 10 pmol.cm$^{-2}$ bsp-RGD(15) was needed to support proliferation of NSCs, corresponding to ~$10^6$ ligands per cell for the 10 µm diameter cells.

4.3 NSC Phenotype and Differentiation on bsp-RGD(15)-Modified IPNs

In addition to precise control of cell proliferation, the bsp-RGD(15)-modified IPNs supported multipotent NSCs in several states of differentiation. To assay phenotype, two methods were used: quantitative real time PCR (qRT-PCR) and immunofluorescent staining. These methods have been frequently used to assay phenotype of cells (Abranches, et al., *Biotechnol Appl Biochem,* 44(Pt 1):18 (2006)). In these experiments, NSCs seeded onto bsp-RGD(15)-modified IPNs at 10,000 cells/well and the media conditions either promoted self-renewal, 1.2 nM bFGF (i.e., proliferating media conditions) or differentiation, 1 µM retinoic acid with 5 µM forskolin for neuronal differentiation. For immunofluorescent staining, cells on days 1-14 were fixed with 4% paraformaldehyde and stained with primary antibodies of mouse anti-nestin (1:1000 dilution), mouse anti-microtubule associated protein 2ab (Map2ab) (1:250), and guinea pig anti-glial fibrillary acidic protein (GFAP) (1:1000). cytoskeletal markers that are characteristic of a particular differentation state. Nestin is a marker of an immature neural cell, Map2ab marker of differentation to a neuron, and GFAP is a marker of differentiation into a glial phase or an astrocyte. Detection of primary antibodies was performed with Alexa fluorochrome-conjugated secondary antibodies at a dilution of 1:250. Nuclei were stained with the nuclear marker Sybergreen and 4'-6-Diamidino-2-phenylindole (DAPI) (Molecular Probes, Eugene, Oreg.). Images were collected on an Olympus IX-50 microscope and Zeiss META 510 confocal microscope. Quantitative real time PCR was used as a complementary technique to accurately quantify specific cDNA concentrations in various cDNA samples from cells grown on IPNs and laminin (using a Bio-Rad Laboratories icycler). GFAP expression levels were quantified as a marker for astrocytic differentiation of the progenitor cells. β-Tubulin-III was used as a marker for neurons. Nestin was used as a marker for NSCs. Ribosomal 18S was employed to normalize the various samples for differences in the starting amounts of cDNA used in each sample. The utilized primers and TAQMAN probes are listed as follows in the following format (marker, left primer, right primer, hybridization TAQMAN oligo): (GFAP, GACCTGCGACCTTGAGTCCT; SEQ ID NO: 8, TCTCCTCCTT-GAGGCTTTGG; SEQ ID NO: 9, TCCTTGGAGAGGCAAATGCGC; SEQ ID NO: 10), (β-Tubulin-III, GCATGGATGAGAT-GGAGTTCACC; SEQ ID NO: 11, CGACTCCTCGTCGTCATCTTCATAC; SEQ ID NO: 12, TGAACGACCTGGTGTCTGAG; SEQ ID NO: 13) (Nestin, GAGCTCTCTGGGCAAGTGGA; SEQ ID NO: 14, CTCCCACCGCTGTTGATTTC; SEQ ID NO: 15, AGGACAG-TCAGCAGTGCCTGCA; SEQ ID NO: 16), and (18S, GTAACCCGTTGAACCCCATTC; SEQ ID NO: 17, CCATCCAATC-GGTAGTAGCGA; SEQ ID NO: 18, AAGTGCGGGTCATAAGCTTGCG; SEQ ID NO: 19). Standards for performing qRT-PCR were pPCR4-TOPO plasmids (Invitrogen) containing the containing the amplicon of interest as an insert. The plasmids were linearized by restriction digest and quantified by absorbance, and tenfold serial dilutions from 1 ng/µL to $10^{-9}$ ng/µL were prepared to generate a standard curve. All samples were conducted in duplicate.

Figure 3A:
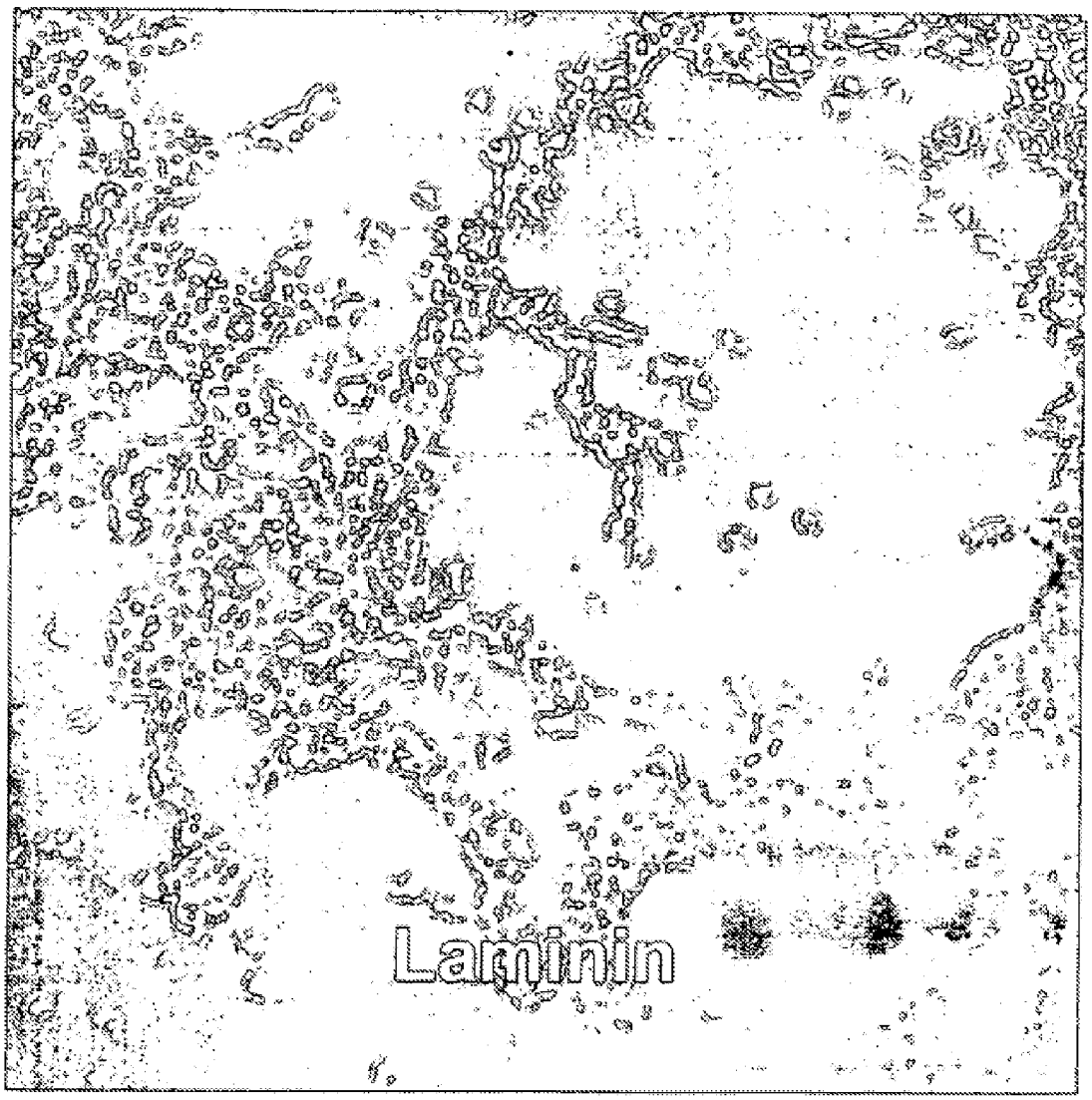
FIG. 3. Synthetic IPNs with RGD peptides support attachment, spreading, and proliferation of neural stem cells in a dose dependent manner. a)-d) Bright field images of neural stem cells grown on top of IPNs or laminin-I in proliferating media conditions (1.2 nM basic fibroblast growth factor); e) Growth curves for proliferation of neural stem cells as assayed by a total nucleic acid stain. Data represent mean±standard deviation of 3-5 samples. Surfaces not in the same group (*, §, †, or ‡) were statistically different from one another ($p<0.05$; ANOVA between groups with Tukey-Kramer Honestly Significant Difference post-hoc test).
Figure 3B:
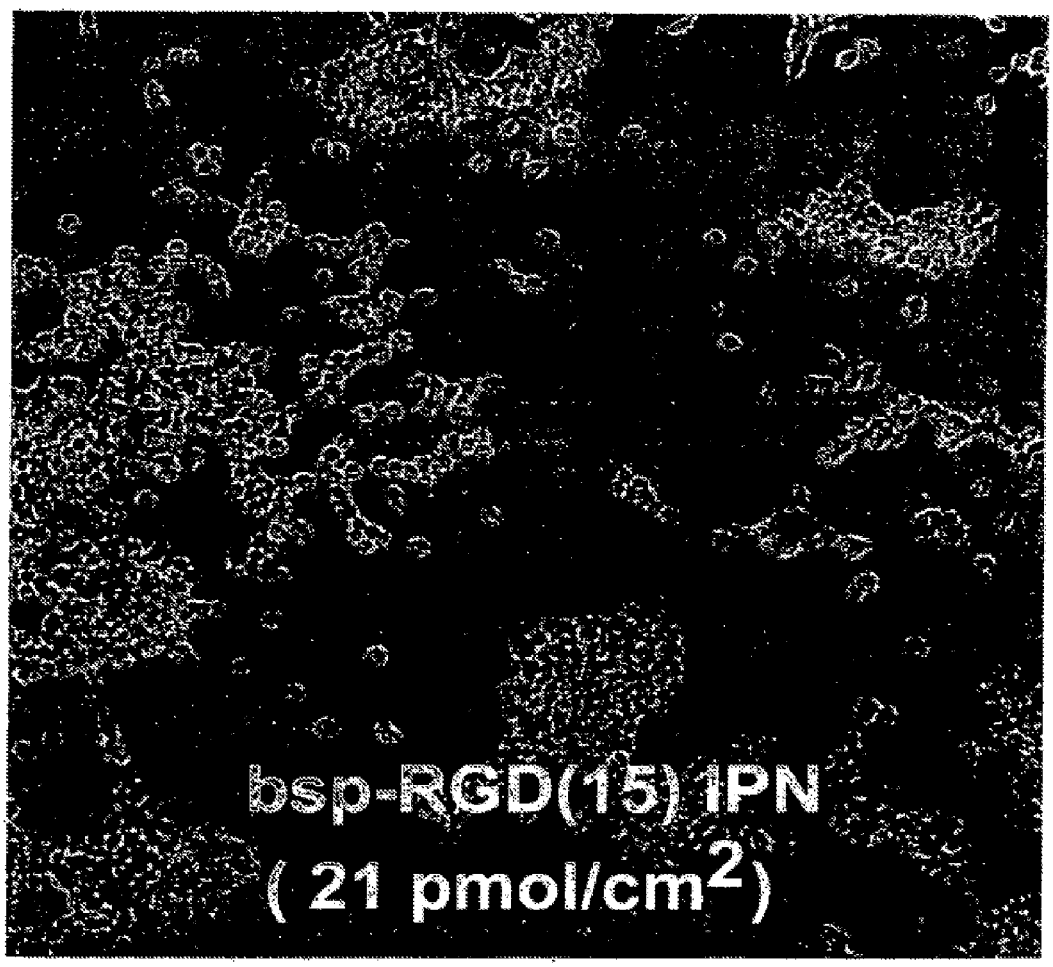
Figure 3C:
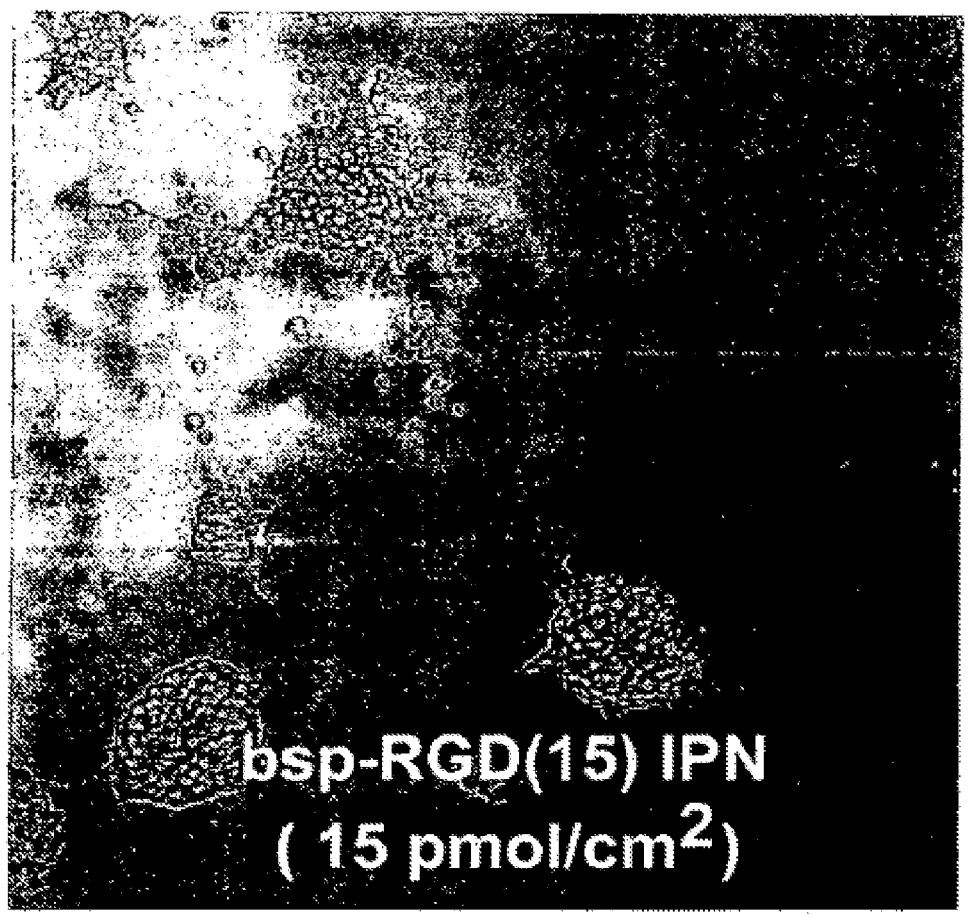
Figure 3D:
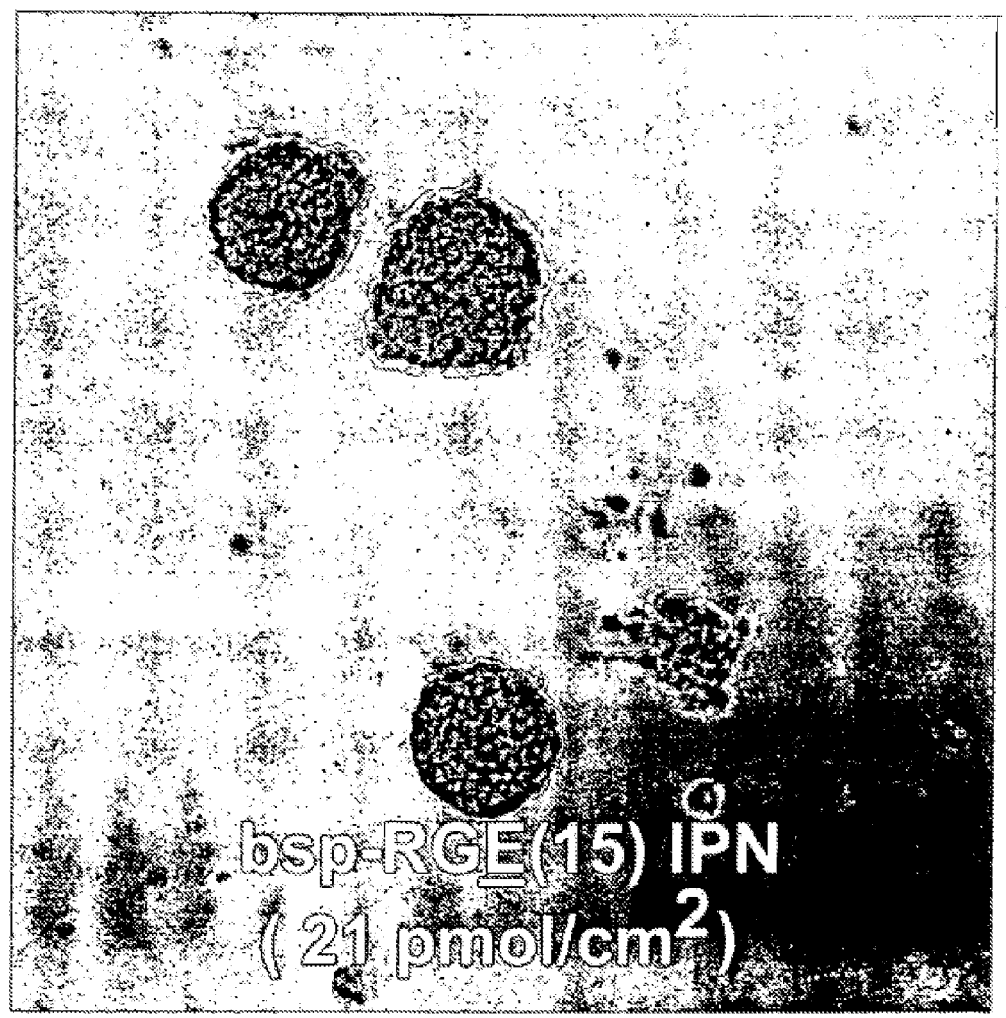
Figure 3E:
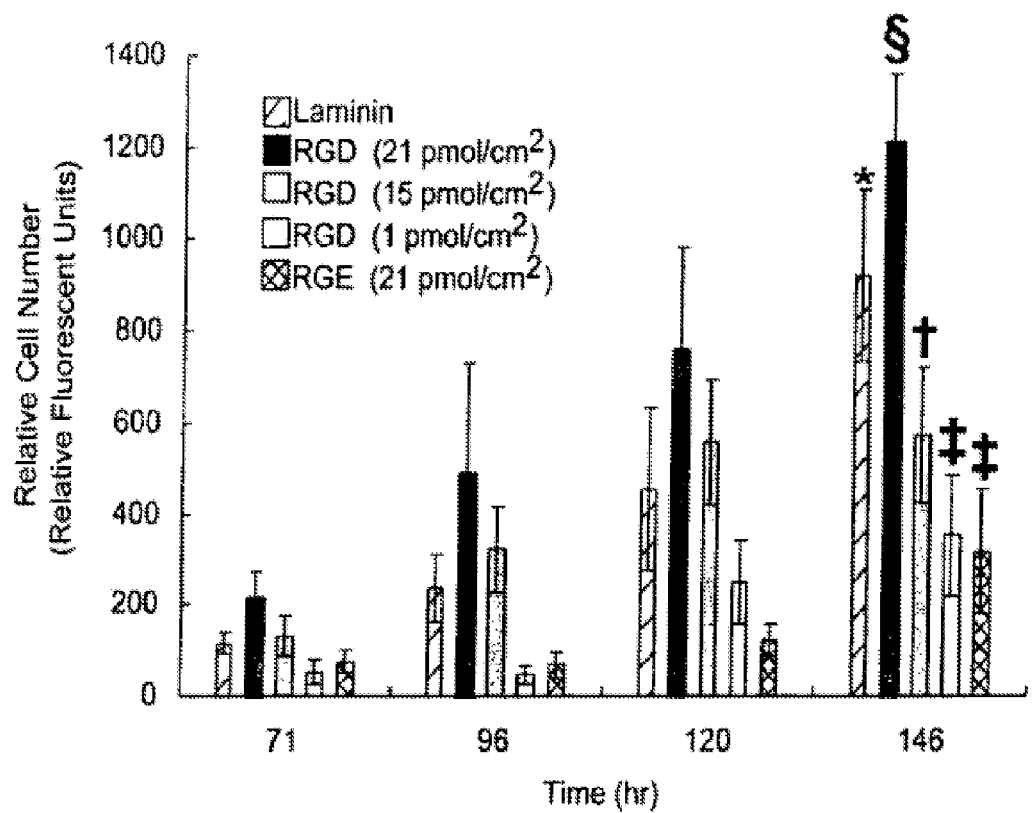
Figure 4A:
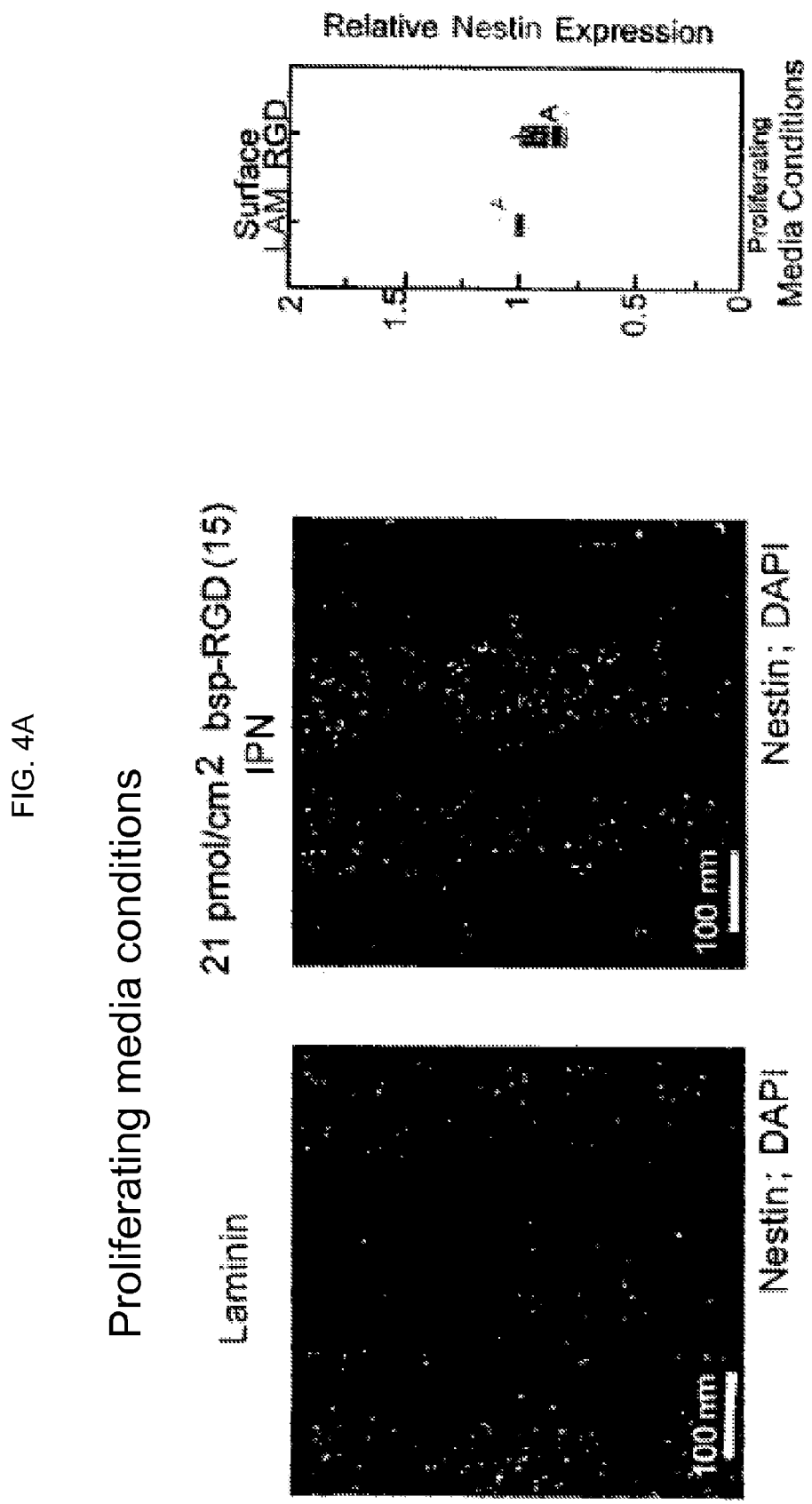
FIG. 4 Cell phenotype of immature and differentiated cells on synthetic RGD-modified IPNs. a) Immunofluorescent staining for the immature neuronal stem cell marker nestin (green) in cells proliferating on laminin or 21 pmol.cm$^{-2}$ bsp-RGD(15) modified IPNs (media conditions: 1.2 nM basic fibroblast growth factor). In all stained images, cell nuclei were stained with Sybergreen or DAPI (blue); b) Bright field images of neural stem cells on laminin or 21 pmol.cm$^{-2}$ RGD-modified hydrogels during neuronal differentiation (media conditions: 1 μM retinoic acid with 5 μM forskolin for six days); Cellular staining for c) the early neuronal marker microtubule associated protein 2ab (Map2ab, green) and d) the mature astrocyte marker glial fibrillary acidic protein (GFAP, red) on laminin or 21 pmol.cm$^{-2}$ RGD modified hydrogels during differentiation. Right-hand panels compare expression levels as measured by quantitative RT-PCR during proliferation and differentiation for lineage markers, Nestin, β-tubulin III, and GFAP. The box plots summarize the distribution of points, where the thick line signifies the median and the ends of the box are the 25th and 75th quartiles. Within each plot, levels not connected by same letter are significantly different ($p<0.05$; ANOVA between groups with Tukey-Kramer Honestly Significant Difference post-hoc test).
Figure 4B:
Figure 4B:

Similar protein levels of nestin, a neurofilament characteristic of immature neural cells (Lendahl et al., *Cell,* 60(4): 585-95 (1990)), were observed on bsp-RGD(15)-modified IPNs and laminin surfaces for all time points analyzed up to 14 days in bFGF (i.e. proliferating conditions) (FIG. 3a). Subsequently, cells were subjected to differentiation conditions (i.e. retinoic acid and forskolin) (Palmer et al., T. D., *Mol Cell Neurosci,* 6(5):474-86 (1995)). Cell morphology as well as immunostaining of lineage specific markers were similar on laminin versus bsp-RGD(15)-modified IPN surfaces (FIG. 3b-d, left). Furthermore, quantitative RT-PCR for lineage specific markers indicated that the laminin and bsp-RGD (15)-modified IPN surfaces supported differentiation into neural lineages to the same extent (FIG. 3b-d, right). We next examined whether cell differentiation depended on RGD density, as found previously for cell proliferation (FIG. 2). The ability of the surfaces to support differentiation decreased with reducing RGD density (FIG. 4a-b). Between 5.3 and 11 pmol.cm$^{-2}$ bsp-RGD(15) was needed to support both proliferation and differentiation (see below) of NSCs.

This examples indicate that a synthetic IPN presenting a simple RGD-containing motif functionally replaced the ability of laminin I to support cell attachment, proliferation, and differentiation, a significant result considering that complex ECM molecules such as laminin are extremely large (850 kDa) and contain a number of cell-binding motifs (Tashiro, et al.,. *J Cell Physiol*, 146(3):451-9 (1991); (Bellamkonda et al., *J Neurosci Res*, 41(4): 501-9 (1995), (Powell et al., *Int J Biochem Cell Biol*, 29(3): 401-14 (1997)).

Example 5

In this study, we took advantage of the fact that the highly modular synthetic IPN network could be conjugated with diverse combinations of biochemical signals at various ratios. Rat adult neural stem cells were grown on an IPN with a mixture of two different peptides. The IPN consisted of two crosslinked polymer networks, one of pAAm and the other of PEG/AAc. In addition, a mixture of peptides were grafted via the acrylic acid sites on the p(AAm-co-EG/AAc) IPN to engage and potentially influence differentiation of the NSCs. The mixture consisted of any two of the following peptides: [bsp-RGD(15)], 19 amino-acid laminin peptide putatively involved in promoting neurite outgrowth of mature neurons and differentiation of fetal neuronal progenitors (Tashiro, et al., *J Biol Chem*, 264(27): 16174-82 (1989); (Bellamkonda et al., *J Neurosci Res*, 41(4): 501-9 (1995); (Silva, et al., *Science*, 303(5662): 1352-5 (2004)) CSRARKQAASIKVAVSADR [1am-IKVAV(19)]; SEQ ID NO: 7, and bsp-RGE(15). Example 1 describes the synthesis and characterization of the peptide-modified IPN. NSC isolation, culturing conditions, and differentiation assays were performed as in Example 4.

Figure 4C:
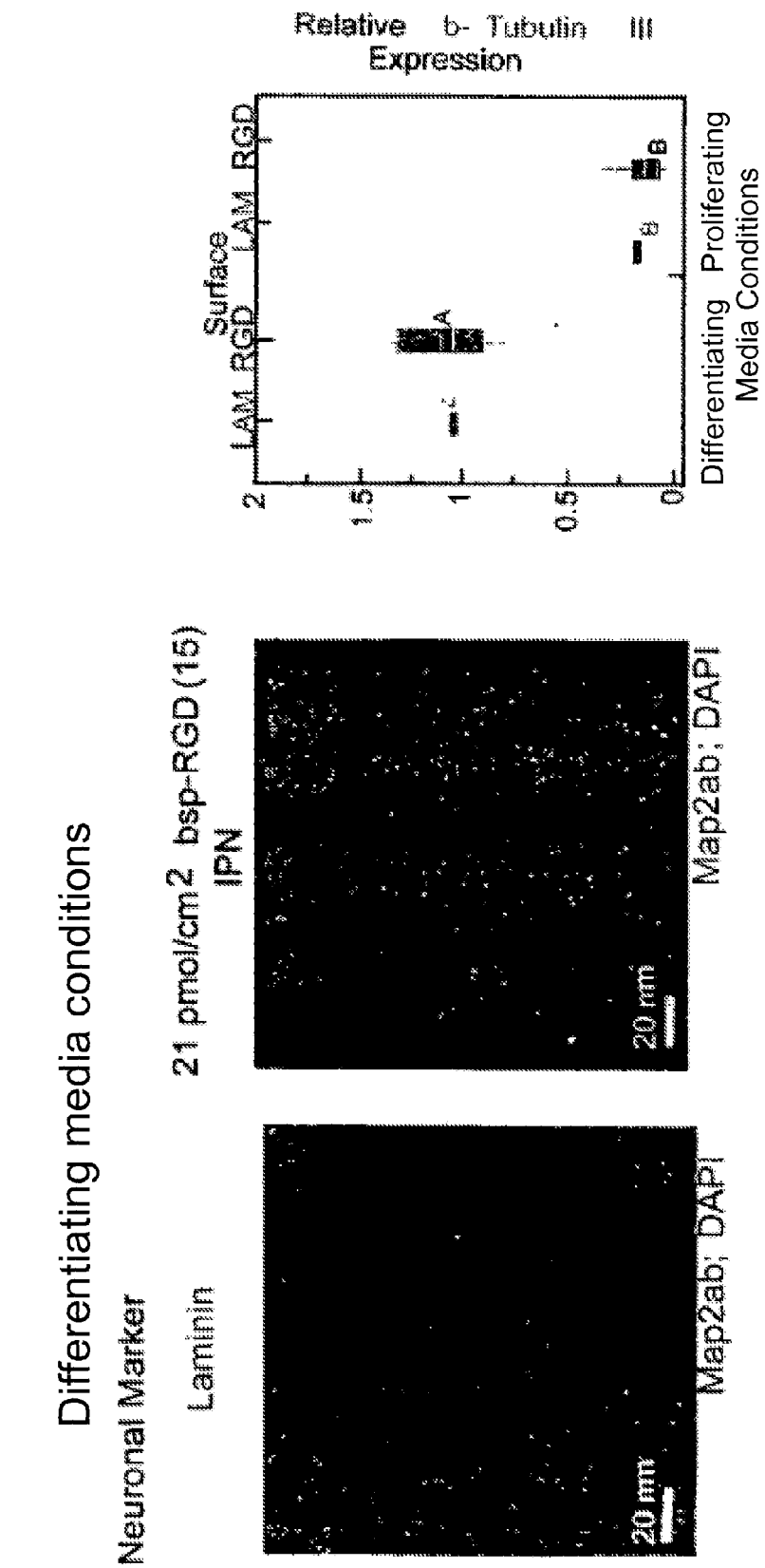
Figure 4D:
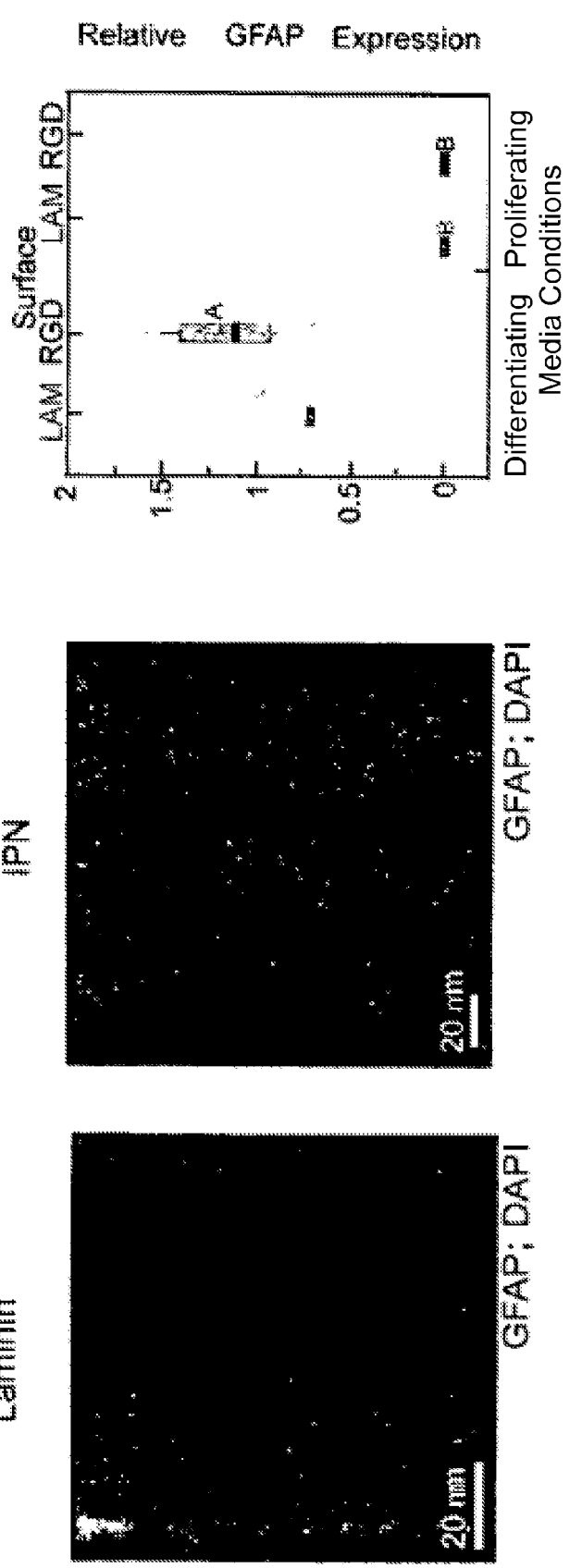
Figure 5A:
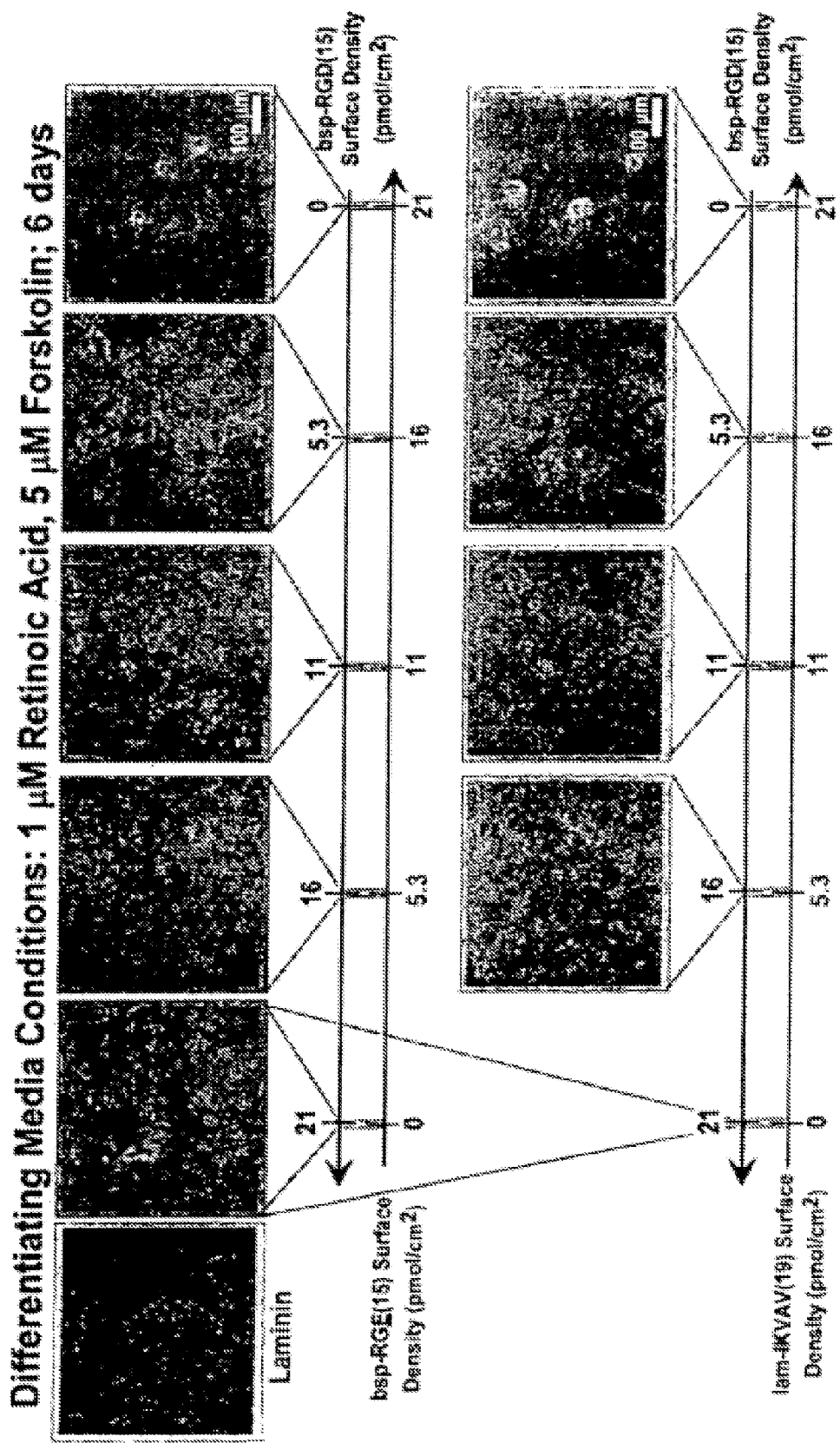
FIG. 5 In mixed peptide IPNs, bsp-RGD(15) peptide surface density controls phenotype. a) Bright field images of NSCs after six days in culture on IPNs with mixed peptide conjugation in differentiating (1 μM retinoic acid, 5 μM forskolin) media conditions. Surface density of peptide mixtures correspond to abscissa values directly below for bsp-RGD (15) plus 1am-IKVAV(19) or bsp-RGE(15); b) Expression of early neuronal marker, β-Tubulin III, and astrocyte marker, glial fibrillary acidic protein (GFAP), of NSCs grown in differentiation media conditions as assayed by quantitative RT-PCR after six days. The box plots summarize the distribution of points, where the thick line signifies the median and the ends of the box are the 25th and 75th quartiles. Within each plot, levels not connected by same letter are significantly different ($p<0.05$; ANOVA between groups with Tukey-Kramer Honestly Significant Difference post-hoc test); c) Bright field images of NSCs after six days in culture on IPNs with 21 pmol.cm$^{-2}$ bsp-RGD(15) or 1am-IKVAV(19) peptide conjugation in proliferating (1.2 nM bFGF) media conditions.
Figure 5B:
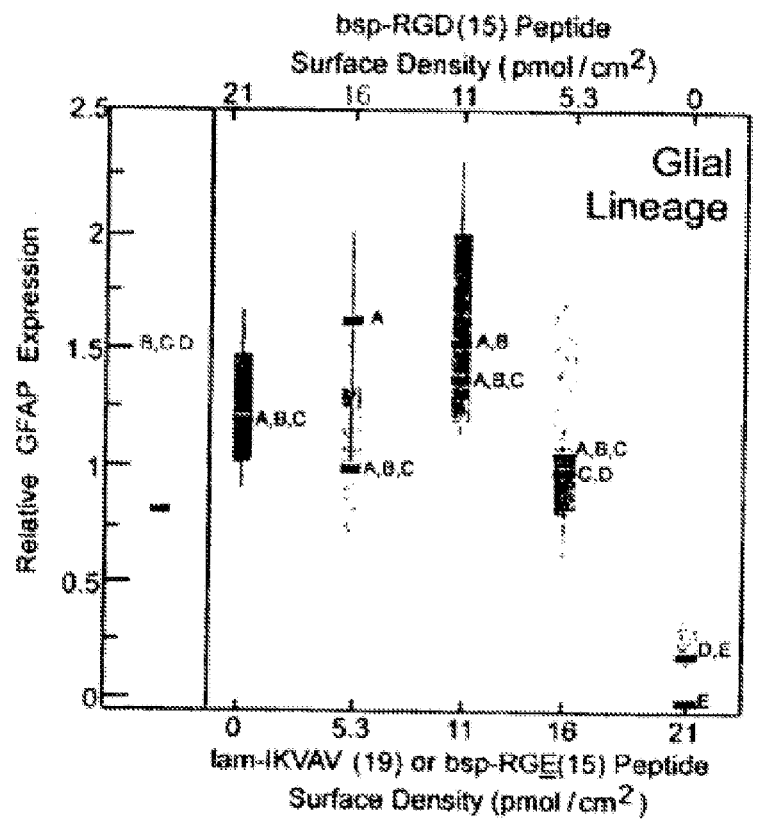
Figure 5B:
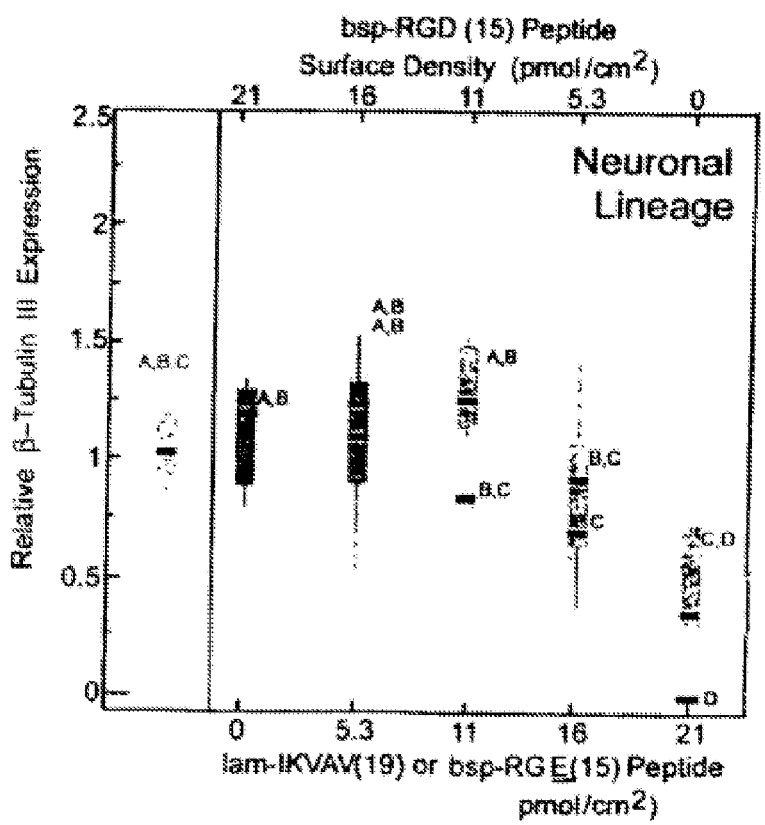
Figure 5C:
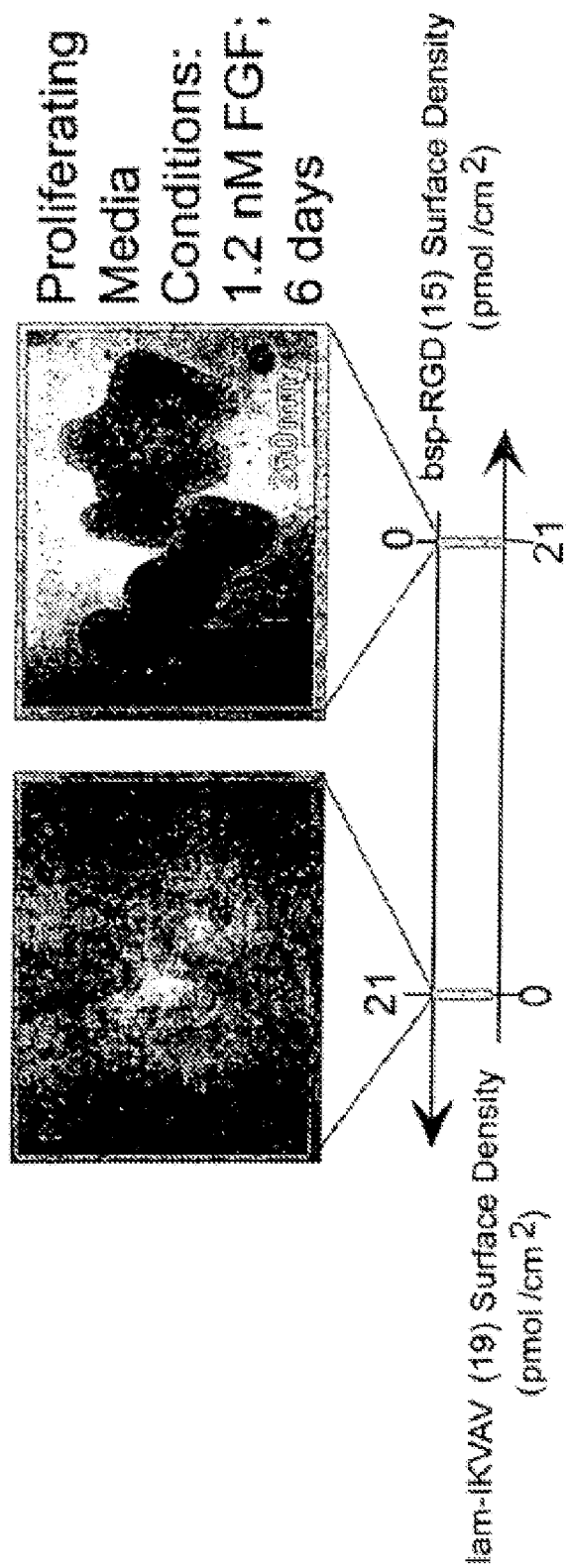
Figure 6:
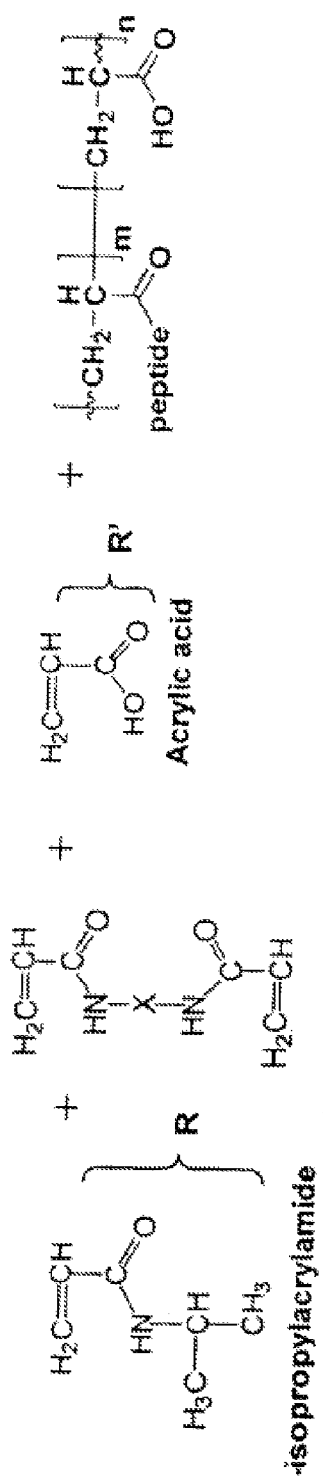
FIG. 6 is a scheme for preparing an exemplary modified linear polymer useful in a sIPN of the invention in which p(AAc) is the linear polymer chain and a synthetic peptide serves as the biomolecule. The —COO$^-$ groups in the linear p(AAc) chains are reacted with one end of a heterobifunctional cross-linker. The other end of the cross-linker is then used to graft the biomolecule to the p(AAc) chains. In the figure, the solid lines represent the cross-linked polymer, the dashed lines represent the linear polymer, and the ovals represent the ligand.
Figure 6:
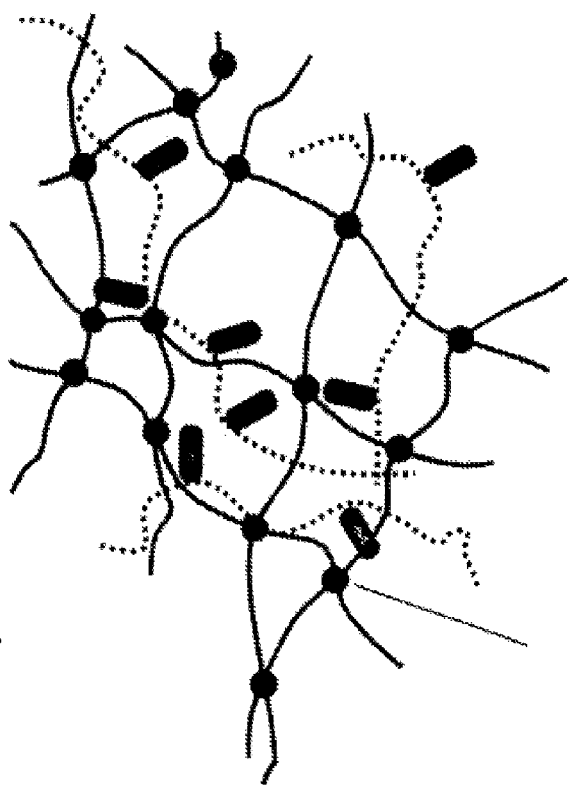
Figure 6:
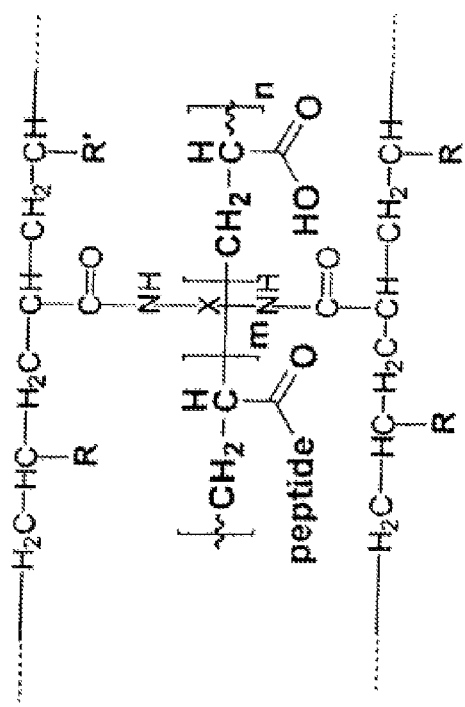
Figure 7:
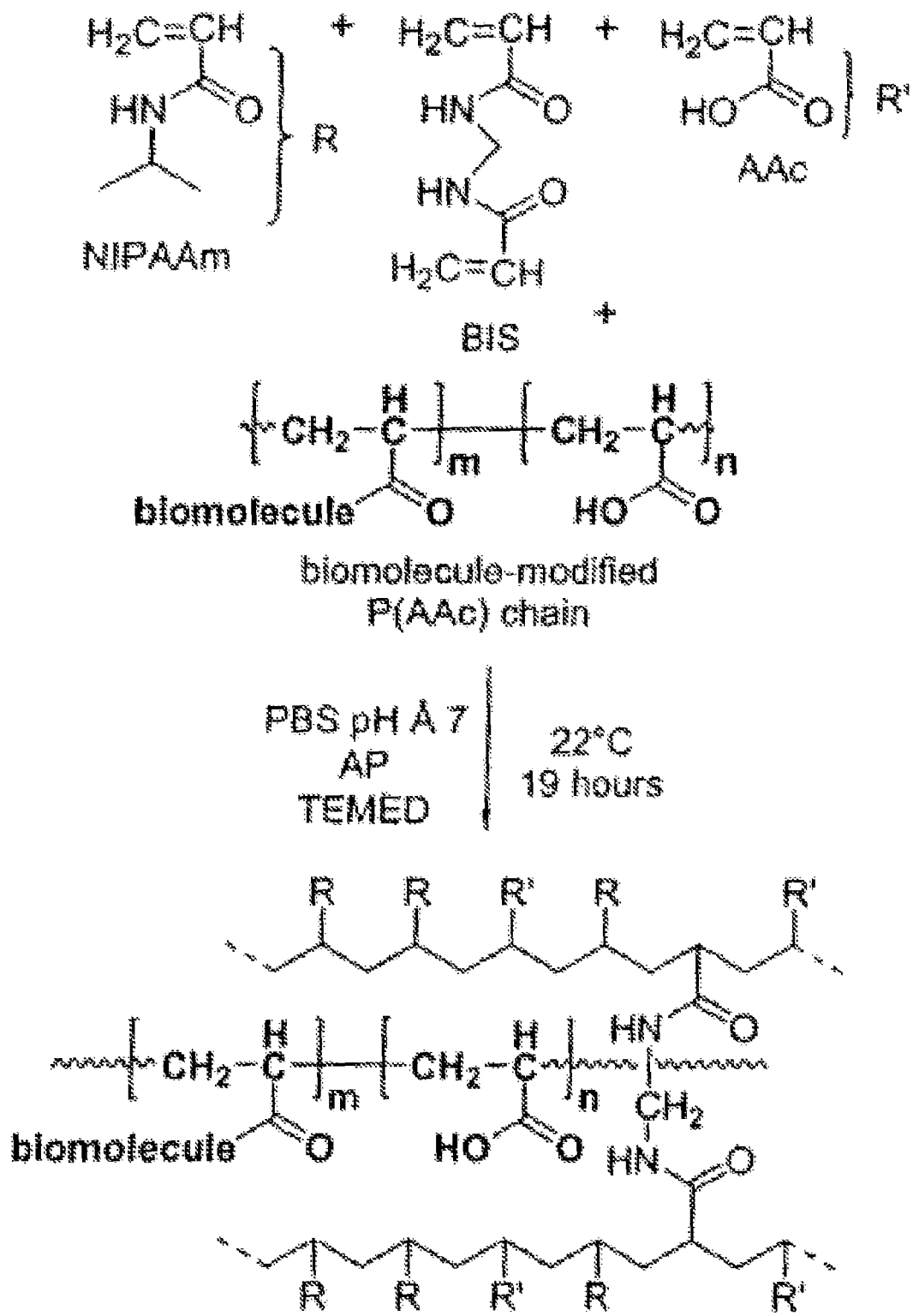
FIG. 7 is a synthetic scheme for preparing a sIPN of the invention, which incorporates a biomolecule modified linear p(AAc) polymer. The modified p(AAc) chains are added to the polymerization formulation, and the p(NIPAAm-co-AAc) cross-linked network forms in the presence of the chains. Thus, the chains are physically entangled within the cross-linked network.

We observed that 1am-IKVAV(19) did not enhance either cell proliferation or differentiation (FIG. 4b-c). On pure 1am-IKVAV(19)-modified IPNs, NSCs did not adhere under differentiating or proliferating media conditions, similar to behavior on the negative control RGE surface (FIG. 1d, FIG. 4a-c). Furthermore, cell differentiation into either a neuronal or astrocytic lineage progressively decreased as the IKVAV/RGD ratio increased (FIG. 4a-b). These results further confirm that the RGD peptide-modified IPN, without introducing any cooperative effects from mechanisms involving 1am-IKVAV(19), was able to functionally substitute for laminin in early differentiation stages of adult NSCs.

Example 6

Method for Stem Cell Recovery without Using Enzymes for IPNs

Human ESCs can be grown and recovered on thermoreversible IPNs grafted to glass, quartz, other metal oxides, or polystyrene. These thermoreversible IPNs can be made with variable modulus and ligand surface densities to control stem cell self-renewal and fate. Exploiting the thermoreversible nature of the IPN, the undifferentiated stems can be removed from the substrate by simply adjusting the thermal environment (i.e., reducing the ambient temperature below the LCST of the IPN). Culturing stem cells under these conditions alleviates the aforementioned contamination problems associated with feeder layers and use of animal derived products such as enzymes. Synthesis of the thermoreversible IPNs grafted to quartz is given as an example of this method. The materials used in this synthesis are: methacryloxypropyltrimethoxysilane (MPMS) obtained from Gelest (Morrisville, Pa.); acetic acid (AA), NIPAAm, methoxy poly(ethylene glycol) (MW=200) methacrylate (mPEG200MA) (MW=300 g/mol), poly(ethylene glycol) (MW=200) diacrylate (PEG200DA) (MW=302 g/mol), N,N,N',N'-tetramethylethylenediamine (TEMED), poly(ethylene glycol) monomethyl ether monomethacrylate, MW 1000) (pEG$_{1000}$MA), camphorquinone (CQ), acrylic acid (AAc), and 3400 MW diamino-PEG [3400-PEG(NH$_2$)$_2$] obtained from Polysciences (Warrington, Pa.); ammonium persulfate (AP), methanol (MeOH), and dichlorodimethylsilane (CMS) obtained from Sigma-Aldrich (St. Louis, Mo.); 1-ethyl-3-[3-dimethylaminopropyl]-carbodiimide hydrochloride (EDC), N-hydroxysulfosuccinimide (Sulfo-NHS), and Sulfosuccinimidyl-4- (N-maleimidomethyl)-cyclohexane-1-carboxylate (sulfo-SMCC) obtained from Pierce (Rockford, Ill.); and bsp-RGD(15).

The thermoreversible IPN coatings are polymerized sequentially. First an NIPAAm/mPEG200MA layer is polymerized directly on quartz discs, subsequently a poly(ethylene glycol/acrylic acid) (pEG/AAc) layer is polymerized within the NIPAAm/mPEG200MA network, but not crosslinked to it. The IPNs are then modified with bsp-RGD (15) to promote for stem cell attachment. Quartz discs (1" O.D.×¼" thick; Chemglass, Inc) are cleaned with an oxygen plasma (March Plasmod; Concord, Calif.) for 5 min at 1 Torr. The discs are functionalized with an organosilane, MPMS, by immersing in a solution composed of 94% (v/v) MeOH, 5% (v/v) water, 1% (v/v) MPMS, and 1 mM AA solution for 5 minutes and baking for 30 min at 110° C. Solutions of 10% NIPAAm/m PEG200MA/pEG$_{200}$DA [molar ration 96:3:1] are prepared in water and degassed. Polymerization is initiated with AP and TEMED. NIPAAm/mPEG200MA/pEG$_{200}$DA solutions are pipetted onto functionalized quartz discs and sandwiched with top coverslips that are modified with CMS. After polymerization, the samples are immersed in UPW, and top coverslips removed. The second layer of PEG/AAc is polymerized on top of and within the NIPAAm/mPEG200MA layer by previous methods (Harbers, et al., *Langmuir*, 21(18):8374-8384. (2005)) NIPAAm/mPEG200MA-modified quartz discs are allowed to equilibrate in a solution of 0.02 g/mL PEG1000MA, 0.01 g/mL Bis, 0.3348 g/mL CQ, and AAc in methanol for 5 min. The pEG/AAc layer is polymerized in a light box (Rayonet; Branford, Conn.) for 40 min, and samples are rinsed in methanol and water. The surfaces were then functionalized with a ligand, for example bsp-RGD(15). A PEG spacer is tethered to the AAc sites in the pEG/AAc layer by exposure to a solution of 0.20 g/mL of pEG(NH$_2$)$_2$, 0.4 mg/mL EDC, and 1.1 mg/mL Sulfo-NHS for one hour. Next, a heterobifunctional crosslinker, sulfo-SMCC (0.5 mg/mL in sodium borate buffer, pH 7.5, 30 min) is used to attach the ligand (0.1M solution in sodium borate buffer, pH 6.6, reacted overnight). Atomic Force Microscopy Experiments are performed in order to measure the Young's modulus (E) of the thermoreversible IPNs. A Bioscope AFM in force-mode and a fluid cell is used in these experiments. A v-shaped silicon nitride tip is modified with a 10 um polystyrene bead in order to reduce strain on the gels during measurements. The E of the gels can be made to vary between 200 Pa to 100 kPa by either adjusting the concentration of mPEG200MA, mPEG200DA, or both. On these thermoreversible IPNs hESCs are cultured using complete culture medium (KSR) that have been condiditioned by mouse embryonic feeders (MEFs). KSR consists of: Knockout-DMEM (Gibco), 20% Knockout Serum Replacement (Gibco), 2 mM Glutamine (Gibco), 0.1 mM non-essential amino acids (NEAA) (Gibco), 0.1 mM β-Mercaptoethanol (Sigma), and 4 ng/mL basic fibroblast growth factor (FGF)-2 (R&D Systems). KSR is added to irradiated MEFs for 24 hours and removed such that soluble factors from the MEFs are included. Since the thermoreversible IPNs undergoes a LCST transition, whereby the change in the surface's physical properties can release the hESCs from the hydrogel surface, reducing the temperature below the LCST to release the hESCs.

Example 7

This example details the formation of a sIPN to support stem cell self-renewal or differentiation. The cell-binding adhesion peptide bsp-RGD(15) and the heparin-binding adhesion peptide acetyl-CGGFHRRIKA-NH$_2$ (SEQ ID NO: 4)(-FHRRIKA-; SEQ ID NO: 5), of bone sialoprotein (BSP), were incorporated into the p(NIPAAm-co-AAc) sIPN.

The materials used to synthesize the sIPN include the following: NIPAAm, AAc, N,N'-methylenebisacrylamide (BIS), ammonium peroxydisulfate (AP), N,N,N',N'-tetramethylethylenediamine (TEMED), and linear p(AAc) chains (450,000 g/mol, acid form), which were obtained from Polysciences, Inc. (Warrington, Pa.), and Dulbecco's Phosphate-Buffered Saline (PBS; 1.51 mM KH$_2$PO$_4$, 155 mM NaCl, and 2.7 mM Na$_2$HPO$_4$; without CaCl$_2$, without MgCl$_2$; pH=7.2±0.1), which was obtained from GIBCO BRL (Grand Island, N.Y.).

The synthesis of the polymeric networks is separated into two parts: first the linear polymer chains are functionalized with a ligand of interest, and purified; subsequently, the sIPN is synthesized with the bio-functionalized linear chains.

7.1 Synthesis of the Bio-Functionalized Linear Chain

The hydrazide end of N-[ε-Maleimidocaproic acid]hydrazide (EMCH)(0.02 g/mL) was first reacted with the —COO$^-$ groups in the p(AAc) chains (1 mg/mL) using 1-ethyl-3-(3-dimethylaminopropyl) carbodiimide (ED C; Pierce, 0.4 mg/mL) and N-hydroxysulfosuccinimide (Sulfo-NHS, Pierce, 1.1 mg/mL) in 2-(N-morpholino) ethanesulfonic acid, 0.9% NaCl, conjugation buffer (MES, Pierce, 0.1M, pH 6.5) for 1 hour at 22° C. The unreacted components were removed via dialysis, the product was lyophilized, and then the maleimide end of EMCH was reacted with the thiol groups of the ligand in 0.1M sodium phosphate buffer (pH 6.6) for 4 hours at 22° C. Again the product was lyophilized, and the functionalized p(AAc) chains were used to synthesize the semi-IPNs, as detailed below. As a specific example, bsp-RGD(15) is grafted to the pAAc chains and is called pAAc-graft-bsp-RGD(15).

7.2 Preparation of the sIPN

The pAAc-graft-bsp-RGD(15) chains (0.001 g to 0.013 g) were added to 2.4395 g (22 mmol) of NIPAAm, 0.005 g (0.0325 mmol) of BIS, 0.0605 g (0.84 mmol) of AAc, and 50 mL of PBS, and the mixture was bubbled with dry nitrogen gas in a two-neck flask for 15 minutes to remove dissolved oxygen. Following the nitrogen gas purge, 0.020 g (0.0876 mmol) of AP and 200 μL (1.3 mmol) of TEMED were added as the initiator and accelerator, respectively. The mixture was stirred vigorously for 15 s and allowed to polymerize at 22° C. for 19 h under regular fluorescent lighting in a 250 mL glass beaker covered with a glass plate. Following the polymerization, the p (NIPAAm-co-AAc)-based semi-IPN was washed three times, 15-20 minutes each, in excess water to remove unreacted compounds.

Example 8 sIPN of p(NIPAAm-co-EG200) Cross-Linked by PEG200DA and Interpenetrated by Peptide-Functionalized Hyaluronic Acid The materials used to synthesize the sIPN include N-isopropyl acrylamide (NIPAAm), methoxy poly(ethylene glycol) (MW=200) methacrylate (mPEG200MA) (MW=300 g/mol), poly(ethylene glycol) (MW=200) diacrylate (PEG200DA) (MW=302 g/mol), ammonium peroxydisulfate (AP), and N,N,N',N'-tetramethylethylenediamine (TEMED) obtained from Polysciences, Inc. (Warrington, Pa.), as well as incomplete Dulbecco's Phosphate-Buffered Saline (iPBS; 1.51 mM KH$_2$PO$_4$, 155 mM NaCl, and 2.7 mM Na$_2$HPO$_4$; without CaCl$_2$, without MgCl$_2$; pH=7.2±0.1), which was obtained from GIBCO BRL (Grand Island, N.Y.).

The hydrazide end of EMCH (0.02 g/mL) was first reacted with the —COO$^-$ groups in the hyaluronic acid (HyA) chains (1 mg/mL) using 1-ethyl-3-(3-dimethylaminopropyl) carbodiimide (EDC; Pierce, 0.4 mg/mL) and N-hydroxysulfosuccinimide (Sulfo-NHS, Pierce, 1.1 mg/mL) in 2-(N-morpholino) ethanesulfonic acid, 0.9% NaCl, conjugation buffer (MES, Pierce, 0.1M, pH 6.5) for 1 hour at 22° C. The unreacted components were removed via dialysis, the product was lyophilized, and then the maleimide end of EMCH was reacted with the -SH groups of bsp-RGD(15) in 0.1M sodium phosphate buffer (pH 6.6) for 4 hours at 22° C. The product was lyophilized, and the functionalized HyA chains were used to synthesize the semi-IPNs, as detailed below.

The functionalized HyA (25 mg) was dissolved in 15 mL iPBS along with 5% w/v total of NIPAAm, mPEG200MA, and PEG200DA, followed by bubbling the solution with dry nitrogen gas for 30 minutes to remove dissolved oxygen. Following the nitrogen purge, 279 uL of 10% w/v AP (27.9 mg, 0.122 mmol) and 183 uL TEMED (142 mg, 1.22 mmol) were added as the initiator and accelerator, respectively, to the solution, which was then gently mixed. The monomer solution was allowed to polymerize at room temperature for 18 hours under a dry nitrogen atmosphere. The sample sIPN hydrogel compositions and properties are listed in Table 2 below.

TABLE 2

| | Example 8 sample sIPN compositions | | | | | |
|---|---|---|---|---|---|---|
| | NIPAAm mol % | PEG200DA mol % | mPEG200MA mol % | 22 C G* (Pa) | 37 C G* (Pa) | LCST (C) |
| Sample 8A | 98.7 | 1.0 | 0.3 | 68.6 | 1970 | 32.9 |
| Sample 8B | 98.4 | 1.0 | 0.6 | 64.4 | 32300 | 32.9 |
| Sample 8C | 96.1 | 1.0 | 2.9 | 44.1 | 91500 | 33.6 |

Example 9

Hydrolytically-Degradable sIPN of p(NIPAAm-co-AAc) Interpenetrated by Peptide-Functionalized Linear HyA

This example defines a p(NIPAAm-co-AAc) sIPN with a hydrolytically cleavable crosslinker. The water-soluble crosslinker was a telechelic molecule composed of poly(ethylene glycol) (PEG) flanked at both ends with either poly(lactide) (PL), poly(ε-caprolactone) (PEC), or a copolymer of each. The ends of the chain were acrylated using acryloyl chloride and triethylamine (TEA) as described for the enzymatically degradable crosslinker. In one synthesis, the average molecular weight of the crosslinker was approximately 8000 g/mol, and the molar ratio of the PEG, PL and PEC was 1:5:0.5. The materials used to synthesize the sIPN include NIPAAm, AAc, ammonium peroxydisulfate (AP), and N,N,N',N'-tetramethylethylenediamine (TEMED) obtained from Polysciences, Inc. (Warrington, Pa.), as well as incomplete Dulbecco's Phosphate-Buffered Saline (iPBS; 1.51 mM $KH_2PO_4$, 155 mM NaCl, and 2.7 mM $Na_2HPO_4$; without $CaCl_2$, without $MgCl_2$; pH=7.2±0.1), which was obtained from GIBCO BRL (Grand Island, N.Y.). NIPAAm (96 mol %), AAc (2 mol %), and the crosslinker (2 mol %) were polymerized in iPBS in the presence of bio-functionalized HyA chains (see, Example 8) for 19 hours at RT. This sIPN degrades in approximately 15-25 days.

Example 10

Hydrolytically-degradable sIPN of p(NIPAAm-co-EG200) Interpenetrated by Peptide-Functionalized Linear pAAc

This example defines a sIPN of p(NIPAAm-co-EG200) with a hydrolytically cleavable crosslinker. The water-soluble crosslinker was a telechelic molecule composed of poly(ethylene glycol) (PEG) flanked at both ends with either poly(lactide) (PL), poly(ε-caprolactone) (PEC), or a copolymer of each. The ends of the chain were acrylated using acryloyl chloride and triethylamine (TEA) as described for the enzymatically degradable crosslinker. The materials used to synthesize the sIPN include NIPAAm, methoxy poly(ethylene glycol) (MW=200) methacrylate (mPEG200MA) (MW=300 g/mol), ammonium peroxydisulfate, and N,N,N',N'-tetramethylethylenediamine obtained from Polysciences, Inc. (Warrington, Pa.), as well as incomplete Dulbecco's Phosphate-Buffered Saline (iPBS; 1.51 mM $KH_2PO_4$, 155 mM NaCl, and 2.7 mM $Na_2HPO_4$; without $CaCl_2$, without $MgCl_2$; pH=7.2±0.1), which was obtained from GIBCO BRL (Grand Island, N.Y.). NIPAAm (96 mol %), mPEG200MA (3 mol %), and the crosslinker (1 mol %) were polymerized in iPBS in the presence of bio-functionalized pAAc chains (see, Example 7) for 19 hours at RT.

Example 11

Hydrolytically-Degradable sIPN of p(NIPAAm-co-EG200) Interpenetrated by Peptide-Functionalized Hyaluronic Acid (HyA)

This example defines a sIPN of p(NIPAAm-co-EG200) with a hydrolytically cleavable crosslinker. The water-soluble crosslinker was a telechelic molecule composed of poly(ethylene glycol) (PEG) flanked at both ends with either poly(lactide) (PL), poly(ε-caprolactone) (PEC), or a copolymer of each. The ends of the chain were acrylated using acryloyl chloride and triethylamine (TEA) as described for the enzymatically degradable crosslinker. The materials used to synthesize the sIPN include NIPAAm, methoxy poly(ethylene glycol) (MW=200) methacrylate (mPEG200MA) (MW=300 g/mol), ammonium peroxydisulfate, and N,N,N',N'-tetramethylethylenediamine obtained from Polysciences, Inc. (Warrington, Pa.), as well as incomplete Dulbecco's Phosphate-Buffered Saline (iPBS; 1.51 mM $KH_2PO_4$, 155 mM NaCl, and 2.7 mM $Na_2HPO_4$; without $CaCl_2$, without $MgCl_2$; pH=7.2±0.1), which was obtained from GIBCO BRL (Grand Island, N.Y.). Grafting of biomolecules to HyA chains was achieved in the following manner. The hydrazide end of EMCH (0.02 g/mL) was first reacted with the —COO⁻ groups in the HyA chains (1 mg/mL) using 1-ethyl-3-(3-dimethylaminopropyl) carbodiimide (EDC; Pierce, 0.4 mg/mL) and N-hydroxysulfosuccinimide (Sulfo-NHS, Pierce, 1.1 mg/mL) in 2-(N-morpholino) ethanesulfonic acid, 0.9% NaCl, conjugation buffer (MES, Pierce, 0.1M, pH 6.5) for 1 hour at 22° C. The unreacted components were removed via dialysis, the product was lyophilized, and then the maleimide end of EMCH was reacted with the SH groups of the bsp-RGD(15) in 0.1M sodium phosphate buffer (pH 6.6) for 4 hours at 22° C. These functionalized chains are termed HyA-graft-bsp-RGD(15). The product was lyophilized, and the functionalized HyA chains were used to synthesize the semi-IPNs, as detailed below. The HyA-graft-bsp-RGD(15) (125 mg) was dissolved in 50 mL iPBS along with 2.194 g NIPAAm (19.4 mmol), 0.306 g mPEG200MA (1.02 mmol), and the hydrolytically-degradable crosslinker (1 mol %), followed by bubbling the solution with dry nitrogen gas for 30 minutes to remove dissolved oxygen. Following the nitrogen purge, 279 uL of 10% w/v AP (27.9 mg, 0.122 mmol) and 183 uL TEMED (142 mg, 1.22 mmol) were added as the initiator and accelerator, respectively, to the solution, which was then gently mixed. The monomer solution was allowed to polymerize at room temperature for 18 hours under a dry nitrogen atmosphere.

Example 12 sIPN of Hyaluronic Acid Graft EMCH Using Dithiol Crosslinkers Interpenetrated by Peptide-Functionalized Hyaluronic Acid

Linear HyA chains were activated for crosslinking in the following manner. The hydrazide end of EMCH (0.02 g/mL) was reacted with the —COO⁻ groups in the HyA chains (1 mg/mL) using 1-ethyl-3-(3-dimethylaminopropyl) carbodiimide (EDC; Pierce, 0.4 mg/mL) and N-hydroxysulfosuccinimide (Sulfo-NHS, Pierce, 1.1 mg/mL) in 2-(N-morpholino) ethanesulfonic acid, 0.9% NaCl, conjugation buffer (MES, Pierce, 0.1M, pH 6.5) for 1 hour at 22° C. The unreacted components were removed via dialysis, the product was lyophilized. These HyA chains with maleimide terminated grafts of EMCH can be reacted with any dithiol containing molecule to generate a crosslinked network. When the network is crosslinked in the presence of a linear biofunctionalized chain, i.e. HyA, a sIPN is formed. Specifically, di-thiol poly(ethylene glycol) (MW 3400) (Nektar, Huntsville, Ala.) and biofunctionalized HyA were combined at final concentrations ranging from 1 to 33 mg/mL to the maleimide activated HyA chain solution. Gelation rates depend on the range of crosslinker concentrations and can be as short as 10 mins. By modulating the amount of crosslinker (i.e., either the concentration of the dithiol molecule or degree of grafting of the HyA chain), the mechanical properties of the sIPN can be tuned.

Example 13

Maintenance of hESCs on sIPNs of (p(NIPAAm-co-AAc) with Enzymatically-Degradable Crosslinks

In this example, hESCs were grown on a sIPN consisting of loosely crosslinked poly (N-isopropylacrylamide-co-acrylic acid) (p(NIPAAm-co-AAc)). The p(NIPAAm-co-AAc) was crosslinked with an acrylated peptide (QPQGLAK-NH$_2$; SEQ ID NO: 20), a sequence designed to be cleaved by matrix metalloproteinase-13 (MMP-13) and other collagenases. A sIPN was synthesized by the addition of p(AAc)-graft-bsp-RGD(15), to provide cell binding domains, during the polymerization of p(NIPAAm-co-AAc). An important feature of this sIPN is that the gel stiffness is tunable by varying the concentration of: (a) the crosslinker, and (b) of the linear p(AAc)-graft-bsp-RGD(15) chains.

Protease-labile crosslinkers not only contribute to the overall mechanical properties of the sIPN, but they also affect the degradation rate. The Gln-Pro-Gln-Gly-Leu-Ala-Lys (QPQGLAK) (SEQ ID NO: 20) diacrylate used as a peptide crosslinker was designed to enable the cell-mediated proteolytic remodeling to occur within the sIPNs. Michaelis-Menten parameters, K$_m$ and k$_{cat}$, were determined for the cleavage of candidate peptide crosslinker in solution by activated human recombinant MMP-13 and a general collagenase from *Clostridium histolyticum* by using an HPLC peak area detection protocol (Table 4). Within the timeframe measured, Lineweaver-Burk plots were linear and therefore obeyed Michaelis-Menten conditions for the concentrations studied.

The degradation rate of the sIPNs can be adjusted by using alternative peptide crosslinkers with higher k$_{cat}$/K$_m$ ratios (Table 4), [3]. In addition, sIPNs can be constructed with more than one type of peptide crosslinker (each with a different protease degradation rate) to generate heterogeneously degrading sIPNs. A variety of peptide based MMP substrates can be chosen from to control the degradation rate of a cross linked sIPN, allowing for matching the rate of hydrogel degradation to the local biological application. We have chosen three sequences that will allow for a slow, moderate, and fast degradation by MMP-13 with specificity over other collagenases, MMP-2 and MMP-9. The first peptide crosslinker, allowing for a slow rate of MMP-13 cleavage, is a 6 amino acid sequence (QPQGLAK) (SEQ ID NO: 20) suitable for acrylation and incorporation into a polymer network by free radical polymerization. The second and third peptide sequences listed (GPLGLSLGK; SEQ ID NO: 21 and GPLG-MHGK; SEQ ID NO: 22), based on sequences in Table 4, have been selected as also being suitable for acrylation and polymerization, as well for faster cleavage rates by MMP-13 activity.

Polymerization follows that outlined in Example 7 with the exception that BIS is replaced by the peptide crosslinker. For a p(NIPAAm-co-AAc) crosslinked with QPQGLAK; SEQ ID NO: 20, the LCST phase transition was determined using an UV-vis spectrophotometer by monitoring the transmittance of visible light (λ=500 nm) as a function of temperature. The sIPN undergoes a LCST at ~35° C. The mechanical and viscoelastic properties of the sIPNs were characterized by dynamic oscillatory shear measurements, using a parallel

TABLE 4

The digestion kinetics of QPQGLAK (SEQ ID NO: 20) by recombinant human (rh) MMP-13 and *C. histolyticum* collagenase in our studies were measured by HPLC and compared to the digestion of other peptide substrates by MMP-13 (Lauer-Fields et al., *J. Biol. Chem.*, 275(18): 13282-90 (2000); (Mitchell, et al., *J. Clin. Invest.*, 97(3): 761-8. (1996); (Deng, et al., *Journal Of Biological Chemistry*, 275(40): 31422-31427 (2000)). The cleavage site is between amino acids P$_1$ and P$_1$'. The selectivity of MMP-13 for the substrates is indicated by comparing k$_{cat}$/K$_m$ for MMP-13 with other MMPs. The sequences taken from literature studies were determined from phage display studies (Deng, et al., *Journal Of Biological Chemistry*, 275(40): 31422-31427 (2000)).

| Name | Enzyme | Substrate | P$_4$ | P$_3$ | P$_2$ | P$_1$ | P$_1$' | P$_2$' | P$_3$' | P$_4$' | k$_{cat}$/K$_m$ (s$^{-1}$M$^{-1}$) | Selectivity (k$_{cat}$/K$_m$ ratio for MMP-13 to MMP-x) MMP-1 | MMP-9 | MMP-3 |
|---|---|---|---|---|---|---|---|---|---|---|---|---|---|---|
| Coll II-H1 | rh MMP-13 | SEQ ID NO: 20 | Q | P | Q | G | L | A | K | | 729 | | | |
| Coll II-H1 | collagenase | SEQ ID NO: 20 | Q | P | Q | G | L | A | K | | 32 | | | |
| CP | rh MMP-13 [3] | SEQ ID NO: 23 | G | P | L | G | M | R | G | L | 4.22 × 10$^6$ | 820 | 11 | 1300 |
| C2-22 | rh MMP-13 [3] | SEQ ID NO: 24 | G | P | R | P | F | N | Y | L | 1.08 × 10$^6$ | 180 | 21 | 7.9 |
| C5-27 | rh MMP-13 [3] | SEQ ID NO: 25 | G | P | F | G | F | K | S | L | 5.11 × 10$^5$ | 2900 | 4.8 | 250 |
| C2-12P3A | rh MMP-13 [3] | SEQ ID NO: 26 | G | A | L | G | L | S | L | | 3.53 × 10$^4$ | 8.3 | 4.6 | 14 |
| C3-16 | rh MMP-13 [3] | SEQ ID NO: 27 | G | P | K | G | V | Y | S | L | 1.6 × 10$^6$ | 5500 | 2.2 | 3600 |
| Coll II | rh MMP-13 [2] | SEQ ID NO: 28 | G | P | Q | G | L | A | G | Q | 3194 | | | |
| | rh MMP-13 [1] | Synthetic triple helical peptide | | | | | | | | | 3293 | | | |

Figure 9:
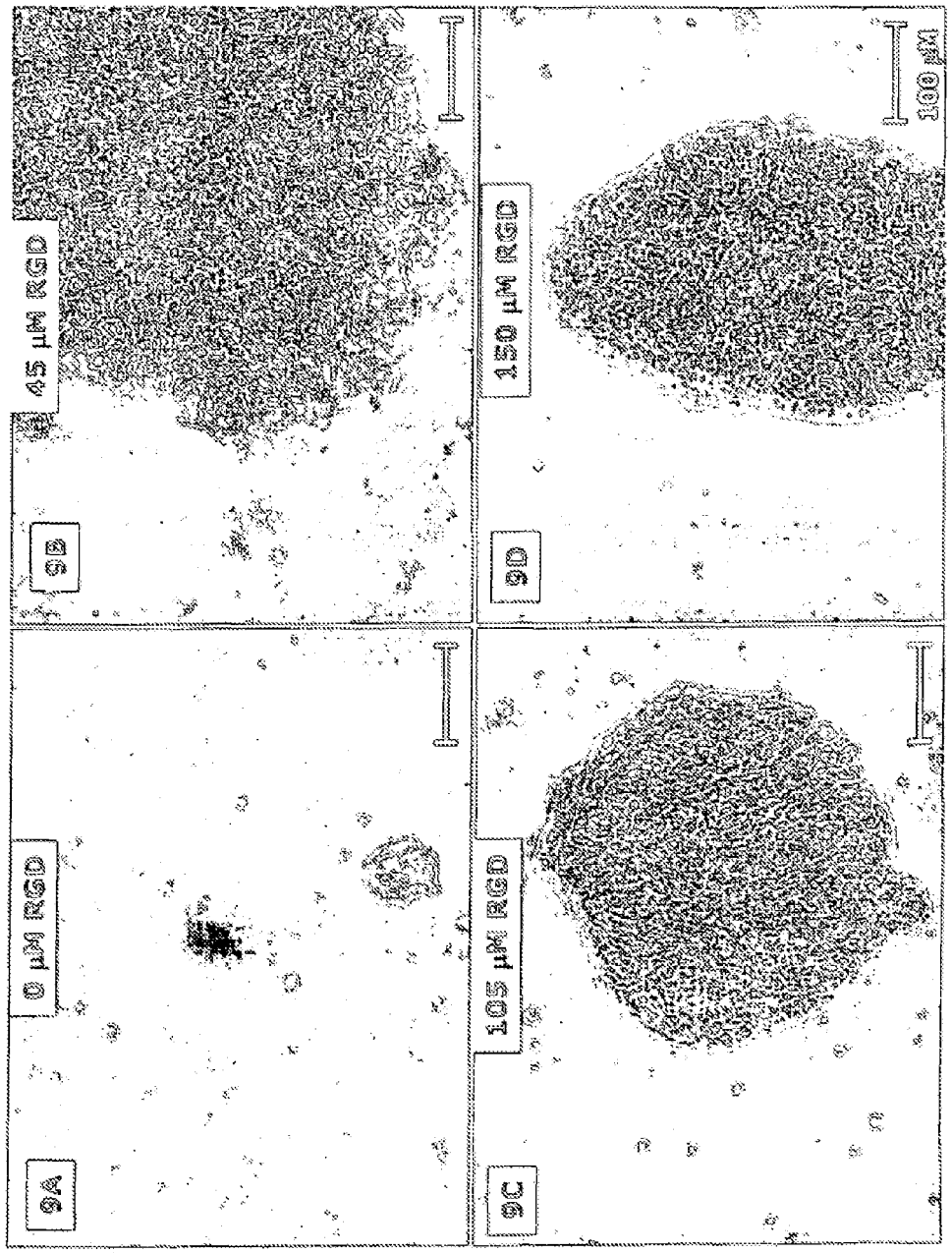
FIG. 9 hESCs cultured on sIPN of various RGD adhesion ligand concentrations. (A, B, C, D)=0, 45, 105, 150 μM, respectively. At 0 μM RGD concentration, very low hESC adhesion was observed. At 45 μM RGD concentration, colony morphology was highly variable, where some colonies exhibited tight borders while other did not. Qualitatively, hESCs cultured on sIPNs of higher RGD concentrations (105 and 150 μM) exhibited morphologies most similar to undifferentiated hESCs.
Figure 10:
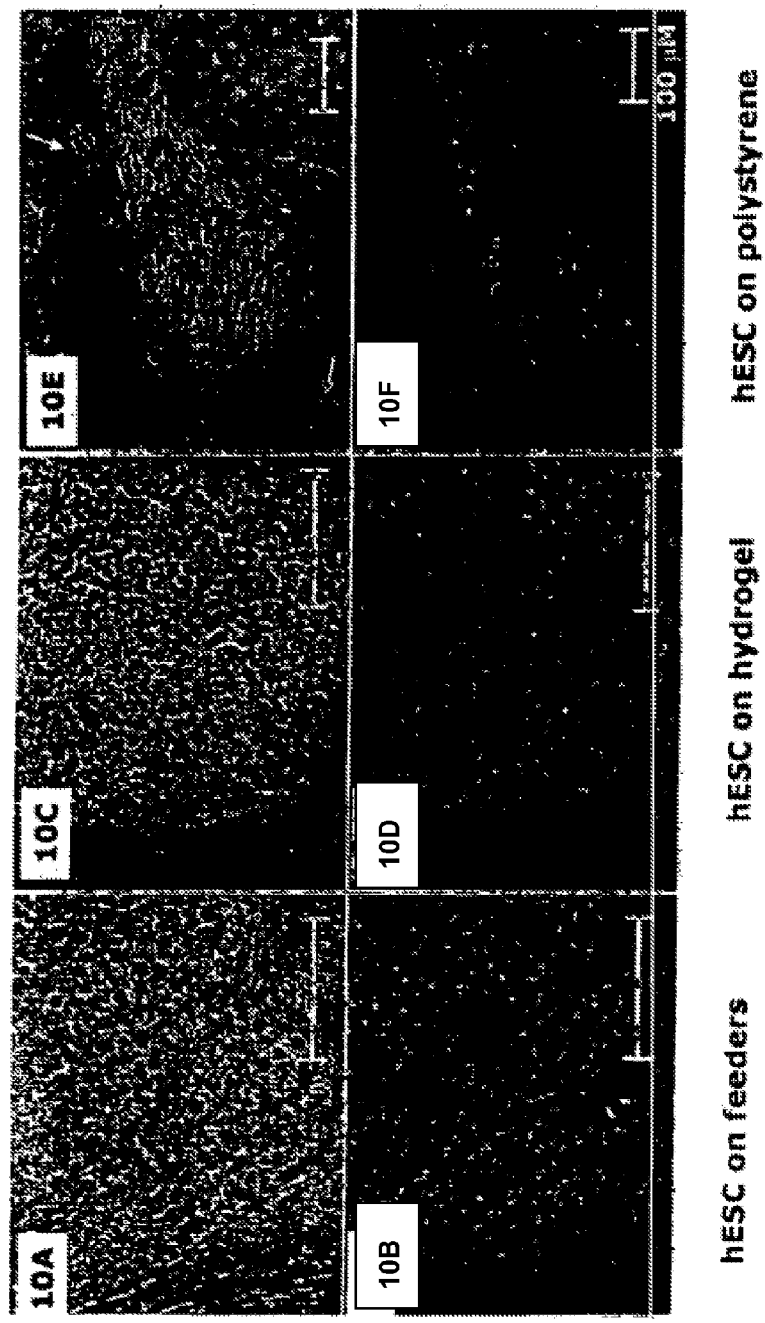
FIG. 10 Morphology and OCT-4 immunofluorescence of hESCs at Day 5. (A, B) hESCs cultured on MEFs exhibited small, tightly packed cells with distinct colony borders. (C, D) hESCs cultured on sIPN (|G*|~70 Pa, 150 μM RGD) exhibited similar morphologies when compared to (A, B). (E, F) hESCs cultured on gelatin-adsorbed polystyrene exhibited morphologies of spontaneously differentiating cells, with spindle-shaped cells and indistinct colony borders. OCT-4 was present in some cells under all three conditions. However, note that in hESCs cultured on polystyrene (F), white arrows point to cells beyond the colony edge which were not positive for OCT-4.
Figure 11:
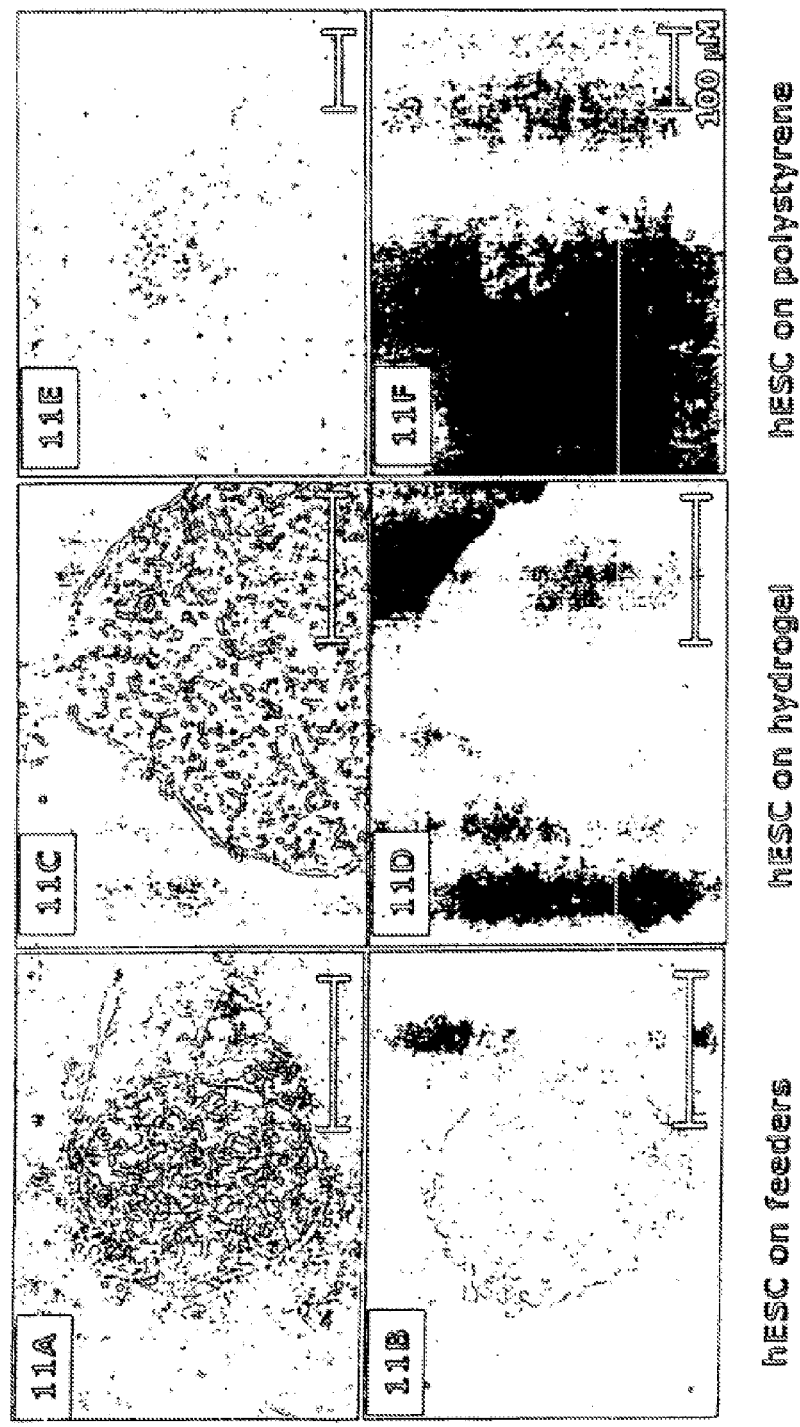
FIG. 11 Morphology and SSEA-4 immunofluorescence of hESCs at Day 5. (A, B) hESCs cultured on MEFs. (C, D) hESCs cultured on sIPN (|G*|~70 Pa, 45 μM RGD). (E, F) hESCs cultured on gelatin-adsorbed polystyrene. SSEA-4 was present in colonies under all three conditions.

1. (Lauer-Fields et al., *J. Biol. Chem.*, 275(18): 13282-90 (2000))
2. (Mitchell, et al., *J. Clin. Invest.*, 97(3): 761-8. (1996))
3. (Deng, et al., *Journal Of Biological Chemistry*, 275(40): 31422-31427 (2000))

plate rheometer (Paar Physica MCR 300). Rheological measurements were performed over a frequency range of 0.001 Hz 10 Hz to determine the complex modulus (G*) and loss angle. The mean G* at 22° C. at 1 Hz was 77.4 Pa ±30.3 (SE), and at 37° C. at 1 Hz was 129.1 Pa ±61.6 (SE). The sIPN was polymerized in 12-well plates and sterilized by the use of ethanol. hESCs were cultured on the sIPN surface and optimal hESC culture conditions were used. Complete culture medium (KSR) consisted of: Knockout-DMEM (Gibco), 20% Knockout Serum Replacement (Gibco), 2 mM Glutamine (Gibco), 0.1 mM non-essential amino acids (NEAA) (Gibco), 0.1 mM β-Mercaptoethanol (Sigma), and 4 ng/mL basic fibroblast growth factor (FGF)-2 (R&D Systems). On the sIPNs, hESCs are cultured using MEF-conditioned KSR. hESCs were evaluated by morphology, live/dead stain (calcein AM and Ethidium Homodimer), and immunofluorescence against the Oct-4 transcription factor, a highly specific and necessary hESC marker and SSEA-4, a cell surface marker for hESCS. The sIPN was able to support short-term hESC self-renewal in the absence of a mouse or human feeder layer. hESCs were cultured on sIPN of four RGD adhesion ligand concentrations of 0, 45, 105, 150 µM (FIG. 9). The hESC colonies were morphologically intact and live/dead stain indicated a combination of living and dead cells. Finally, immunofluorescence revealed positive Oct-4 and SSEA-4 expression in the hESC colonies (FIGS. 10 and 11), an indication the hESCs retained their undifferentiated state.

Example 14

Figure 8A:
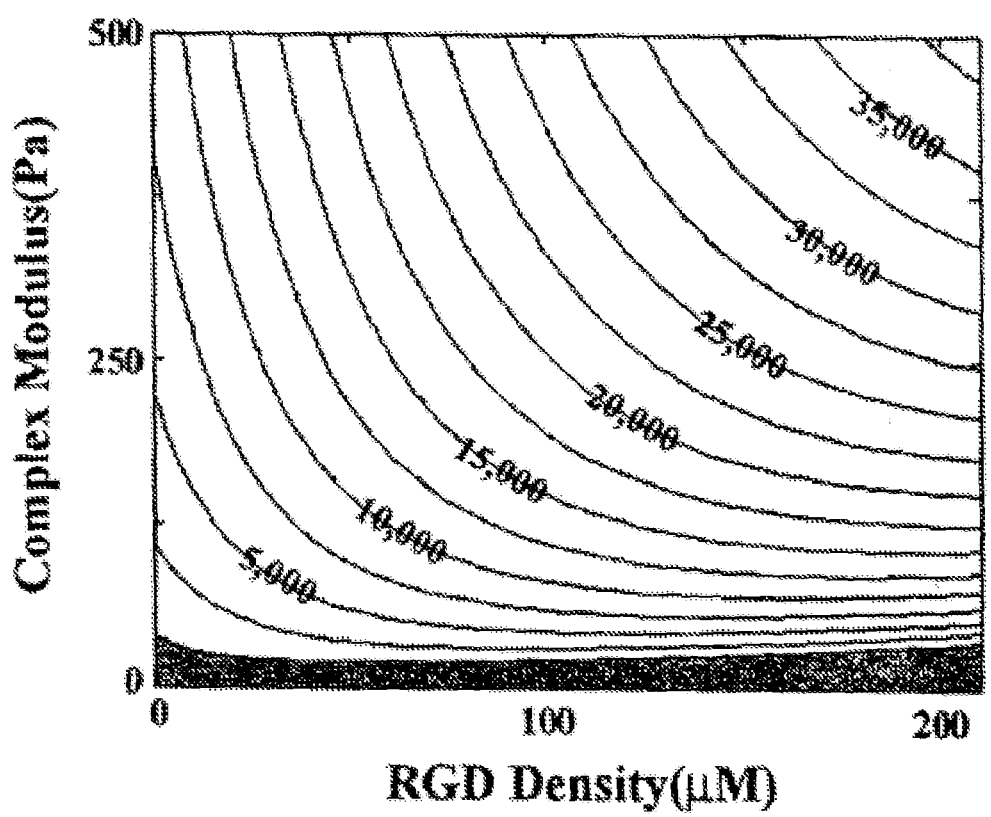
FIG. 8 Constant contour plot (left) and 3D empirical response surface (right) for cell proliferation (cells/cm$^2$) on sIPNs as a function of G* and bsp-RGD(15) concentration after 5d of culture. G* were measured at 37° C. at 5% strain at 1 Hz. bsp-RGD(15) was in the form of p(AAc)-g-bsp-RGD (15). The model had an R$^2$ value of 0.86 and indicated significant effects of [RGD] ($p<0.05$) and G* ($p<0.05$).
Figure 8B:
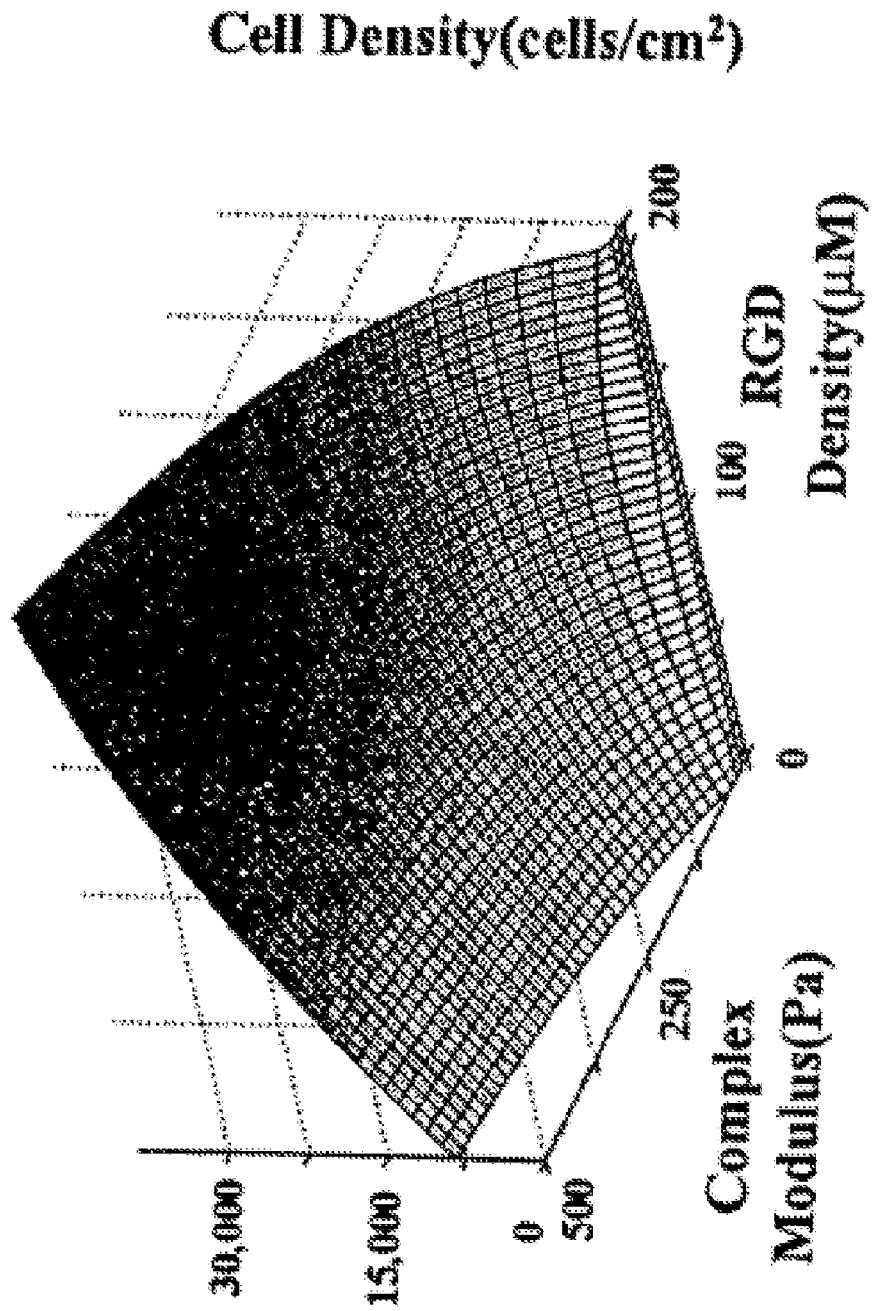

To assess cell proliferation on sIPNs with different complex shear moduli (G*) and bsp-RGD(15) ligand concentration a series of protease-degradable sIPNs were synthesized while modulating the bsp-RGD(15) concentration and G* (measured at 1 Hz at 37° C.). In 96 well plates, sIPNs were sterilized in 70% ethanol and washed 3 times with PBS at 37° C. Cells isolated from newborn rat calvaria were seeded onto the surface of each sIPN at a surface density of 6000 cells/cm$^2$ and maintained with DMEM supplemented with 15% FBS, 1 mM sodium pyruvate, 5 µg/ml ascorbic acid, 150 nM dexamethasone, 1% fungizone and 1% penicillin-streptomycin. Cell density was quantified with the WST-1 cell proliferation reagent after 5 days in culture. Cell proliferation data were plotted as a function of bsp-RGD(15) concentration and G*, and were fit using a least squares regression with JMP(SAS) software (Cary, N.C.), (FIG. 8). Significant effects of RGD concentration ($p<0.05$) and G* ($p<0.05$) were observed. The 2D contour plot identifies lines of constant proliferation (cells/area) based on the independent variable or factors bsp-RGD(15) concentration and G*. The shaded region in the 2D contour plot represents zero cells/cm$^2$, thus factor combinations in this region don't support cell proliferation and may induce apoptosis. An interaction effect is evident from both plots and suggests the ligand is active in the sIPNs, even after radical polymerization.

Example 15

Method for Stem Cell Recovery with Using Enzymes for Enzymatically Degradable sIPNs This example describes a method for harvesting hESC grown on enzymatically-crosslinked sIPNs. Human ESCs can be grown on thermoreversible and enzymatically-degradable sIPNs as defined in Example 13. Enzymatically degradable sIPNs were polymerized in 6-well plates and sterilized by the use of ethanol. The hESCs were cultured on the sIPNs using MEF-conditioned complete culture medium (KSR) consisting of: Knockout-DMEM (Gibco), 20% Knockout Serum Replacement (Gibco), 2 mM Glutamine (Gibco), 0.1 mM non-essential amino acids (NEAA) (Gibco), 0.1 mM β-Mercaptoethanol (Sigma), and 4 ng/mL basic fibroblast growth factor (FGF)-2 (R&D Systems). The hESCs can be harvested by using MMP enzymes to degrade the enzymatically-degradable crosslinks. Enzymes are added to the culture system for 3040 minutes to degrade the edsIPN sIPN and release the hESCs.

Example 16

This is an example of a novel method to harvest hESCs from a sIPN culture surface. Currently, hESCs are detached from the culture surface (feeder layer/matrigel) using collagenase and other enzymes. These enzymes are derived from animal products, which raise concerns about disease transmission. The sIPN system offers two novel methods for detachment and retrieval of hESCs. First, the sIPN undergoes a LCST whereby the change in volume can disrupt the cell adhesion to the material and release the hESCs from the sIPN surface. In this case, hESCs are cultured on the sIPN at 37° C. The culture system is then placed in a environment below the LCST temperature for the sIPN for 10-30 minutes to retrieve the hESCs. Since the sIPN undergoes a LCST transition, whereby the change in volume can release the hESCs from the sIPN surface, reducing the temperature below the LCST releases the hESCs from the substrate. Cells are then collected.

Example 17

Neural Cells on sIPN

In this example, rat adult neural stem cells were grown on a sIPN consisting of loosely crosslinked poly(N-isopropylacrylamide-co-acrylic acid) (p(NIPAAm-co-AAc)). The p(NIPAAm-co-AAc) was crosslinked with an acrylated peptide (QPQGLAK-NH$_2$), a sequence designed to be cleaved by matrix metalloproteinase-13 (MMP-13) and other collagenases. In addition, a semi-interpenetrating polymer network was synthesized by the addition of 60 µM polyacrylic acid-graft-bsp-RGD (15), to provide cell binding domains, during the polymerization of p(NIPAAm-co-AAc). An important feature of this sIPN is that the gel stiffness is tunable by varying the concentration of: (a) the crosslinker, and (b) of the linear p(AAc)-graft-bsp-RGD (15) chains. The sIPN undergoes a lower critical solution temperature (LCST) at ~32-35° C. Rheological measurements were performed over a frequency range of 0.001 Hz-10 Hz to determine the complex modulus (G*) and loss angle. The mean G* at 22° C. at 1 Hz was 24.40Pa±2.0 (SD), and at 37° C. at 1 Hz was 87.40 Pa±2.1 (SD). The sIPN was polymerized in 96-well plates and sterilized by the use of ethanol.

Figure 12A:
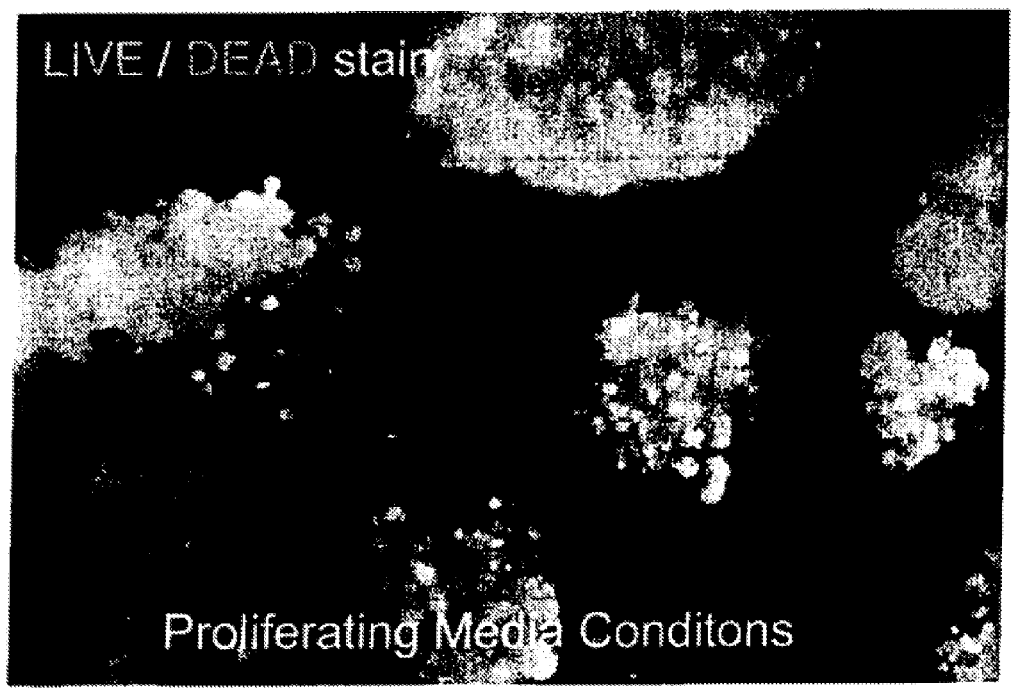
FIG. 12 Semi-IPNs support NSC proliferation but not differentiation. NSCs after 15 days on a p(NIPAAm-co-AAc) semi-IPNs with p(AAc)-g-RGD linear chains in either a, proliferating (1.2 nM bFGF) media conditions or b, differentiating (1 μM retinoic acid, 5 μM forskolin) media conditions. The semi-IPN properties were 60 μM polyacrylic acid-graft-RGD (p(AAc)-g-RGD) and the mean G* at 22° C. at 1 Hz was 24.40 Pa ~2.0 (SD), and at 37° C. at 1 Hz was 87.40 Pa ~2.1 (SD). Using a live/dead stain (calcein AM and Ethidium Homodimer), the green represents living cells while the red represent necrotic cells.
Figure 12B:

NSCs were cultured on the sIPN surface under conditions listed in Example 4, either in 20 ng.ml$^{-1}$ basic fibroblast growth factor (bFGF) for cell proliferation or 1 µM retinoic acid with 5 µM forskolin for neuronal differentiation. NSCs were evaluated by morphology and a live/dead stain (calcein AM and Ethidium Homodimer, Molecular Probes, Eugene, Oreg.). After 15 days, the sIPN was able to support NSC self-renewal with few necrotic cells (FIG. 12a). In contrast, NSC were not able to differentiate well within the sIPN, as evidenced by a large percentage of necrotic cells (FIG. 12b). Thus, this example defines an alternative embodiment for conditions for self-renewal of NSCs, but not differentiation of these cells. This example also demonstrates the sensitivity of NSC to differentiation conditions is modulus dependent.

Example 18

Introduction

This proposed research project seeks to theoretically evaluate a novel potential alternative treatment with an advanced computational model of the heart. The proposed treatment approach uses an advanced injectable network (IPN or sIPN), with the overall goal both to give short term mechanical support of damaged cardiac tissue, lowering local fiber stress in the infarct borderzone to prevent infarct expansion, as well as to foster functional growth of neotissue in the damaged region to help improve long term cardiac function. Specifically, novel advanced materials (IPN or sIPN) suitable for direct injection into the borderzone of an infarct region may provide stabilization by thickening of the local cardiac wall, which would be followed by tissue regeneration. In an exemplary embodiment, this network (IPN or sIPN) can consist of a thermoresponsive polymer hydrogel, modified to allow for direct cellular attachment and stimulation of angiogenesis, and is suitable for the support of transplanted myocyte precursor cells as well.

Project Specific Aims

Our lab currently is working with a thermoresponsive hydrogel for the purposes of tissue engineering. This hydrogel consists of a copolymer of N-Isopropyl acrylamide(NIPAAm) and acrylic acid (AAc), and is non protein fouling and non immunogenic. When cross-linked, this copolymer (NIPAAm-co-AAc) exhibits lower critical solution temperature (LCST) phase behavior, where upon warming to body temperature (37C), the material undergoes phase stiffening from the entropic expulsion of water, changing from a viscous, flowable material to a stiff viscoelastic material with a complex modulus of approx 0.2-1.5 kPa. This material is also designed for a specific mode of biodegradation, where it is only replaced by incoming or expanding transplanted cell populations. This is as the cross links used to create the hydrated network are constructed from the MMP degradable amino acid sequence QPQGLAK[2]; SEQ ID NO: 20. As cells encounter and move into the hydrogel, they slowly degrade it by breaking the gel cross links, allowing for loss of structural integrity only as cells physically replace the macrostructure of the material.

In addition, this material is modified by the incorporation of the linear polymer chain poly acrylic acid (pAAc) during polymerization to create a semi-interpenetrating network (sIPN).[3] This allows for simple functionalization of the hydrogel by direct modification of the pAAc with cellular binding domains and growth factors. In this work, the use of the ubiquitous binding domain -RGD- is used as well as the growth factor Sonic Hedgehog (Shh). This recombinantly produced Shh is a potent protein growth factor[4] and is chemically incorporated into the synthetic interpenetrating network and will stimulate the growth of new blood vessels into the implant. This will allow for the nutrient supply for any additional cellular regeneration from circulating stem cells, or for feeding of precursors loaded into the gel.

This project is a proposal for using an advanced finite element model (FEM) simulation to investigate the initial events surrounding the injection of the hydrogel into a damaged heart. It is hypothesized that direct injection of this hydrogel into the borderzone tissue will allow thickening and strengthening of the cardiac wall, and relieve local fiber stress. The material will become directly integrated into the cardiac tissue, as integrated cellular binding sites will allow for binding and force transduction. Therefore, this is hypothesized to allow for a reduction of load on the local muscle fibers during diastolic filling and systolic expulsion. By using an advanced mechanical model of cardiac function, this effect of injection of a thermostiffening hydrogel into the borderzone of an infracted heart can be examined. The global function of the heart will be evaluated through computed stroke volume and the Starling relation, and local changes in stresses in the muscle fiber direction will be evaluated in the infarct, borderzone, and remote regions. Differing geometries reflecting changes in hydrogel injection patterns, as well as differing stiffness of the thermoresponsive hydrogel will be used to determine the overall effect of injection of the gel.

Background and Significance

Because of deficiencies in medical treatment available for heart failure patients, innovative surgical procedures that reduce left ventricular size or change LV shape are being investigated. Partial left ventriculectomy, or the Bautsista procedure[5], reduces LV volume and wall stress, but significantly reduces LV function as contractile elements tend to be removed.[6,7]

More recently, passive cardiac constraints (Acorn cardiac support device, Acorn Cardiovascular) and shape change therapy with a novel tensioning device (Myosplint, Myocor) are promising and lead to short term fiber stress reduction, but seem unlikely to lead to large improvements in LV function in the long term.[8,9] These devices are based on the notion that one large problem associated with a myocardial infarct is that the borderzone region surrounding the initial damage is not always stable, and after the attack the infarct can spread into this borderzone, effectively increasing the size, extent, and severity of the injury. There is considerable work as to why this is occurring in the literature[10,11,12], and it is hypothesized that the changes to the mechanical structure from the infarct can change the stress in the borderzone region, causing extension in the myocytes during systole which can lead to cellular apoptosis. Support devices such as the Acorn jacket and the Myosplint allow for a reduction of stress in the muscle fibers, which prevent the infarct from extending. However, these systems still do not address the loss of contractile elements within the injured heart, so while stabilizing, do not have any regenerative capability.

Tissue engineering is a promising new field that attempts to treat injuries such an AMI in a more comprehensive manner. The use of synthetic extracellular matrices (ECMs) as scaffolds for cellular regeneration is being actively researched and developed to treat injuries and genetic disorders. In addition, cellular transplantation of in vitro expanded populations of adult or embryonic precursor cells also is being explored to treat various disease states such as cardiac injury⁻. It is thought that through tissue engineering principles, loss of organ function, such as the cardiac damage sustained during an AMI, could be treated through cellular transplantation or material assisted regeneration. If designed properly in a cardiac system, such an effort may reap both the benefits of short term stabilization of damage, and also, long term LV functional improvement through the addition of new contractile elements, either from the bodies own ability to heal thorough circulating stem cells, or from direct transplantation of specific cell lines.

Research Design and Methods

An advanced cardiac finite element model (FEM) will be used to determine the effect of injection of biomimetic hydrogels on wall stresses in the infarct borderzone and any changes to global cardiac function. This model was previously developed specifically for use in LV mechanic simulations[14] and as such is has features not typically found in other mechanical simulation systems. It takes into account the anisotropic nature of cardiac muscle tissue, as well as the non-linear nature of its mechanics and the transmural distribution of cardiac muscle fiber orientation.

This FEM model will be used to examine the initial events surrounding the injection of a thermoresponsive hydrogel into the borderzone region of myocardial infarction. Although the long term regenerative ability of the hydrogel is a very important feature of the engineered implant, the first clinically relevant effect will be the reduction of stress in the local fiber orientation after the injection of the hydrogel and its subsequent LCST phase transition. This effect will be probed with FEM models of relevant cardiac geometries as well as global cardiac function that may be changed as well by the injection.

Cardiac Geometry Modeling

In order to examine the potential effect of the injected hydrogel, three different cardiac geometries will be investigated and compared. These geometries will reflect the following clinical conditions, using a sheep animal model—

Figure 19:
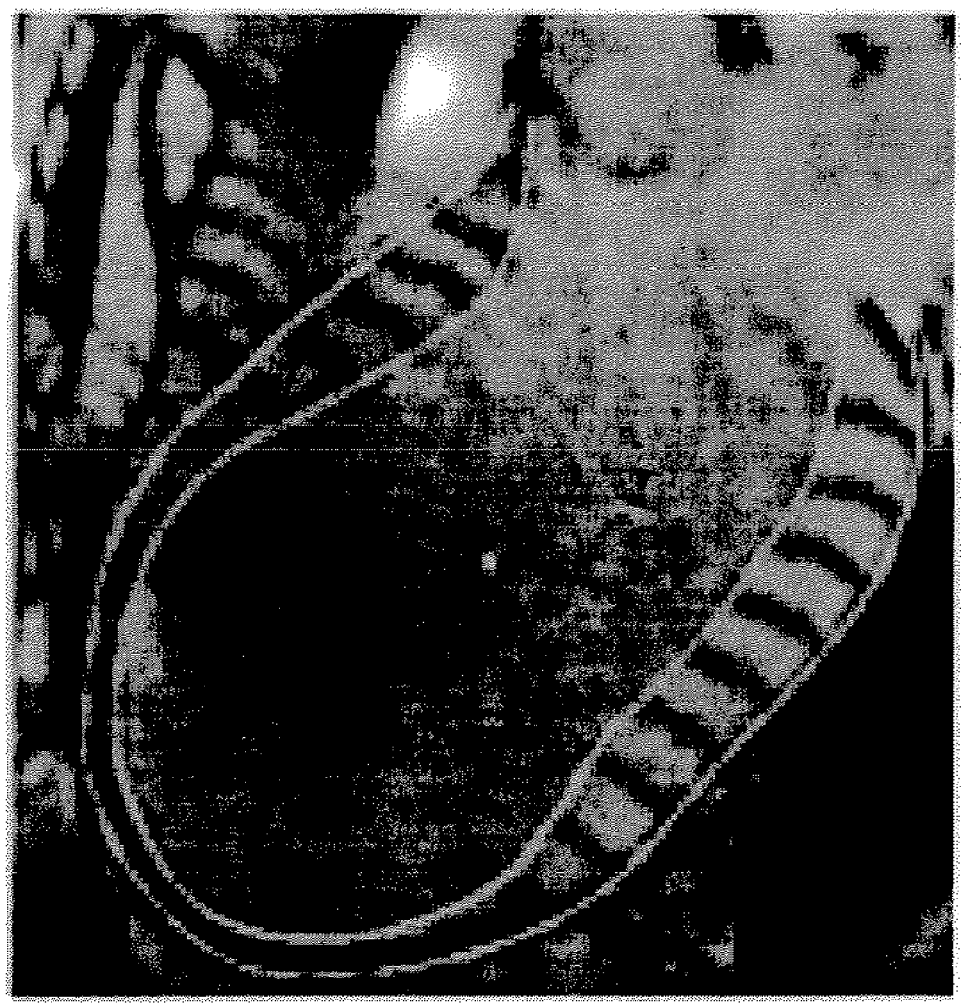
FIG. 19 is an MRI tagged image from infracted ovine cardiac tissue in left ventricle (Guccione et al[12]). 2D geometry can be measured for each such section and multiple sections used to construct 3D LV geometry. Aneurysm can be seen as a thinning towards the apex of the ventricle, and the borderzone is visible as the partially thinned region next to the aneurysm.

1. Healthy ovine left ventricle
2. Infarcted ovine left ventricle, where the coronary left anterior descending artery is ligated to create an aneurysm. This animal protocol has been previously described[12]
3. Infarcted ovine left ventricle as in 2, but with direct injection of hydrogel blebs into borderzone of the infarct The geometries used in the FEM model for the healthy sheep heart and the infracted heart will be configured as previously[12] through direct magnetic resonance imaging (MRI) of healthy and infracted sheep tissue. In this procedure, an animal is scanned and a series of MRI images are created. See FIG. 19. From the images, a reconstruction of the endocardium and epicardium surfaces can be traced and used to define the actual 3D geometry of the left ventricle wall and chamber volumes.

Figure 20:
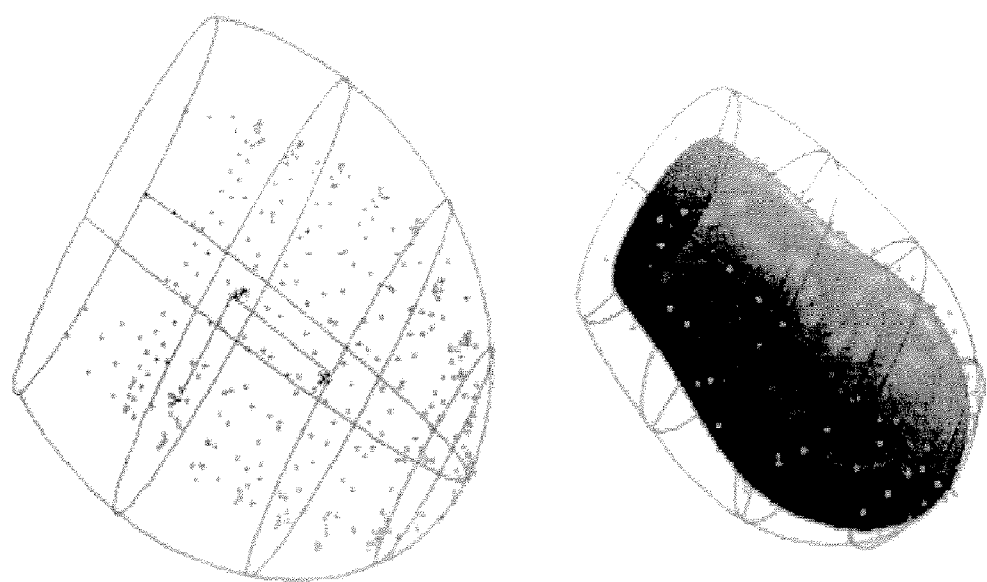
FIG. 20 is a depiction of fitting mesh to MRI data of an infracted sheep heart according to an exemplary embodiment of the invention; epicardial and endocardial surfaces are mapped and fit to a prolate spherical geometry. (Guccione et al[12])

This data is mapped onto a prolate spherical based geometry used in the FEM package. This volume is meshed into 11 longitudinal elements, 4 transmural elements, and 12 radial elements. The actual geometry of the inner prolate used to simulate the endocardium is modified point by point to minimize the difference between the actual data and the model. See FIG. 20.

Based on the MRI images, specific elements will be defined as normal tissue, borderzone region, or infarct region. These designations will be used in defining the element mechanical properties, and there will be assumed no variation in designation in the transmural direction (i.e. the infarct and borderzone are confluent transmurally). For the model, muscle fiber direction will be assumed to vary linearly from the endocardium to the epicardium, varying from 83 degrees to −37 degrees relative to the equator as determined from canine studies.[15]

Geometry 3, or the infracted heart with the hydrogel injection, will be accomplished by the modification of the mesh from geometry 2. In the defined borderzone, the mesh will be modified to accommodate bulging from the injection of a solid gel. Inner elements in the expanded zones will be fitted with mechanical properties of the hydrogel while keeping the same wall thickness in the region.

Figure 21:
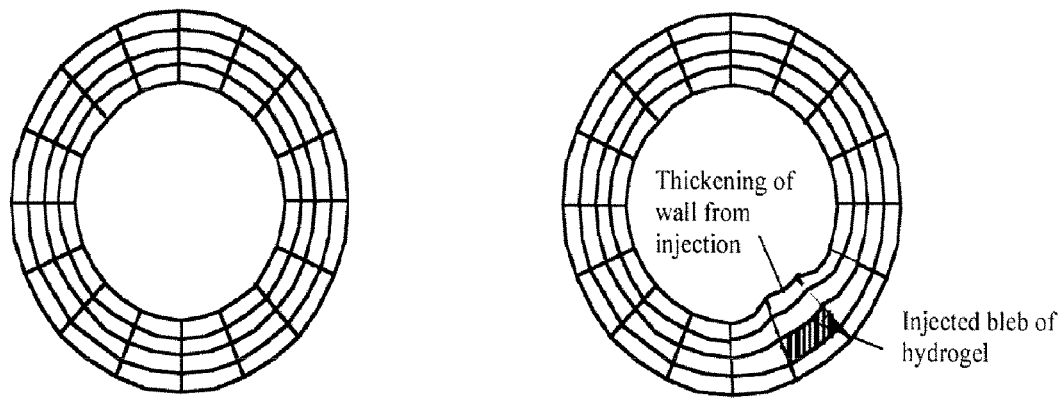
FIG. 21 is a depiction of mesh alteration to accommodate the bleb of hydrogel according to an exemplary embodiment of the invention. The model consists of 16 radial elements and 4 transmural elements.

In specific locations as shown in FIG. 21, the mesh will be altered so that the cardiac wall remains the same total thickness between the uninjected case and three elements of the injected case. One transmural element at the injection site will have its mechanical properties changed to that of the hydrogel. The hydrogel volume will be set so it increases wall thickness at the injection site by 25%.

Figure 22:
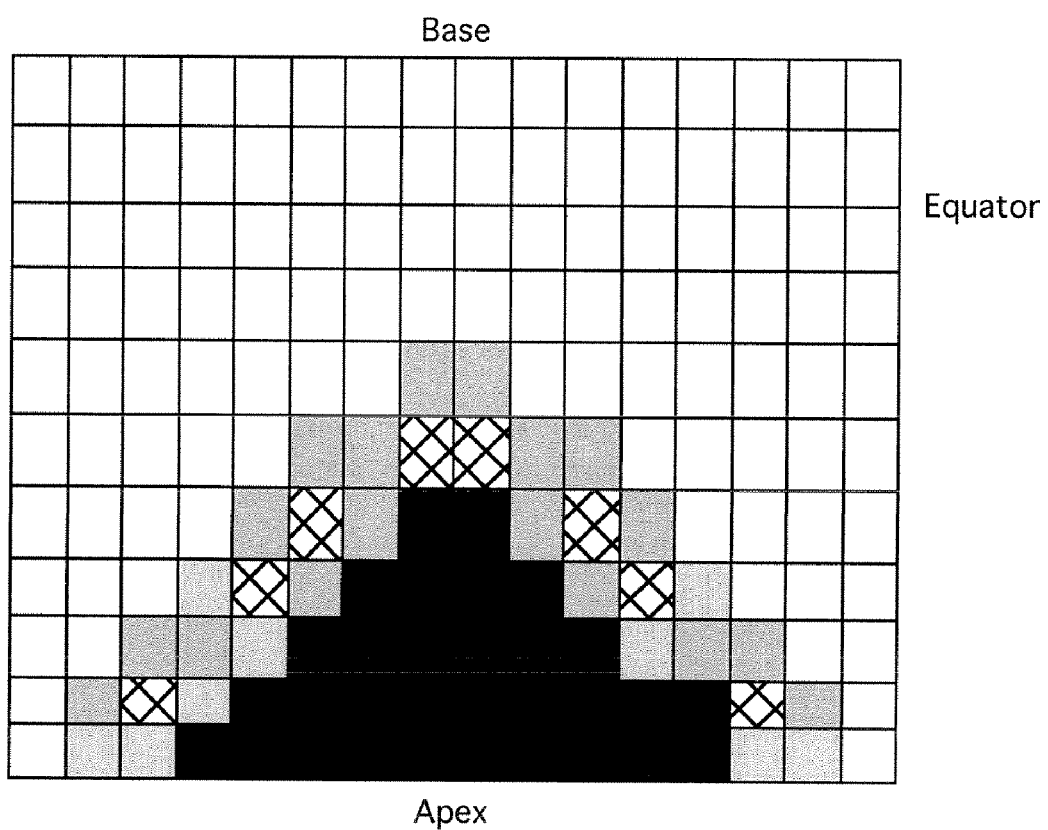
FIG. 22 is a depiction of a hydrogel injection pattern into the borderzone to be tested using the finite element model according to an exemplary embodiment of the invention. Dark sections indicate infarct region, gray zones indicate the borderzone, and cross-hatched regions indicate hydrogel injection points. Designations will be made based on the MRI images used to construct the mesh.

The patter of injection will follow those of the infarct. In FIG. 22, a sample representation is given, showing that gel will be administered in the borderzone of the infarct.

Defining Mechanical Properties

As the mechanical properties of muscle tissue are anisotropic (due to the muscle fiber orientation) and it exhibits non linear mechanics for relatively large produced strains in the cardiac cycle, a specialized set of equations is required to accurately depict its passive and active behavior.

To simulate the passive properties of cardiac muscle, the following strain energy function is used—

$$W = \frac{C}{2}(e^Q - 1), \tag{1}$$

where $$Q = b_f E_{ff}^2 + b_t(E_{cc}^2 + E_{rr}^2 + E_{cr}^2 + E_{rc}^2) + b_{fs}(E_{fc}^2 + E_{cf}^2 + E_{fr}^2 + E_{rf}^2) \tag{2}$$

Here, $E_{ij}$ is the strain tensor in the muscle fiber coordinate system, and $C$, $b_f$, $b_t$, and bfs are material parameters that have been previously fit by Guicione et al to accurately model the mechanical behavior of canine cardiac tissue[16]. In this simulation, the normal tissue will have a C=0.88 kPa, and a $b_f$=18.46, $b_t$=3.58, and $b_{fs}$=1.27, as previously described. The infarct region will have an increased stiffness, which is modeled by an increase in the value C from 0.88 to 1.4 kPa, and the borderzone will have the same material properties as those defined for the remote zone. Stress components are computed from this function by taking the partial derivative of the strain energy function with respect to the strain component of interest.

In addition, active cardiac fiber contraction and force generation is also incorporated in the FEM model. The total systolic cardiac stress is simulated as the sum of the passive stress induced by chamber internal pressure, as well as an active force component generated in the local muscle fiber direction by contraction of the fibers. This active stress contribution can be approximated as a function of time, peak intracellular calcium concentration, and sarcomere length[17]. By adjusting parameters of the model in a similar manner as was done with the passive material properties, the infarct region will be made either non contracting (dyskinetic) or slightly contracting (akinetic), and contractility in the borderzone will be reduced as modeled previously.[12]

In addition to the cardiac mechanical properties, the injected hydrogel will have to be modeled as well. The material will be dealt with differently in the FEM model than the normal cardiac tissue. The systolic parameters will be adjusted such that it adds no contractibility, and its stiffness will be either be directly modeled as a viscoelastic material of a complex modulus of 0.5-2 kPa and a loss angle of 10 degrees[2], or if the software can not model this viscoelasticity, it will be modeled as an isotropic elastic material with a stiffness of 0.5-2 kPa.

Cardiac Simulation

The heart will be simulated in both diastolic filling and systolic contraction as previously described[6]. Solutions will be obtained for diastolic filling by simulation of a stepwise pressure increase from 0-20 mmHg. End systolic solutions will be obtained from 0-120 mm Hg. End systolic pressure—volume relationships (ESPVR), and end diastolic pressure—volume relationships (EDPVR) will be calculated from the converged mathematical solutions. ESPVR will be fit with a linear approximation, while EDPVR will be approximated with a quadratic. From these relationships the stroke volume, or cardiac output can be calculated as follows—

$$SV = \frac{V_{ED} - V_o}{1 + \frac{E_{ES}}{E_A}} \quad (3)$$

Where $V_{ED}$ is the end diastolic volume, $E_{ES}$ is the slope of the end systolic pressure-volume relationship, and $E_A$ is aortic elastance, which is assumed to be constant.

The starling relation will be used to globally depict functional changes to the system. The starling relation is calculated by normalizing determined stroke volume to the end diastolic pressure, and a curve can be generated over all modeled end diastolic pressures. A change in the shape of the curve would indicate an overall change in cardiac performance, with an increase of stroke volume at all pressures indicating a positive effect, while a decrease indicating an impediment to cardiac function.

An additional output from the study will be end systolic and end diastolic material stress along the direction of local muscle fibers. Cauchy stress will be output from the FEM model for the various configurations to look for a reduction in fiber stress as a result of the injection of the hydrogel into the cardiac wall.

Both these outputs, local stress effects and global function, will be evaluated for a range of viscoelastic material properties of the hydrogel, and depending on modeling time, differing injection patterns will also be investigated as well as total injection volume of gel. From the generated results, it will be shown whether the injection of the gel makes a difference to cardiac function or local fiber stress in the borderzone. These results can then be used to formulate and deliver a gel for maximum mechanical improvement.

Example 19

Introduction

Acute damage wrought by myocardial infarctions (MIs) continues to combine with post-MI remodeling to result in heart failure for many patients. To date, no treatments have succeeded in preventing or reversing the progression of this heart failure; new techniques, such as cellular based regenerative medicine, are therefore urgently needed. This approach may involve carefully designed biomaterials, transplanted stem cell populations and novel surgical implantation or reconstruction in an attempt both to replace functional myocytes and to regenerate a working myocardium. Stem cell transplantation to the damaged left ventricle has received widespread attention in the last decade, and numerous preclinical[1-5] and even early clinical[6-8] studies have been reported. However, despite the positive experimental results obtained with numerous types of transplanted cell types, including bone marrow derived mesenchymal stem cells (BMSCs),[3,9,10] endothelial progenitor cells,[2] and embryonic stem cells,[11] definitive demonstration of functional regeneration of an organized myocardium remains an unmet goal. As the survival of transplanted cells has come under srutiny,[12] the addition of extracellular matrices (ECMs) to provide a suitable microenvironment for the implanted cells has been explored, including such biomaterials as fibrin glue,[13] the biologically derived basement membrane synthetic ECM material Matrigel™,[11] collagen foam,[14] and peptide based self associative gels[15,16].

In addition to any benefits associated directly with increased cell survival after transplantation, the injection of at least some of these materials alone has improved long-term metrics of ventricular function, possibly achieved through biomechanical stabilization of the injured myocardial wall, limitation of post-infarct stresses, and amelioration of the remodeling process.[17] However, most of the materials used in these early studies are derived biologically, and therefore pose potential problems of disease transmission and of purity and reproducibility in large scale manufacturing. More importantly, first generation proofs of principal with these materials do not lend themselves to systematic optimization, since little modification of these complex natural substrates is feasible. We have therefore developed novel, fully synthetic biomaterials for cardiac tissue engineering that offer substantial advantages over naturally derived substances, including controlled chemistry, tunable presentation of mechanical and chemical signals, and greater ease of regulatory approval.

This study details the development of a synthetic biomimetic hydrogel polymer as an injectable ECM for cardiac tissue engineering. We have chosen to exploit a polymer system referred to as a semi-interpenetrating polymer network (sIPN); a copolymer network of N-Isopropylacrylamide and acrylic acid, intertwined around linear chains of polyacrylic acid that have peptide based cellular binding domains chemically tethered.[18-21] When polymerized in aqueous solution, this polymer forms a loosely cross-linked and highly hydrated hydrogel of controllable mechanical properties, and has the ability to sustain the growth of a cell population. In this context, control of mechanical properties of the cellular milieu is of increasing importance as it has shown to affect proliferation and differentiation of cells.[21-23] Within this hydrogel, cells can be entrained for direct injection into the injured myocardium, after which the material warms and stiffens in place due to a lower critical solution temperature (LCST) phase change. Following implantation, this stiffened material is degraded through cell-based proteolytic action within the myocardium, as it is cross-linked with matrix metalloprotease (MMP) sensitive peptide sequences. We use this advanced engineered biomaterial to test the hypotheses that injected materials, with or without cells, can help support the injured myocardium, and that by designing systems for specific cellular proliferation, the survival of transplanted cells in the myocardium will be enhanced.

Methods and Materials

Hydrogel Synthesis and Characterization

Figure 23:
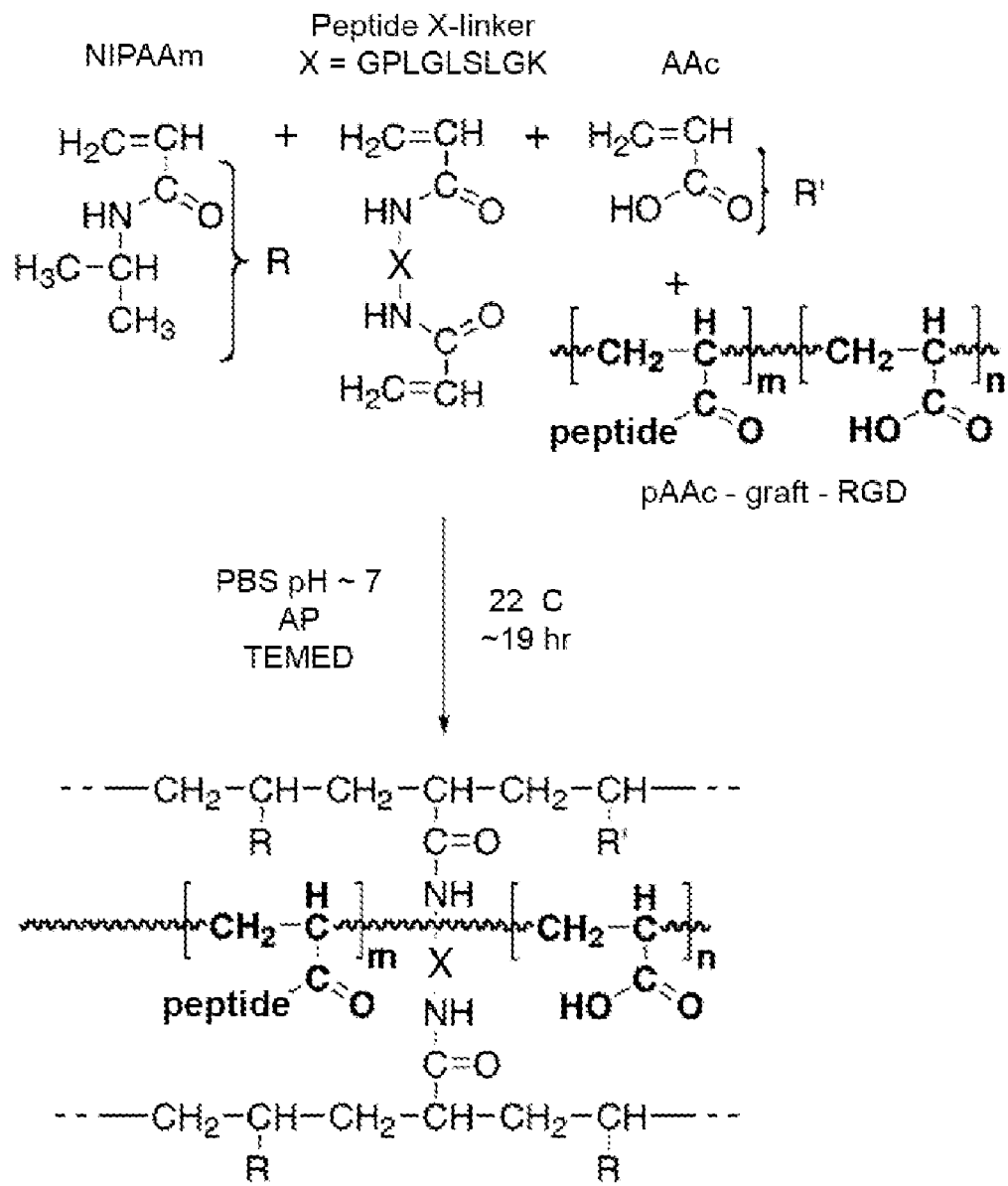
FIG. 23 provides an exemplary polymer synthesis scheme for sIPN thermoresponsive, MMP degradable, peptide modified synthetic ECM hydrogel.

Thermoresponsive poly(N-Isopropylacrylamide-co-acrylic acid) [p(NIPAAm-co-AAc)] hydrogels with MMP peptide degradable cross-linkers were produced through a free radical polymerization reaction similar to previously described methods (FIG. 23).[19-21] Briefly, NIPAAm and AAc monomers (Polysciences Inc) in a 95:5 molar ratio, along with 0.3 mol % of a diacrylated MMP labile peptide sequence (GPLGLSLGK; SEQ ID NO: 21) were dissolved at 3-5 wt % in incomplete PBS (iPBS). Polyacrylic acid (pAAc) linear chains coupled to a bone sialoprotein derived -RGD-peptide sequence (pAAc-graft-RGD), synthesized as described previously[19,21] was then added in the 0-0.8 mg/ml range (corresponding to a -RGD-peptide concentration of ~0-100 M). The resulting solutions were degassed with dry $N_2$, mixed with the free radical initiator ammonimum persulfate (AP) and the accelerator N,N,N',N'-tetramethylethylenediamine (TEMED), and allowed to polymerize overnight under $N_2$. After polymerization, the set hydrogels were washed of unreacted monomers by through sequential rinses in iPBS and cycles through the hydrogels LCST.

Mechanical properties of the hydrogels synthesized at varying polymer weight percentages were tested using parallel plate rheology. For each synthesized material, 3 mL of hydrogel was loaded onto a temperature controlled rheometer (MCR300, Anton Paar, Ashland, Va.) with 50 mm sandblasted parallel plates, and the complex modulus of the materials determined using a 5% dynamically loaded strain at a gap height of 1.0 mm. Sample modulus was first measured across a range of frequencies (0.01-14 Hz) at 22° C., then the sample is slowly warmed to 37° C., and the frequency again swept to test the mechanical properties after the LCST.

Cell Isolation and Characterization

We used an established cell culture system to maintain and expand well-characterized green fluorescent protein (GFP)-expressing mouse BMSCs in vitro. Briefly, marrow was flushed from the tibia and femur of adult GFP transgenic mice (8-12 weeks of age) and subjected to density centrifugation to eliminate many of the mature leukocytes. BMSCs are known to preferentially attach to polystyrene surfaces, and differential plating was used to eliminate hematopoietic cell lineages. BMSCs were propagated in alpha minimum essential medium (αMEM), with Glutamax plus 10% fetal bovine serum until reaching a logarithmic phase of cell growth. These bone marrow-derived cell lines have been associated with a pattern of stem cell marker expression consistent with the reported literature regarding these cells, including CD-90, CD-71, and CD-117, but not hematopoietic markers CD-34 or CD-45.

Hydrogel Cell Culture

For three dimensional (3D) cell culture studies, hydrogels were synthesized in the characterized stiffness range of 3-5% total polymer content in the same monomer ratios as above. Synthesized pAAc-graft-RGD-graft—was incorporated into the gels at 0 mg/ml, 0.4 mg/ml and 0.8 mg/ml, giving bulk concentrations of 0, ~50 M and ~100 M. Polymerizing hydrogel solutions were mixed as was done for the bulk synthesis, and then 200 L aliquots of the reacting solutions pipetted quickly onto methoxysilane treated glass coverslips in order to create a permanent bond between the surface and the forming polymer network. After overnight polymerization, hydrogel samples were rinsed 3× in iPBS and sterilized by a 30 minute incubation in 70% EtOH. [24] There were rinsed again 3× in sterile iPBS followed by equilibration in culture media (alpha-MEM w/o nucleosides, 10% FBS, 2 mM L-glutamine, and antibiotics) at 37° C. for 4 hours.

To seed the hydrogel samples, GFP BMSCs were suspended at a concentration of $10^6$ cells/mL, and 200 L of this solution containing $2\times10^5$ cells was injected into the coverslip bound hydrogels in a series of 15-20 injections using a 23 gauge needle. These cell loaded hydrogels were then placed into 16 well tissue culture plates and 1.5 mL of warm media was added to each well. Samples were incubated at 37° C. in 5% $CO_2$ for 14 days, with media changed every 2-3 days, and gels removed at 1, 4, 7, and 14 days. Gel samples were then visualized using a fluorescent scope, homogenized using hand held small volume homogenizer, and assayed for cell number using Cyquant GR assay against generated cell number standards. Cell proliferation as a function of stiffness and RGD content at day 14 was mapped to a response surface by fitting the data to a quadratic curve using MATLAB software (Mathworks, Inc, Natick, Mass.).

Mouse Infarct Model and Injections

A sIPN formulation of 4% 95:5 p(NIPAAm-co-AAc) with 0.3 mol % cross-linker content and 50 M RGD was synthesized for direct injection with or without entrained BMSCs. This hydrogel demonstrated optimal injection properties as determined both by rheological measurements and by surgeon feedback. This formulation also supported the attachment and proliferation of BMSCs in vitro in 3D culture conditions. EGFP-expressing BMSCs were grown to near confluence, trypsinized, counted, and pelleted in a microfuge tube. Sufficient quantities of hydrogel were then pipetted into the tube and mixed with a spatula to achieve a cell density of $10^7$ cells/mL. The cell/gel mixture was microscopically visualized to ascertain the distribution of cells within the matrix, and kept at 4° C. until injection. The same procedure was used with cold, liquid growth factor-reduced, phenol red-free Matrigel™ (BD Biosciences, San Jose, Calif.) to make an injectable cell/gel mixture as a comparative control. A control suspension of cells in sterile saline was also prepared at the same cell concentration.

Male C57Bl/6 mice (68 weeks old) were anesthetized with pentobarbitol prior to intubation with a 24 gauge angiocatheter. Inhalation anesthesia was then instituted with 1.5% isoflurane using a rodent ventilator (Harvard) at 115 breaths/min. A left lateral thoracotomy incision was placed at the level of the fourth interspace and a 6-0 polypropylene suture was used to ligate the left anterior descending (LAD) artery at approximately ⅓ the distance from the base to the apex of the heart. Blanching of the distal left ventricular wall was observed to verify ligation. Immediately after generation of the infarct, inhalation anesthesia was reduced and 10 L of the test material was injected into the anticipated infarct border zone region of the LV wall. Animals were ventilated for approximately 15 minutes after chest closure, and were then recovered in a light-warmed incubator. Animals in the sham surgery group underwent thoracotomy without LAD ligation.

Echocardiography was undertaken at 2, 4, and 6 weeks after MI in gently restrained, conscious mice. Fractional shortening (FS) for each animal was analyzed from M-mode images using an Accuson echocardiograph with a 13 MHz transducer.

Mice were sacrificed at 6 weeks post-MI. Thin frozen sections were obtained to preserve the GFP signal of the implanted cells, which, when present, could be detected easily via fluorescent microscopy of the ventricle wall. For each heart, sections were taken every 200 microns from the apex of the ventricle to the point of LAD ligation. Adjacent sections were stained using Gomori's trichrome, and image analysis software was used to determine the thicknesses of both the infracted and the remote, uninfarcted left ventricular wall, as well as the extent of infarction.

Statistics

Differences in FS between treatment groups were assessed using analysis of variance followed by pairwise Holms corrected t-tests. A P-value<0.05 was considered statistically significant, with Bonferroni correction where appropriate.

Results sIPN Hydrogels and In Vitro Cell Culture

Figure 24:
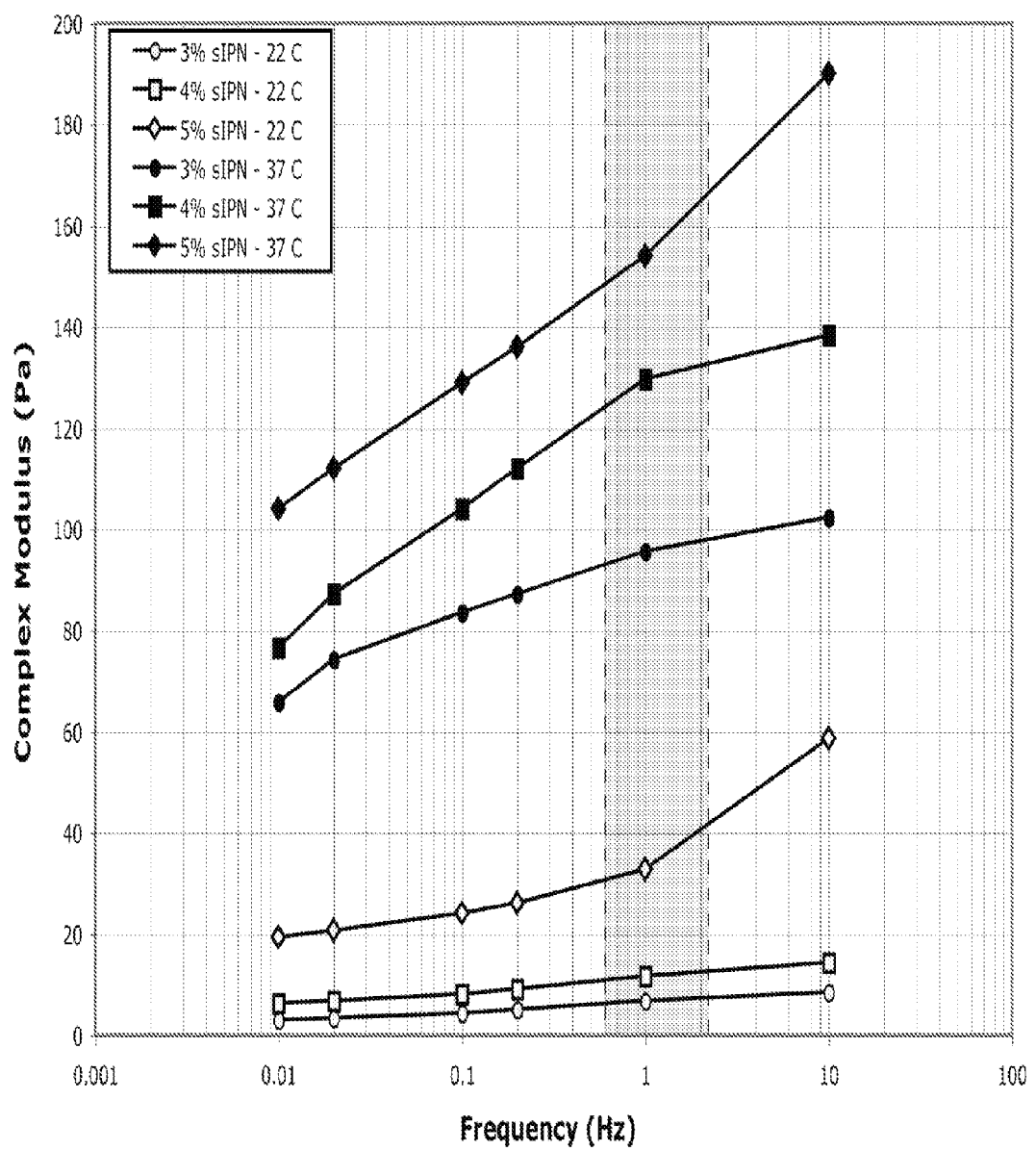
FIG. 24 is a depiction of complex modulus as a function of temperature, frequency, and composition of the sIPN hydrogels according to an exemplary embodiment of the invention. Gray zone indicates cardiac tissue engineering range of frequency loadings.
Figure 25A:
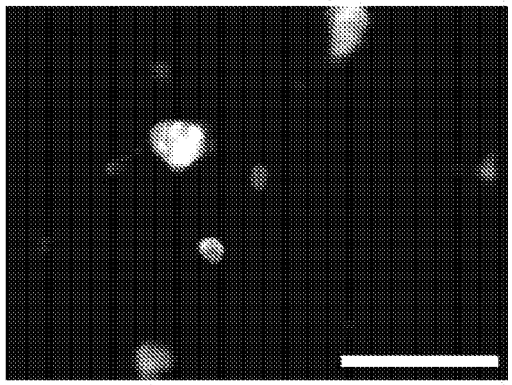
Figure 25A:
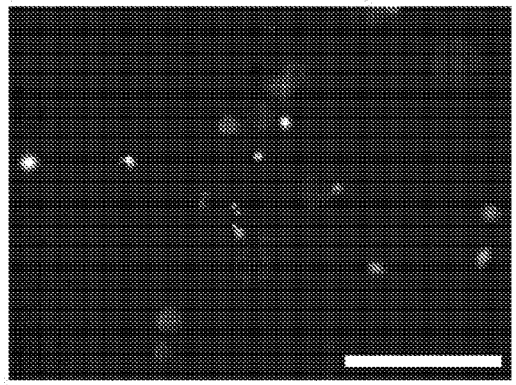
Figure 25A:
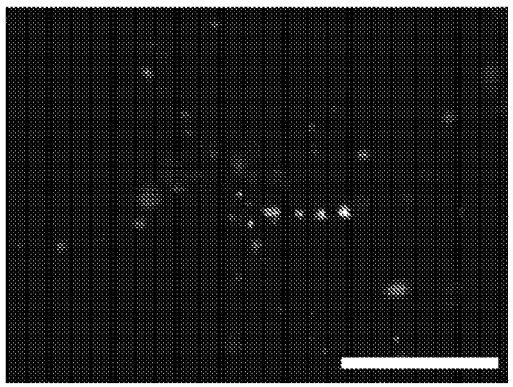
Figure 25A:
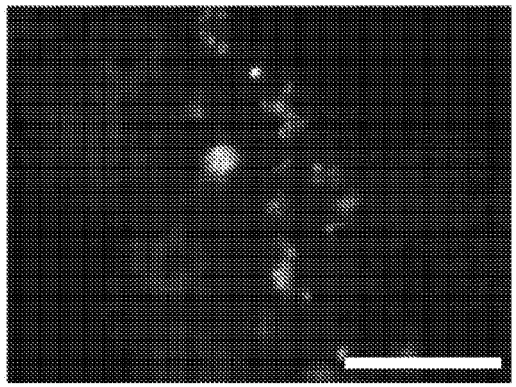
Figure 25A:
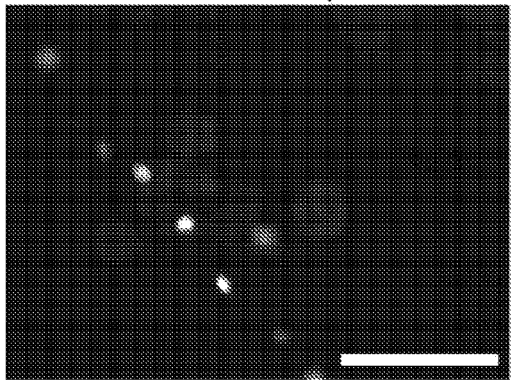
Figure 25A:
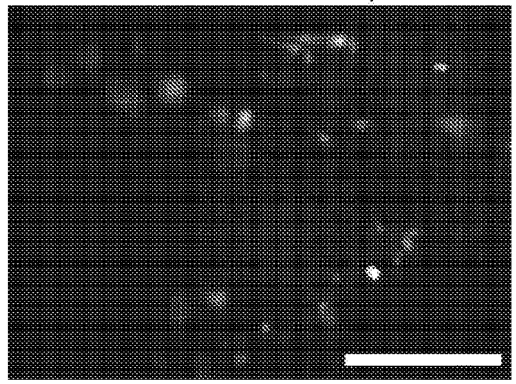
Figure 25B:
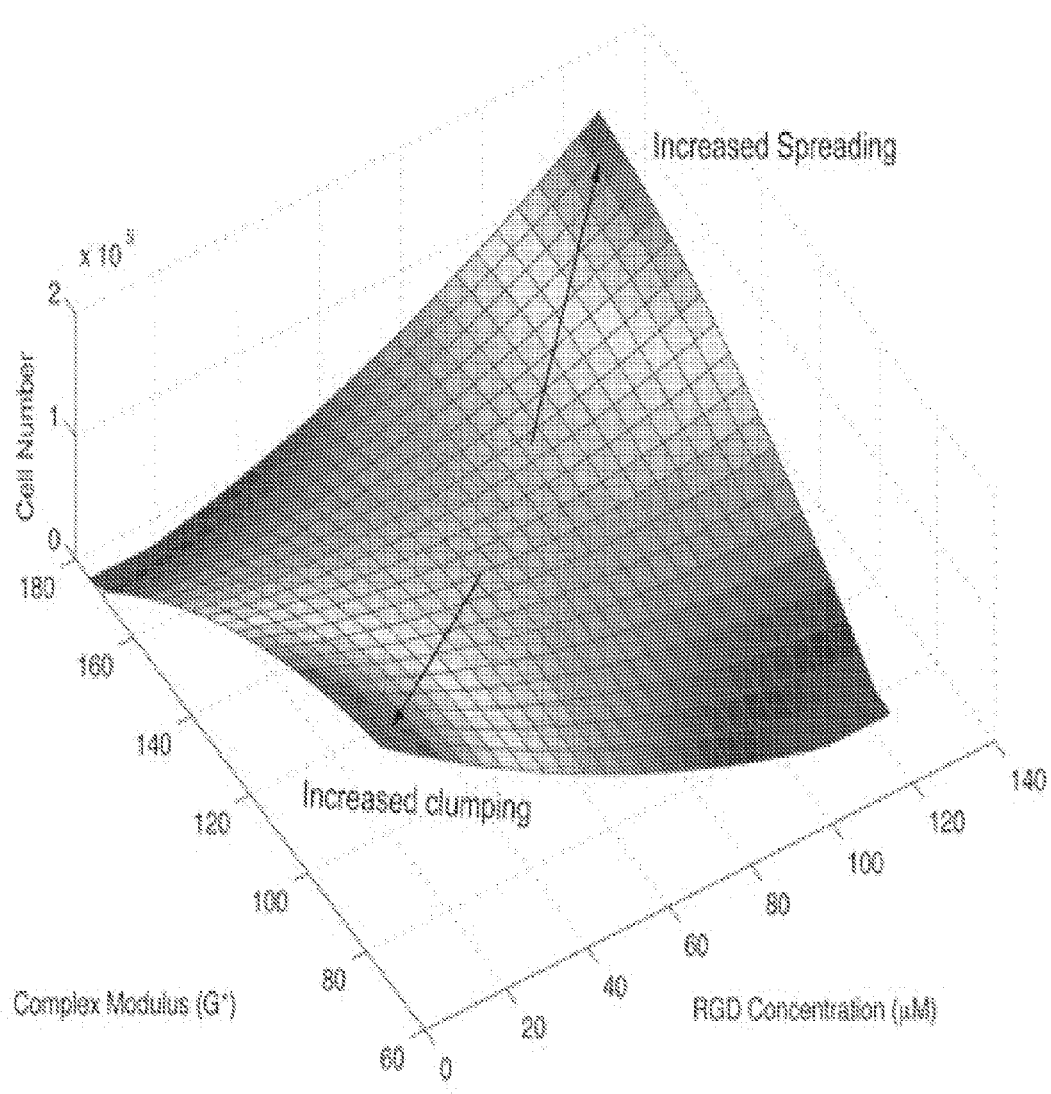
In FIG. 25B, the generated response surface shows how cell proliferation is a function of RGD and modulus at t=14 days.

Hydrogels were made with controllable mechanical properties, having a complex shear modulus range spanning 95-155 Pa at biological temperature and relevant cyclical loading ranges (FIG. 24). At this temperature (37° C.), there was also a significant qualitative difference between the formulations; the 3% gel was very soft and pliable while the 5% gel was much stiffer. The mechanical properties at body temperature differed substantially from those measured at room temperature, which indicated very low moduli with high loss angles (data not shown), that allowed them to be passed through small gauge needles. However, there was a change in room temperature stiffness between 4% and 5% polymer weight compositions, and this difference was reproducibly detected by surgeons during delivery of the gels through a 30 gauge needle.

In vitro cell proliferation varied as a function of matrix stiffness and bsp-RGD (15) content (FIG. 25, right). All sIPN formulations were able to sustain cell growth over 2 weeks as reflected by increased cell count; the cell binding peptide concentration, however, influenced cell growth as did material stiffness. Even in the absence of RGD, BMSCs proliferated well on the softer gels, while increases in RGD enhanced cellular proliferation on the stiffer gels. All variationos of the 4% peptide cross-linked gel demonstrated substantial cellular proliferation after 1 week. These data are reflected in the generated response surface in FIG. 3 that shows the fit cellular proliferation response as a function of both stiffness and RGD content.

Microscopy of these samples (FIG. 3, left) shows sparse but proliferating cells within the matrix with morphology dependent on the matrix composition. In the softest gels with no conjugated RGD, cells grew in aggregates, without spreading, indicating that the cell—cell interaction was favored over cell-matrix interaction. With the addition of RGD, cell clumps diminished, as did cell proliferation as assayed from the CyQUANT analysis. These observations indicated that the addition of RGD influenced the interaction of cells with the matrix, but was not sufficient on its own to induce cell proliferation. As the matrix was stiffened, cell spreading, as detected by light microscopy, was more abundant, and proliferation was stable across a range of RGD concentrations. However, at the highest stiffness, in which proliferation was highly dependant on RGD concentration, this trend reversed, and extensive cell spreading was visible in the high RGD samples. Thus, the matrix organizes cells in two distinct ways: when the modulus and ligand concentrations are low, then cell-cell adhesion and aggregate proliferation was dominant; when the modulus and ligand density were high, cell-matrix adhesion was preferred.

Murine Infarct model

Figure 26:
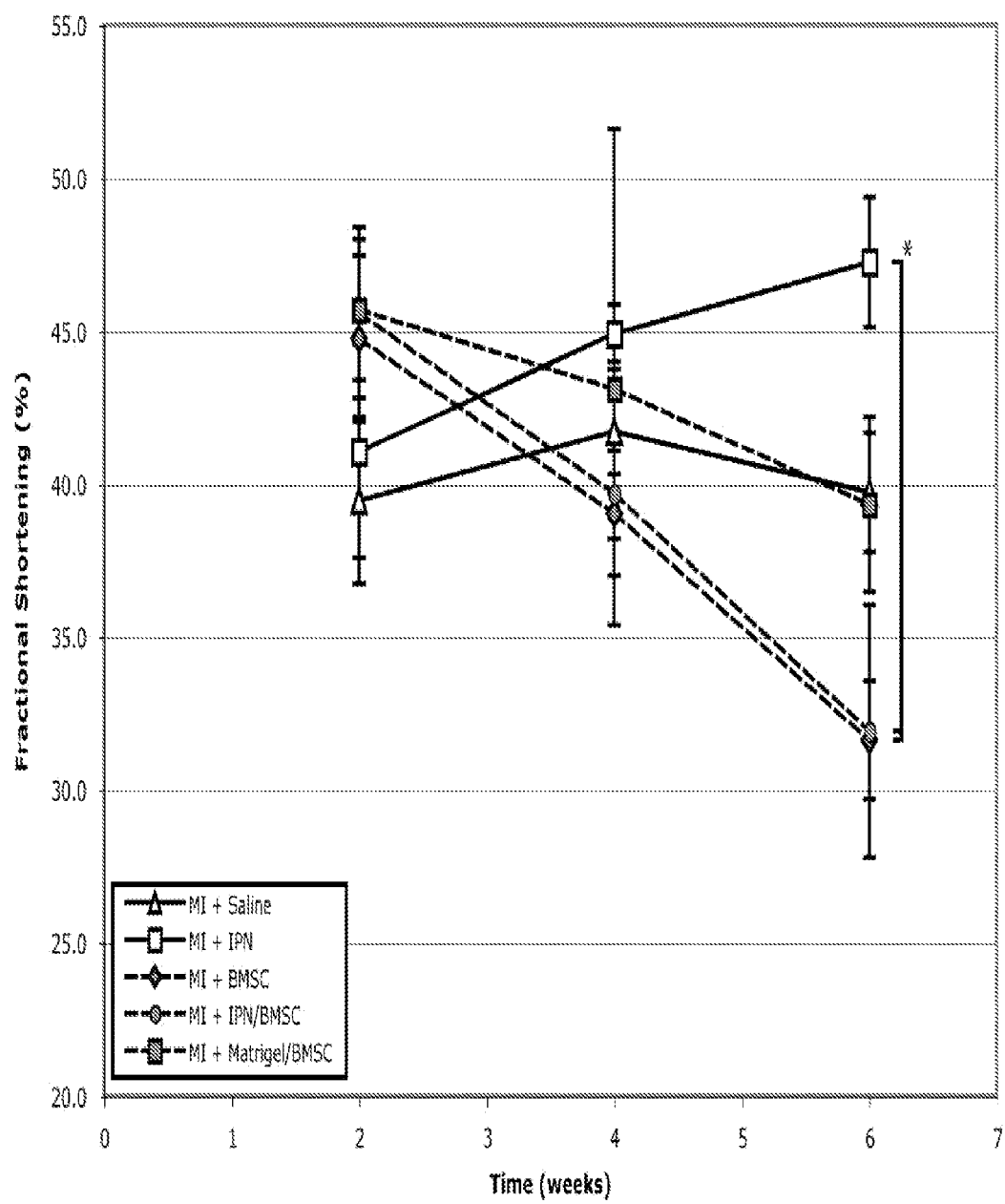
FIG. 26 shows FS data as a function of time for all animal groups. Solid lines indicate conditions without added cells while dashed lines represent groups with added cells. Error bars indicate SEM.
Figure 27:
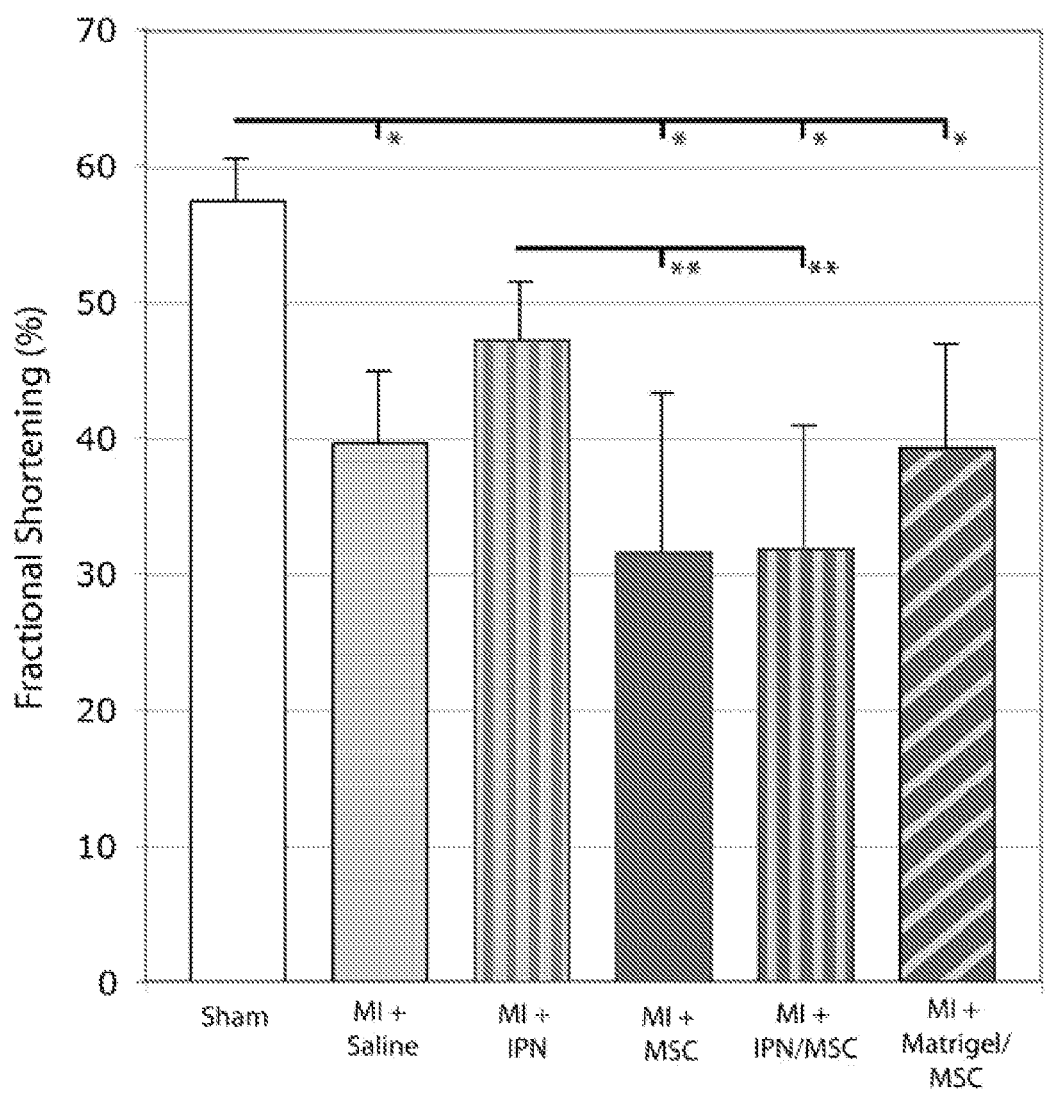
FIG. 27 provides the six week FS data of injection conditions compared to controls. The sham surgery is statistically different ($p<0.05$) than all groups except the MI+sIPN alone group. Two of the three groups which received cells are also significantly different from the MI+sIPN group as well.

Both matrix injection and cell transplantation had measurable effects on ventricular function, as reflected in echocardiographic assessment of FS, after acute MI (FIG. 26). The decline in LV function in control infarcts injected with saline alone did not change significantly over the time course studied. In contrast, hearts receiving sIPN injection alone experienced a gradual improvement in FS, and were the only group studied in which LV function was not statistically different from the uninfarcted sham control at week 6 (FIG. 27). All groups with cell injection, either alone, with sIPNs, or with Matrigel™, displayed a numerical, but not statistically significant, improvement in FS compared to saline injection at 2 weeks; all hearts treated with cell transplantation, however, also showed a progressive decline in LV function at later time points.

Histological Examination

GFP-positive cells were detected in 38% of the hearts after injection with sIPN, while none were observed in the hearts undergoing injection of cells alone (Table 1). Donor cells were detected in 25% of hearts after Matrigel™-enhanced transplantation (P=NS). Donor cells were localized to the area of injection near the infarct (FIG. 29). In the subgroup of ventricles in which matrix material was still detectable in the infarct border zone (n=8, X with sIPN and X with Matrigel™), infarct thickness was higher at all time points, and FS, mean remote wall thickness, and extent of infarction were non-significantly improved (Table 2).

Pooled Analyses

Figure 28:
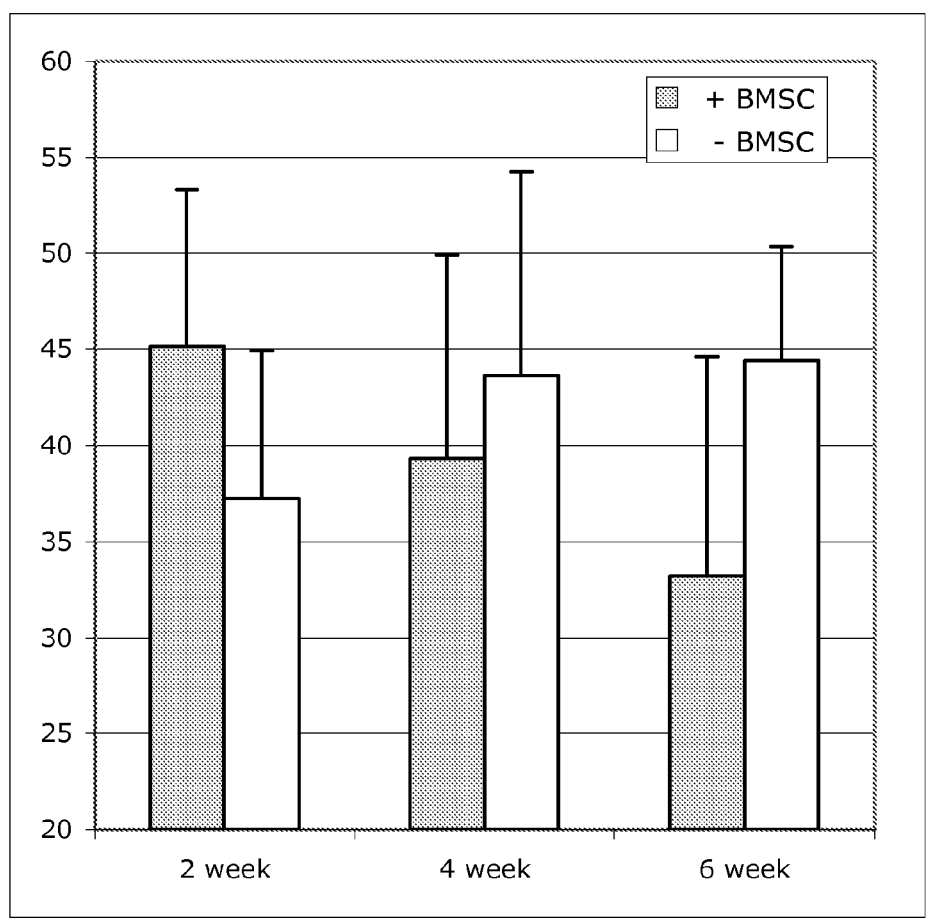
FIG. 28 is a graph showing the temporal changes in FS after a generated MI. Gray bars indicate mean measurements of animals with added BMSCs while white bars are animals without added BMSCs. Error bars indicate standard deviation.

By pooling the groups that received cells and comparing them to those which did not, significant differences could be seen between the therapeutic approaches (FIG. 28). At two weeks, the addition of cells results in a significantly higher FS (45.6% versus 39.8%, $p<0.05$), while at 6 weeks FS was worse in hearts that received any cell formulation (34.2% versus 42.5%, $p<0.05$). Given the technical limitations on accuracy of injection site relative to eventual border zone formation in this murine model, we attempted to account for this variability in a subgroup analysis of specimens in which we found definitive histologic confirmation of border zone injection of matrix alone (n=8, X Matrigel, X sIPN). By aggregating all recipients of a confirmed border zone injection, FS was found to be higher at each time point, and at 6 weeks infarct size was reduced and LV wall thickness was increased in both the infarcted region and in the remote uninfarcted myocardium compared to sham controls.

Discussion

In this study, synthetic injectable hydrogels were designed with a range of mechanical and biological properties that yielded different cellular responses in vitro. These in vitro data were then used to identify specific formulations that might promote the survival of transplanted cells and/or provide mechanical stabilization to an injured ventricular wall. In vivo studies indicated that these fully synthetic systems can be injected directly into the beating ventricle after ischemic injury without migrating, and that they can be designed to degrade slowly over a 6 week time course. Alone these matrices improved the progression of post-MI ventricular remodeling as measured by echocardiography; they also improved the survival of a population of transplanted stem cells. Although the transplantation of BMSCs was associated with an increase in ventricular performance at early time points, this trend was reversed at later time points, as FS decreased in all groups that received cell transplantation.

Although previous reports of cell transplantation using natural matrix products such as Matrigel™ have not described the transient nature of this benefit, our data are nevertheless largely consistent with those reports. Kofidis et al,[11] followed hearts for only two weeks after Matrigel™—enhanced cell transplantation. In fact, we were able to reproduce the early benefit observed in that study with Matrigel,™ but found that this benefit was lost at later time points. In addition, Kutshka et al,[14] recently observed in a working heterotopic heart transplant model that ex vivo cell transplantation, alone or with either a Matrigel™ or collagen matrix, yielded a similar trend. In that study, FS was increased at 2 weeks in all four groups that had cells implanted, compared to controls. Average FS in each of these groups then decreased by week 4, at a time when average FS had increased in the control infarct and matrix-alone groups compared to their function at 2 weeks.

Numerous studies of cardiac cell transplantation and tissue engineering have been reported, both with BMSC and with other cell types. Although somewhat disappointing, the transient nature of the functional benefit we observed with cell transplantation is not inconsistent with much of the published literature, in which the time courses reported often extended for only 2-4 weeks after transplantation. One limitation to achieving long-term benefit may be the consistent difficulty to obtain true regeneration of functional tissue through differentiation and integration of donor cells in the host myocardium. Regression of early benefit may also be related to the rapid loss of the majority of transplanted cells, usually within days after transplantation; this death of transplanted cells might also be directly detrimental to the myocardium through exacerbation of inflammatory signals or other biochemical sequelae. The enhancement of longer-term survival of at least a portion of transplanted cells that we observed with matrix-assisted transplantation provides an intriguing opportunity to overcome this limitation. Although the degree of enhanced survival seen with either natural or synthetic first-generation matrices was not adequate to sustain early functional benefit, the tunable, easily engineered nature of our synthetic matrices may represent a critical advantage over naturally occurring matrices that cannot easily be modified or redesigned.

Injection of either biodegradable or non-biodegradable material into the injured myocardium has been hypothesized by our group and others to have a stabilizing effect via reduction of elevated fiber stresses.[11,25] We have recently utilized an advanced computational finite element model of the infracted heart to demonstrate the theoretical benefit of injecting non-contractile material into the infarct border zone after MI.[17] The immediate reduction in fiber stress predicted by this model may also have an ameliorative effect on chronic post-MI remodeling, in which high border zone stress has been implicated.[26,27] The trend we observed in this study with injections of gel alone provides early support for this hypothesis, as did our subgroup analysis of documented successful border zone injections, and warrants further development of so-called matrix assisted myocardial stabilization (MAMS).

In this study, we also demonstrated the application of engineering principles in the rational design of materials for specific tissue engineering applications. We have taken a broad biomaterial platform and used data from mechanical and in vitro biological testing to begin optimization for both mechanical stabilization of the myocardial wall and for enhanced delivery of cell transplants. A formulation chosen based on survival and spreading of cells in three dimensional in vitro culture conditions did enhance cell survival, although it is unclear whether the degree of increased survival with this early generation matrix had a positive effect on post-MI remodeling. This fully engineered system, however, specifically tuned for cardiac tissue engineering applications with controllable and well characterized chemistry, may facilitate the clinical translation of tissue engineering approaches as remaining basic cellular questions on regenerative therapies are resolved.

Tables:

TABLE 1

Infarct size of various animal groups and fraction of ventricles that had clearly visible GFP cells at t = 6 weeks

|  | Fraction GFP+ | Infarct Size (%) |
| --- | --- | --- |
| MI + Saline | N/A | 19 +/− 27 |
| MI + sIPN | N/A | 28 +/− 25 |
| MI + BMSC | 0/7 | 42 +/− 20 |
| MI + Matrigel/BMSC | 2/8 | 19 +/− 21 |
| MI + sIPN/BMSC | 3/8 | 30 +/− 11 |

TABLE 2

Comparison between animal subgroups which had clearly visible material contained within the infarct border zone and those without.

|  | +BZ Material | −BZ Material |
| --- | --- | --- |
| Infarct Thickness (mm) | 0.40 +/− .12 | 0.23 +/− .15 |
| Remote Thickness (mm) | 1.14 +/− .12 | 1.11 +/− .21 |
| Apical Infarct Area (%) | 21 +/− 12 | 31 +/− 22 |
| 2 week FS (%) | 45.8 +/− 7.5 | 43.7 +/− 7.5 |
| 4 week FS (%) | 44.7 +/− 10.3 | 39.6 +/− 9.8 |
| 6 week FS (%) | 41.0 +/− 9 | 37.1 +/− 11.4 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of stabilizing an injured or defective myocardial wall in a patient comprising forming a prosthetic in situ by injecting, at a pre-selected site in the myocardial wall of the patient, a polymer network comprising:
- a cross-linked polymer, said cross-linked polymer being a hydrogel; and
- a linear polymer, the polymer chains of which are entangled within said cross-linked polymer and derivatized with a bioactive molecule, wherein said linear polymer is not covalently bonded to said cross-linked polymer and said polymer network has an LCST (lower critical solution temperature) above room temperature and at or below mammalian body temperature.

2. The method of claim 1, wherein the site is pre-selected using a finite element model of the myocardium.

3. The method of claim 2, wherein the finite element model is generated in accordance with imaging data of the patient's myocardium.

4. The method of claim 1, wherein the pre-selected site is at the left ventricle wall.

5. The method of claim 1, wherein the pre-selected site is at an infarct border zone.

6. The method of claim 5, wherein the pre-selected site is at an anterior wall of the infarct border zone.

7. The method of claim 1, wherein the polymer network has a complex modulus of about 0.2 to about 1.5 kPa at a temperature at or above the LCST.

8. The method of claim 1, wherein the polymer network has a complex modulus of about 0.95 to about 1.55 kPa at mammalian body temperature.

9. The method of claim 1, wherein said bioactive molecule is an -Arg-Gly-Asp-containing peptide.

10. The method of claim 1, wherein said bioactive molecule is a Sonic Hedgehog growth factor.

11. The method of claim 1, comprising injecting a fractional volume of polymer network that is about 0.5% to about 5% of the wall volume.

12. The method of claim 11, comprising injecting a fractional volume of polymer network of about 4.5% of the wall volume.

13. The method of claim 1, wherein the LCST is about 37° C.

14. The method of claim 1, wherein said cross-linked polymer is a copolymer of N-isopropyl acrylamide and acrylic acid cross-linked by amino acid sequences comprising the -QPQGLAK-sequence motif and said linear polymer comprises polyacrylic acid.

* * * * *

SEQUENCE LISTING

<160> NUMBER OF SEQ ID NOS: 28

<210> SEQ ID NO 1
<211> LENGTH: 15
<212> TYPE: PRT
<213> ORGANISM: Artificial Sequence
<220> FEATURE:
<223> OTHER INFORMATION: 15-mer bone sialopeptide sequence; bsp-RGD(15)

<400> SEQUENCE: 1

Cys Gly Gly Asn Gly Glu Pro Arg Gly Asp Thr Tyr Arg Ala Tyr
1               5                   10                  15

<210> SEQ ID NO 2
<211> LENGTH: 18
<212> TYPE: PRT
<213> ORGANISM: Artificial Sequence
<220> FEATURE:
<223> OTHER INFORMATION: bone sialopeptide sequence; bsp-RGD(15)-FITC
<220> FEATURE:
<221> NAME/KEY: BINDING
<222> LOCATION: 16
<223> OTHER INFORMATION: FITC

<400> SEQUENCE: 2

Cys Gly Gly Asn Gly Glu Pro Arg Gly Asp Thr Tyr Arg Ala Tyr Lys
1               5                   10                  15

Gly Gly

<210> SEQ ID NO 3
<211> LENGTH: 15
<212> TYPE: PRT
<213> ORGANISM: Artificial Sequence
<220> FEATURE:
<223> OTHER INFORMATION: bone sialopeptide sequence; bsp-RGE(15)

<400> SEQUENCE: 3

Cys Gly Gly Asn Gly Glu Pro Arg Gly Glu Thr Tyr Arg Ala Tyr
1               5                   10                  15

<210> SEQ ID NO 4
<211> LENGTH: 10
<212> TYPE: PRT
<213> ORGANISM: Artificial Sequence
<220> FEATURE:
<223> OTHER INFORMATION: adhesion peptide
<220> FEATURE:
<221> NAME/KEY: ACETYLATION
<222> LOCATION: 1
<220> FEATURE:
<221> NAME/KEY: AMIDATION
<222> LOCATION: 10

<400> SEQUENCE: 4

Cys Gly Gly Phe His Arg Arg Ile Lys Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: heparin binding motif

<400> SEQUENCE: 5

Phe His Arg Arg Ile Lys Ala
1               5

<210> SEQ ID NO 6
<211> LENGTH: 5
<212> TYPE: PRT
<213> ORGANISM: Artificial Sequence
<220> FEATURE:
<223> OTHER INFORMATION: active motif for iodination and glycosylation
<220> FEATURE:
<223> OTHER INFORMATION: Xaa = D-Tyr

<400> SEQUENCE: 6

Arg Gly Asp Xaa Lys
1               5

<210> SEQ ID NO 7
<211> LENGTH: 19
<212> TYPE: PRT
<213> ORGANISM: Artificial Sequence
<220> FEATURE:
<223> OTHER INFORMATION: lam-IKVAV(19) peptide

<400> SEQUENCE: 7

Cys Ser Arg Ala Arg Lys Gln Ala Ala Ser Ile Lys Val Ala Val Ser
1               5                   10                  15

Ala Asp Arg

<210> SEQ ID NO 8

-continued

<211> LENGTH: 20
<212> TYPE: PRT
<213> ORGANISM: Artificial Sequence
<220> FEATURE:
<223> OTHER INFORMATION: left primer for GFAP marker

<400> SEQUENCE: 8

```
Gly Ala Cys Cys Thr Gly Cys Gly Ala Cys Cys Thr Thr Gly Ala Gly
1               5                   10                  15

Thr Cys Cys Thr
            20
```

<210> SEQ ID NO 9
<211> LENGTH: 20
<212> TYPE: PRT
<213> ORGANISM: Artificial Sequence
<220> FEATURE:
<223> OTHER INFORMATION: right primer for GFAP marker

<400> SEQUENCE: 9

```
Thr Cys Thr Cys Cys Thr Cys Cys Thr Thr Gly Ala Gly Gly Cys Thr
1               5                   10                  15

Thr Thr Gly Gly
            20
```

<210> SEQ ID NO 10
<211> LENGTH: 21
<212> TYPE: PRT
<213> ORGANISM: Artificial Sequence
<220> FEATURE:
<223> OTHER INFORMATION: hybridization TAQMAN oligo for GFAP marker

<400> SEQUENCE: 10

```
Thr Cys Cys Thr Thr Gly Gly Ala Gly Ala Gly Gly Cys Ala Ala Ala
1               5                   10                  15

Thr Gly Cys Gly Cys
            20
```

<210> SEQ ID NO 11
<211> LENGTH: 23
<212> TYPE: PRT
<213> ORGANISM: Artificial Sequence
<220> FEATURE:
<223> OTHER INFORMATION: left primer for beta-tubulin-III

<400> SEQUENCE: 11

```
Gly Cys Ala Thr Gly Gly Ala Thr Gly Ala Gly Ala Thr Gly Gly Ala
1               5                   10                  15

Gly Thr Thr Cys Ala Cys Cys
            20
```

<210> SEQ ID NO 12
<211> LENGTH: 25
<212> TYPE: PRT
<213> ORGANISM: Artificial Sequence
<220> FEATURE:
<223> OTHER INFORMATION: right primer for beta-tubulin-III marker

<400> SEQUENCE: 12

```
Cys Gly Ala Cys Thr Cys Cys Thr Cys Gly Thr Cys Gly Thr Cys Ala
1               5                   10                  15

Thr Cys Thr Thr Cys Ala Thr Ala Cys
            20                  25
```

<210> SEQ ID NO 13

-continued

<211> LENGTH: 20
<212> TYPE: PRT
<213> ORGANISM: Artificial Sequence
<220> FEATURE:
<223> OTHER INFORMATION: hybridization TAQMAN oligo for beta-tubulin-III marker

<400> SEQUENCE: 13

```
Thr Gly Ala Ala Cys Gly Ala Cys Cys Thr Gly Gly Thr Gly Thr Cys
1               5                   10                  15

Thr Gly Ala Gly
            20
```

<210> SEQ ID NO 14
<211> LENGTH: 20
<212> TYPE: PRT
<213> ORGANISM: Artificial Sequence
<220> FEATURE:
<223> OTHER INFORMATION: left primer for nestin marker

<400> SEQUENCE: 14

```
Gly Ala Gly Cys Thr Cys Thr Cys Thr Gly Gly Gly Cys Ala Ala Gly
1               5                   10                  15

Thr Gly Gly Ala
            20
```

<210> SEQ ID NO 15
<211> LENGTH: 20
<212> TYPE: PRT
<213> ORGANISM: Artificial Sequence
<220> FEATURE:
<223> OTHER INFORMATION: right primer for nestin marker

<400> SEQUENCE: 15

```
Cys Thr Cys Cys Cys Ala Cys Cys Gly Cys Thr Gly Thr Thr Gly Ala
1               5                   10                  15

Thr Thr Thr Cys
            20
```

<210> SEQ ID NO 16
<211> LENGTH: 22
<212> TYPE: PRT
<213> ORGANISM: Artificial Sequence
<220> FEATURE:
<223> OTHER INFORMATION: hybridization TAQMAN oligo for nestin marker

<400> SEQUENCE: 16

```
Ala Gly Gly Ala Cys Ala Gly Thr Cys Ala Gly Cys Ala Gly Thr Gly
1               5                   10                  15

Cys Cys Thr Gly Cys Ala
            20
```

<210> SEQ ID NO 17
<211> LENGTH: 21
<212> TYPE: PRT
<213> ORGANISM: Artificial Sequence
<220> FEATURE:
<223> OTHER INFORMATION: left primer for 18S marker

<400> SEQUENCE: 17

```
Gly Thr Ala Ala Cys Cys Cys Gly Thr Thr Gly Ala Ala Cys Cys Cys
1               5                   10                  15

Cys Ala Thr Thr Cys
            20
```

```
<210> SEQ ID NO 18
<211> LENGTH: 21
<212> TYPE: PRT
<213> ORGANISM: Artificial Sequence
<220> FEATURE:
<223> OTHER INFORMATION: right primer for 18S marker

<400> SEQUENCE: 18

Cys Cys Ala Thr Cys Cys Ala Ala Thr Cys Gly Gly Thr Ala Gly Thr
1               5                   10                  15

Ala Gly Cys Gly Ala
            20

<210> SEQ ID NO 19
<211> LENGTH: 22
<212> TYPE: PRT
<213> ORGANISM: Artificial Sequence
<220> FEATURE:
<223> OTHER INFORMATION: hybridization TAQMAN oligo for 18S marker

<400> SEQUENCE: 19

Ala Ala Gly Thr Gly Cys Gly Gly Thr Cys Ala Thr Ala Ala Gly
1               5                   10                  15

Cys Thr Thr Gly Cys Gly
            20

<210> SEQ ID NO 20
<211> LENGTH: 7
<212> TYPE: PRT
<213> ORGANISM: Artificial Sequence
<220> FEATURE:
<223> OTHER INFORMATION: cleavable sequence

<400> SEQUENCE: 20

Gln Pro Gln Gly Leu Ala Lys
1               5

<210> SEQ ID NO 21
<211> LENGTH: 9
<212> TYPE: PRT
<213> ORGANISM: Artificial Sequence
<220> FEATURE:
<223> OTHER INFORMATION: peptide crosslinker

<400> SEQUENCE: 21

Gly Pro Leu Gly Leu Ser Leu Gly Lys
1               5

<210> SEQ ID NO 22
<211> LENGTH: 8
<212> TYPE: PRT
<213> ORGANISM: Artificial Sequence
<220> FEATURE:
<223> OTHER INFORMATION: peptide crosslinker

<400> SEQUENCE: 22

Gly Pro Leu Gly Met His Gly Lys
1               5

<210> SEQ ID NO 23
<211> LENGTH: 8
<212> TYPE: PRT
<213> ORGANISM: Artificial Sequence
<220> FEATURE:
<223> OTHER INFORMATION: test peptide substrate

<400> SEQUENCE: 23
```

```
Gly Pro Leu Gly Met Arg Gly Leu
1               5

<210> SEQ ID NO 24
<211> LENGTH: 8
<212> TYPE: PRT
<213> ORGANISM: Artificial Sequence
<220> FEATURE:
<223> OTHER INFORMATION: test peptide substrate

<400> SEQUENCE: 24

Gly Pro Arg Pro Phe Asn Tyr Leu
1               5

<210> SEQ ID NO 25
<211> LENGTH: 8
<212> TYPE: PRT
<213> ORGANISM: Artificial Sequence
<220> FEATURE:
<223> OTHER INFORMATION: test peptide substrate

<400> SEQUENCE: 25

Gly Pro Phe Gly Phe Lys Ser Leu
1               5

<210> SEQ ID NO 26
<211> LENGTH: 7
<212> TYPE: PRT
<213> ORGANISM: Artificial Sequence
<220> FEATURE:
<223> OTHER INFORMATION: test peptide substrate

<400> SEQUENCE: 26

Gly Ala Leu Gly Leu Ser Leu
1               5

<210> SEQ ID NO 27
<211> LENGTH: 8
<212> TYPE: PRT
<213> ORGANISM: Artificial Sequence
<220> FEATURE:
<223> OTHER INFORMATION: test peptide substrate

<400> SEQUENCE: 27

Gly Pro Lys Gly Val Tyr Ser Leu
1               5

<210> SEQ ID NO 28
<211> LENGTH: 8
<212> TYPE: PRT
<213> ORGANISM: Artificial Sequence
<220> FEATURE:
<223> OTHER INFORMATION: test peptide substrate

<400> SEQUENCE: 28

Gly Pro Gln Gly Leu Ala Gly Gln
1               5
```